US011180460B2

(12) United States Patent
Angst et al.

(10) Patent No.: US 11,180,460 B2
(45) Date of Patent: *Nov. 23, 2021

(54) AMINO PYRIMIDINE DERIVATIVES

(71) Applicant: Novartis AG, Basel (CH)

(72) Inventors: Daniela Angst, Basel (CH); Francois Gessier, Altkirch (FR); Anna Vulpetti, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/571,405

(22) Filed: Sep. 16, 2019

(65) Prior Publication Data
US 2020/0010426 A1  Jan. 9, 2020

Related U.S. Application Data

(63) Continuation of application No. 15/974,190, filed on May 8, 2018, now Pat. No. 10,457,647, which is a continuation of application No. 15/135,296, filed on Apr. 21, 2016, now abandoned, which is a continuation of application No. 14/540,140, filed on Nov. 13, 2014, now Pat. No. 9,512,084.

(30) Foreign Application Priority Data

Nov. 29, 2013 (EP) .................... 13195081

(51) Int. Cl.
C07D 405/12 (2006.01)
C07D 403/12 (2006.01)
A61K 31/505 (2006.01)
A61K 31/506 (2006.01)
A61P 19/02 (2006.01)
C07D 239/47 (2006.01)
C07D 401/14 (2006.01)
C07D 401/10 (2006.01)
C07D 401/12 (2006.01)
A61P 29/00 (2006.01)
A61P 35/02 (2006.01)

(52) U.S. Cl.
CPC .......... C07D 239/47 (2013.01); A61K 31/505 (2013.01); A61K 31/506 (2013.01); A61P 29/00 (2018.01); A61P 35/02 (2018.01); C07D 401/10 (2013.01); C07D 401/12 (2013.01); C07D 401/14 (2013.01); C07D 403/12 (2013.01); C07D 405/12 (2013.01)

(58) Field of Classification Search
CPC ........ C07D 239/47; A61P 29/00; A61P 19/02; A61K 31/505; A61K 31/506
See application file for complete search history.

(56) References Cited

U.S. PATENT DOCUMENTS

| 6,160,010 A | 12/2000 | Uckun et al. |
| 2010/0216733 A1 | 8/2010 | Auclair et al. |
| 2010/0261776 A1 | 10/2010 | Conklin et al. |
| 2012/0071497 A1 | 3/2012 | Buggy et al. |
| 2015/0011751 A1 | 1/2015 | Kawahata et al. |

FOREIGN PATENT DOCUMENTS

| EP | 2322200 A2 | 5/2011 |
| WO | 2001/066107 A2 | 9/2001 |
| WO | 2002/38797 A2 | 5/2002 |
| WO | 2006/099075 A2 | 9/2006 |
| WO | 2008/033858 A2 | 3/2008 |
| WO | 2008/039218 A2 | 4/2008 |
| WO | 2008/110624 A2 | 9/2008 |
| WO | 2009/137596 A1 | 11/2009 |
| WO | 2010/009342 A2 | 1/2010 |
| WO | 2010/100070 A1 | 9/2010 |
| WO | 2010/122038 A1 | 10/2010 |
| WO | WO2012/135801 A1 | 10/2012 |
| WO | 2012/158843 A2 | 11/2012 |
| WO | 2012/170976 A2 | 12/2012 |
| WO | 2013/003629 A2 | 1/2013 |
| WO | 2013/008095 A1 | 1/2013 |
| WO | 2013/023084 A2 | 2/2013 |
| WO | 2013/059738 A2 | 4/2013 |
| WO | 2013/063401 A1 | 5/2013 |
| WO | 2013/083666 A1 | 6/2013 |
| WO | 2013/133367 A1 | 9/2013 |
| WO | 2013/157021 A1 | 10/2013 |
| WO | 2013/157022 A1 | 10/2013 |
| WO | 2013/173518 A1 | 11/2013 |
| WO | 2014025976 A1 | 2/2014 |
| WO | 2014/055928 A2 | 4/2014 |
| WO | WO2015/079417 A1 | 6/2015 |

OTHER PUBLICATIONS

Norman (Expert Opinion on Inestigational Drugs, 2016; 25(8):891-899) (Year: 2016).*
Stilt et al (Curr Allergy Asthma Rep. 2013; 13:556-562).

* cited by examiner

Primary Examiner — Marcos L Sznaidman
Assistant Examiner — Rayna Rodriguez
(74) Attorney, Agent, or Firm — Francine F. Li

(57) ABSTRACT

The present invention describes new amino pyrimidine derivatives and pharmaceutically acceptable salts thereof which appear to interact with Bruton's tyrosine kinase (Btk). Accordingly, the novel amino pyrimidines may be effective in the treatment of autoimmune disorders, inflammatory diseases, allergic diseases, airway diseases, such as asthma and chronic obstructive pulmonary disease (COPD), transplant rejection, cancers e.g. of hematopoietic origin or solid tumors.

13 Claims, No Drawings

AMINO PYRIMIDINE DERIVATIVES

The present invention describes new amino pyrimidine derivatives that are good drug candidates.

The compounds of the present invention may generally exhibit a selective inhibition of Bruton's tyrosine kinase (Btk).

BACKGROUND OF THE INVENTION

The essential role of Btk in autoimmune disease is underlined by the observations that Btk-deficient mice are protected in standard preclinical models for rheumatoid arthritis (Jansson & Holmdahl 1993), systemic lupus erythematosus (Steinberg et al. 1982), as well as allergic disease and anaphylaxis (Hata et al. 1998). In addition, many cancers and lymphomas express Btk and appear to be dependent on Btk function (Davis et al. 2010). The role of BTK in diseases including autoimmunity, inflammation and cancer has been recently reviewed (Tan et al. 2013; Rickert 2013).

SUMMARY OF THE INVENTION

Inhibition of Btk activity by the compounds of the present invention may therefore be useful in the treatment of a wide range of disorders, particularly Btk-related diseases or disorders. This may include, but is not limited to autoimmune disorders and inflammatory diseases, such as rheumatoid arthritis, systemic lupus erythematosus or vasculitic conditions. It may include, but is not limited to allergic diseases, airway diseases, such as asthma and chronic obstructive pulmonary disease (COPD) or conditions caused by delayed or immediate type hypersensitivity and anaphylaxis. It may include, but is not limited to acute or chronic transplant rejection or graft versus host disease. It may include, but is not limited to cancers of hematopoietic origin or solid tumors, including chronic myelogenous leukemia, myeloid leukemia, non-Hodgkin lymphoma and other B cell lymphomas.

More particularly, in embodiment 1 the present invention provides a compound of formula (I) or a pharmaceutically acceptable salt thereof;

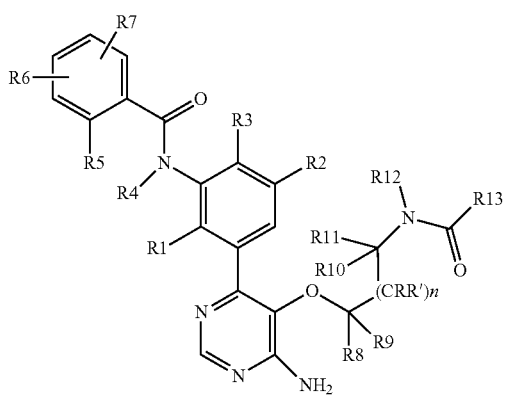

(I)

wherein,
R1 is hydrogen, $C_1$-$C_6$ alkyl optionally substituted by hydroxy;
R2 is hydrogen or halogen;
R3 is hydrogen or halogen;
R4 is hydrogen;
R5 is hydrogen or halogen;
or R4 and R5 are attached to each other and stand for a bond, —$CH_2$—, —$CH_2$—$CH_2$—, —CH=CH—, —CH=CH—$CH_2$—; —$CH_2$—$CH_2$—CH—; or —$CH_2$—$CH_2$—$CH_2$—;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R, R', R10 and R11 independently from each other stand for H, or $C_1$-$C_6$ alkyl optionally substituted by $C_1$-$C_6$ alkoxy; or any two of R8, R9, R, R', R10 and R11 together with the carbon atom to which they are bound may form a 3-6 membered saturated carbocyclic ring;
R12 is hydrogen or $C_1$-$C_6$ alkyl optionally substituted by halogen or $C_1$-$C_6$ alkoxy; or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl, $C_1$-$C_6$ alkoxy or N,N-di-$C_1$-$C_6$ alkyl amino; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 2 of the present invention provides a compound of formula (I) or a pharmaceutically acceptable salt thereof wherein,
R1 is hydrogen, or $C_1$-$C_6$ alkyl optionally substituted by hydroxy;
R2 is halogen;
R3 is hydrogen;
R4 is hydrogen;
R5 is halogen;
or R4 and R5 are attached to each other and stand for a bond, —CH2-, —CH2-CH2-, —CH=CH—, —CH=CH—CH2-; —CH2-CH=CH—; or —CH2-CH2-CH2-;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;
R and R' are hydrogen;
R12 is hydrogen or $C_1$-$C_6$ alkyl optionally substituted by halogen;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 3 of the present invention provides a compound of formula (I) or a pharmaceutically acceptable salt thereof wherein,
R1 is hydrogen, or $C_1$-$C_6$ alkyl optionally substituted by hydroxy;
R2 is halogen;
R3 is hydrogen;

R4 is hydrogen;

R5 is halogen;

R6 and R7 stand independently from each other for H, $C_1$-$C_6$ alkyl optionally substituted by hydroxyl, $C_3$-$C_6$ cycloalkyl optionally substituted by halogen or hydroxy, or halogen;

R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;

R and R' are hydrogen;

R12 is hydrogen or $C_1$-$C_6$ alkyl optionally substituted by halogen;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;

n is 0 or 1; and

R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 4 of the present invention provides a compound of formula (I) or a pharmaceutically acceptable salt thereof wherein, R1 is hydrogen, $C_1$-$C_6$ alkyl optionally substituted by hydroxy;

R2 is hydrogen or halogen;

R3 is hydrogen or halogen;

R4 and R5 are attached to each other and stand for a bond, —CH$_2$—, —CH$_2$—CH$_2$—, —CH═CH—, —CH═CH—CH$_2$—; —CH$_2$—CH═CH—; or —CH$_2$—CH$_2$—CH$_2$—;

R6 and R7 stand independently from each other for H, $C_1$-$C_6$ alkyl optionally substituted by hydroxyl, $C_3$-$C_6$ cycloalkyl optionally substituted by halogen or hydroxy, or halogen;

R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;

R and R' are hydrogen;

R12 is hydrogen or $C_1$-$C_6$ alkyl optionally substituted by halogen;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;

n is 0 or 1; and

R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 5 of the present invention provides a compound of formula (I) or a pharmaceutically acceptable salt thereof wherein, R1 is hydrogen, $C_1$-$C_6$ alkyl optionally substituted by hydroxy;

R2 is hydrogen or halogen;

R3 is hydrogen or halogen;

R4 and R5 are attached to each other and stand for a —CH$_2$—CH$_2$—, or —CH═CH—;

R6 and R7 stand independently from each other for H, $C_1$-$C_6$ alkyl optionally substituted by hydroxyl, $C_3$-$C_6$ cycloalkyl optionally substituted by halogen or hydroxy, or halogen;

R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;

R and R' are hydrogen;

R12 is hydrogen or $C_1$-$C_6$ alkyl optionally substituted by halogen:

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;

n is 0 or 1; and

R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 6 of the present invention provides a compound of formula (I) or a pharmaceutically acceptable salt thereof wherein, R1 is hydrogen, or $C_1$-$C_6$ alkyl optionally substituted by hydroxy;

R2 is halogen;

R3 is hydrogen;

R4 is hydrogen;

R5 is halogen;

R6 and R7 stand independently from each other for H, $C_1$-$C_6$ alkyl optionally substituted by hydroxyl, $C_3$-$C_6$ cycloalkyl optionally substituted by halogen or hydroxy, or halogen;

R8, R9, R10 and R11 independently from each other stand for H, or $C_1$-$C_6$ alkyl;

R and R' are hydrogen;

R12 is hydrogen or $C_1$-$C_6$ alkyl optionally substituted by halogen;

n is 0 or 1; and

R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 7 of the present invention provides a compound of formula (I) or a pharmaceutically acceptable salt thereof wherein, R1 is hydrogen, or $C_1$-$C_6$ alkyl optionally substituted by hydroxy;

R2 is halogen;

R3 is hydrogen;

R4 is hydrogen;

R5 is halogen;

R6 and R7 stand independently from each other for H, $C_1$-$C_6$ alkyl optionally substituted by hydroxyl, $C_3$-$C_6$ cycloalkyl optionally substituted by halogen or hydroxy, or halogen;

R8 and R9, independently from each other stand for H, or $C_1$-$C_6$ alkyl;

R and R' are hydrogen;

R12 and any one of R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;

n is 0 or 1; and

R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

Embodiment 8 of the present invention provides a compound of formula (I) or a pharmaceutically acceptable salt thereof wherein,
R1 is hydrogen, or $C_1$-$C_6$ alkyl optionally substituted by hydroxy;
R2 is halogen;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl;
R and R' are hydrogen;
R12 is hydrogen or $C_1$-$C_6$ alkyl optionally substituted by halogen;
n is 0 or 1; and
R13 is $C_2$-$C_6$ alkenyl optionally substituted by $C_1$-$C_6$ alkyl or $C_1$-$C_6$ alkoxy.

Embodiment 9 of the present invention provides a compound of formula (I) or a pharmaceutically acceptable salt thereof wherein,
R1 is hydrogen, or $C_1$-$C_6$ alkyl optionally substituted by hydroxy;
R2 is fluoro;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8 and R9 independently from each other stand for H, or $C_1$-$C_6$ alkyl;
R12 and any one of R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0; and
R13 is $C_2$-$C_6$ alkenyl optionally substituted by $C_1$-$C_6$ alkyl or $C_1$-$C_6$ alkoxy; or $C_2$-$C_6$ alkynyl optionally substituted by $C_1$-$C_6$ alkyl or $C_1$-$C_6$ alkoxy.

Embodiment 10 of the present invention provides a compound of formula (I) or a pharmaceutically acceptable salt thereof wherein,
R1 is $C_1$-$C_6$ alkyl;
R2 is fluoro;
R3 is hydrogen;
R4 is hydrogen;
R5 is fluoro;
R6 and R7 stand independently from each other for H, $C_3$-$C_6$ cycloalkyl, or halogen;
R8, R9, R10 and R11 stand for H;
R12 is methyl;
n is 0; and
R13 is $C_2$-$C_6$ alkenyl optionally substituted by $C_1$-$C_6$ alkyl.

With regard to a compound of formula (1) the following significances represent further embodiments of the invention independently, collectively or in any combination or in any sub-combination thereof:
1. R1 is methyl or hydroxymethyl;
2. R2 is hydrogen or fluoro;
3. R3 is hydrogen
4. R1 is methyl or hydroxymethyl and R2 and R3 are independently hydrogen or fluoro;
5. R4 is hydrogen;
6. R4 together with R5 is —$CH_2$—$CH_2$—, or —CH=CH—;
7. R5 is fluoro;
8. R6 is H and R7 is $C_3$-$C_6$-cycloalkyl and in particular cyclopropyl;
9. R7 is H and R6 is $C_2$-$C_6$-cycloalkyl and in particular cyclopropyl;
10. R8, R9, R10 and R11 stand for H;
11. R12 and any one of R8, R9, R, R', R10 or R11 together with the atoms to which they are bound may form a 4, 5, 6 or 7 membered azacyclic ring, which ring may optionally be substituted by halogen, hydroxyl, $C_1$-$C_6$ alkyl or $C_1$-$C_6$ alkoxy;
12. R8, R9, R10 and R11 independently from each other stand for H, or $C_1$-$C_6$ alkyl; or any two of R8, R9, R, R', R10 and R11 together with the carbon atom to which they are bound may form a 3-6 membered saturated carbocyclic ring;
13. R12 is hydrogen and R13 stands for $C_2$-$C_6$ alkenyl optionally substituted by $C_1$-$C_6$ alkyl;
14. n=0;
15. R12 is methyl.

In another embodiment the present invention provides a compound of formula (I) or a pharmaceutically acceptable salt thereof for use as a medicament.

In another embodiment the present invention provides a compound of formula (I) or a pharmaceutically acceptable salt thereof for use in the treatment of a disease or disorder mediated by Btk.

In another embodiment the present invention provides a compound of formula (I) or a pharmaceutically acceptable salt thereof, which is selected from:

N-(3-(5-((1-Acryloylazetidin-3-yl)oxy)-6-aminopyrimidin-4-yl)-5-fluoro-2-methylphenyl)-4-cyclopropyl-2-fluorobenzamide;

(E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide;

N-(3-(6-Amino-5-((1-propioloylazetidin-3-yl)oxy)pyrimidin-4-yl)-5-fluoro-2-methylphenyl)-4-cyclopropyl-2-fluorobenzamide;

N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide;

N-(3-(5-((1-Acryloylpiperidin-4-yl)oxy)-6-aminopyrimidin-4-yl)-5-fluoro-2-methylphenyl)-4-cyclopropyl-2-fluorobenzamide;

N-(3-(6-Amino-5-(2-(N-methylacrylamido)ethoxy)pyrimidin-4-yl)-5-fluoro-2-methylphenyl)-4-cyclopropyl-2-fluorobenzamide;

(E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide;

N-(3-(6-Amino-5-(2-(N-methylpropiolamido)ethoxy)pyrimidin-4-yl)-5-fluoro-2-methylphenyl)-4-cyclopropyl-2-fluorobenzamide;

(E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide;

N-(3-(6-Amino-5-(2-(N-methylbut-2-ynarnido)ethoxy)pyrimidin-4-yl)-5-fluoro-2-methylphenyl)-4-cyclopropyl-2-fluorobenzamide;

N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide;

N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide;

N-(3-(5-(2-Acrylamidoethoxy)-6-aminopyrimidin-4-yl)-5-fluoro-2-methylphenyl)-4-cyclopropyl-2-fluorobenzamide;

N-(3-(6-Amino-5-(2-(N-ethylacrylamido)ethoxy)pyrimidin-4-yl)-5-fluoro-2-methylphenyl)-4-cyclopropyl-2-fluorobenzamide;

N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide;

N-(3-(5-((1-Acrylamidocyclopropyl)methoxy)-6-aminopyrimidin-4-yl)-5-fluoro-2-methylphenyl)-4-cyclopropyl-2-fluorobenzamide;

(S)—N-(3-(5-(2-Acrylamidopropoxy)-6-aminopyrimidin-4-yl)-5-fluoro-2-methylphenyl)-4-cyclopropyl-2-fluorobenzamide;

(S)—N-(3-(6-Amino-5-(2-(but-2-ynamido)propoxy)pyrimidin-4-yl)-5-fluoro-2-methylphenyl)-4-cyclopropyl-2-fluorobenzamide;

(S)—N-(3-(6-Amino-5-(2-(N-methylacrylamido)propoxy)pyrimidin-4-yl)-5-fluoro-2-methylphenyl)-4-cyclopropyl-2-fluorobenzamide;

(S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide;

N-(3-(6-Amino-5-(3-(N-methylacrylamido)propoxy)pyrimidin-4-yl)-5-fluoro-2-methylphenyl)-4-cyclopropyl-2-fluorobenzamide;

(S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide;

(S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide;

(S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one;

N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide;

N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide;

N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide;

2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one;

N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide;

N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide;

N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide;

N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide;

(S)—N-(3-(5-((1-Acryloylazetidin-2-yl)methoxy)-6-aminopyrimidin-4-yl)-5-fluoro-2-methylphenyl)-4-cyclopropyl-2-fluorobenzamide;

(S)—N-(3-(6-Amino-5-((1-propioloylazetidin-2-yl)methoxy)pyrimidin-4-yl)-5-fluoro-2-methylphenyl)-4-cyclopropyl-2-fluorobenzamide;

(S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one;

(R)—N-(3-(5-((1-Acryloylazetidin-2-yl)methoxy)-6-aminopyrinnidin-4-yl)-5-fluoro-2-methylphenyl)-4-cyclopropyl-2-fluorobenzamide;

(R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide;

N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide;

N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide;

and

N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

As used herein, the term "$C_1$-$C_6$ alkyl" refers to a fully saturated branched or unbranched hydrocarbon moiety having up to 6 carbon atoms. Unless otherwise provided, it refers to hydrocarbon moieties having 1 to 6 carbon atoms, 1 to 4 carbon atoms or 1 to 2 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl and the like.

As used herein, the term "$C_2$-$C_6$ alkenyl" refers to an unsaturated branched or unbranched hydrocarbon moiety having 2 to 6 carbon atoms. Unless otherwise provided, C2-C6 alkenyl refers to moieties having 2 to 6 carbon atoms, 2 to 5 carbon atoms, or 2 to 4 carbon atoms. Representative examples of alkenyl include, but are not limited to, ethenyl, n-propenyl, iso-propenyl, n-butenyl, sec-butenyl, iso-butenyl, tert-butenyl, n-pentenyl, isopentenyl, neopentenyl, n-hexenyl, and the like.

As used herein, the term "$C_2$-$C_6$ alkynyl" refers to an unsaturated branched or unbranched hydrocarbon moiety having 2 to 6 carbon atoms, containing at least one triple bond, and which is attached to the rest of the molecule by a single bond. The term "$C_{2-4}$alkynyl" is to be construed accordingly. Examples of $C_{2-6}$alkynyl include, but are not limited to, ethynyl, prop-1-ynyl, but-1-ynyl, pent-1-ynyl and penta-1,4-diynyl and the like.

As used herein, the term "$C_1$-$C_6$ alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1 to 6 carbon atoms, 1 to 4 carbon atoms or 1 to 2 carbon atoms.

As used herein, the term "di $C_{1-6}$alkylamino" refers to a moiety of the formula —N($R_a$)—$R_a$ where each $R_a$ is a $C_{1-6}$alkyl, which may be the same or different, as defined above.

As used herein, the term "$C_3$-$C_6$ cycloalkyl" refers to saturated monocyclic hydrocarbon groups of 3-6 carbon atoms. Cycloalkyl may also be referred to as a carbocyclic ring and vice versa additionally referring to the number of carbon atoms present. Unless otherwise provided, cycloalkyl refers to cyclic hydrocarbon groups having between 3 and 6 ring carbon atoms or between 3 and 4 ring carbon atoms. Exemplary monocyclic hydrocarbon groups include, but are not limited to, cyclopropyl, cyclobutyl, cyclopentyl, and cyclohexyl.

As used herein "$C_2$-$C_6$ alkylenyl oxide" refers to a branched or unbranched hydrocarbon moiety comprising an epoxy group and having from 2 to 6 carbon atoms.

Representative examples include ethylenyl oxide, propylenyl oxide, butylenyl 1,2-oxide, butylenyl 2,3-oxide, butylenyl 3,4-oxide, pentylenyl oxide, hexylenyl oxide, and the like.

As used herein, the term "azacyclic" ring refers to a saturated or unsaturated monocyclic hydrocarbon group of 3-7 carbon atoms as defined for "cycloalkyl", wherein one carbon atom is replaced by a nitrogen atom. It may be also referred to "azacycloalkyl" or "aza hydrocarbon". Unless otherwise provided, azacycloalkyl refers to cyclic aza-hydrocarbon groups having between 2 and 6 ring carbon atoms and one nitrogen atom, between 2 and 4 ring carbon atoms and one nitrogen atom, or between 2 and 3 ring carbon atoms and one nitrogen atom. Exemplary azacyclic groups include, but are not limited to, aziridinyl, azetidinly, pyrrolidinyl, piperidinyl, azepanyl, dihydroazepinyl and the like.

As used herein, the term "halogen" or "halo" refers to fluoro, chloro, bromo, and iodo.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by Btk, or (ii) associated with Btk activity, or (iii) characterized by activity (normal or abnormal) of Btk; or (2) reducing or inhibiting the activity of Btk; or (3) reducing or inhibiting the expression of Btk. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Btk; or reducing or inhibiting the expression of Btk partially or completely.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. Btk modulating properties, e.g. as indicated by in vitro and in vivo tests as provided in the next sections and are therefore indicated for therapy.

Utility

Compounds of the invention may be useful in the treatment of an indication selected from: Autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including but not limited to multiple myeloma; leukemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

In another embodiment, compounds of the invention may be useful in the treatment of autoimmune disorders, inflammatory diseases, allergic diseases, airway diseases, such as asthma and chronic obstructive pulmonary disease (COPD), transplant rejection, cancers e.g. of hematopoietic origin or solid tumors.

In another embodiment, compounds of the invention may be useful in the treatment of cancers of haematopoietic origin including but not limited to multiple myeloma; leukemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and/or Waldenstroem disease.

In another embodiment, compounds of the invention may be useful in the treatment of chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, and/or Grave's disease.

Methods of Synthesizing Amino-Pyrimidines

Agents of the invention, i.e. compounds in accordance to the definition of formula (I), may be prepared by a reaction sequence involving an alkylation of 4-amino-6-chloro-pyrimidin-5-ol 1 with an alkyl halide 2 using an appropriate base, Suzuki coupling with a boronic ester using an appropriate palladium catalyst, such as bis(triphenylphosphine)-palladium(II) dichloride, deprotection using an appropriate acid, such as TFA or HCl, followed by amide formation of the ammonium salt or the free amine with an acid using an appropriate coupling reagent, such as T3P, and an appropriate base, such as DIPEA, or with an acid chloride using an appropriate base, such as DIPEA, as shown in Scheme 1 below:

Scheme 1:
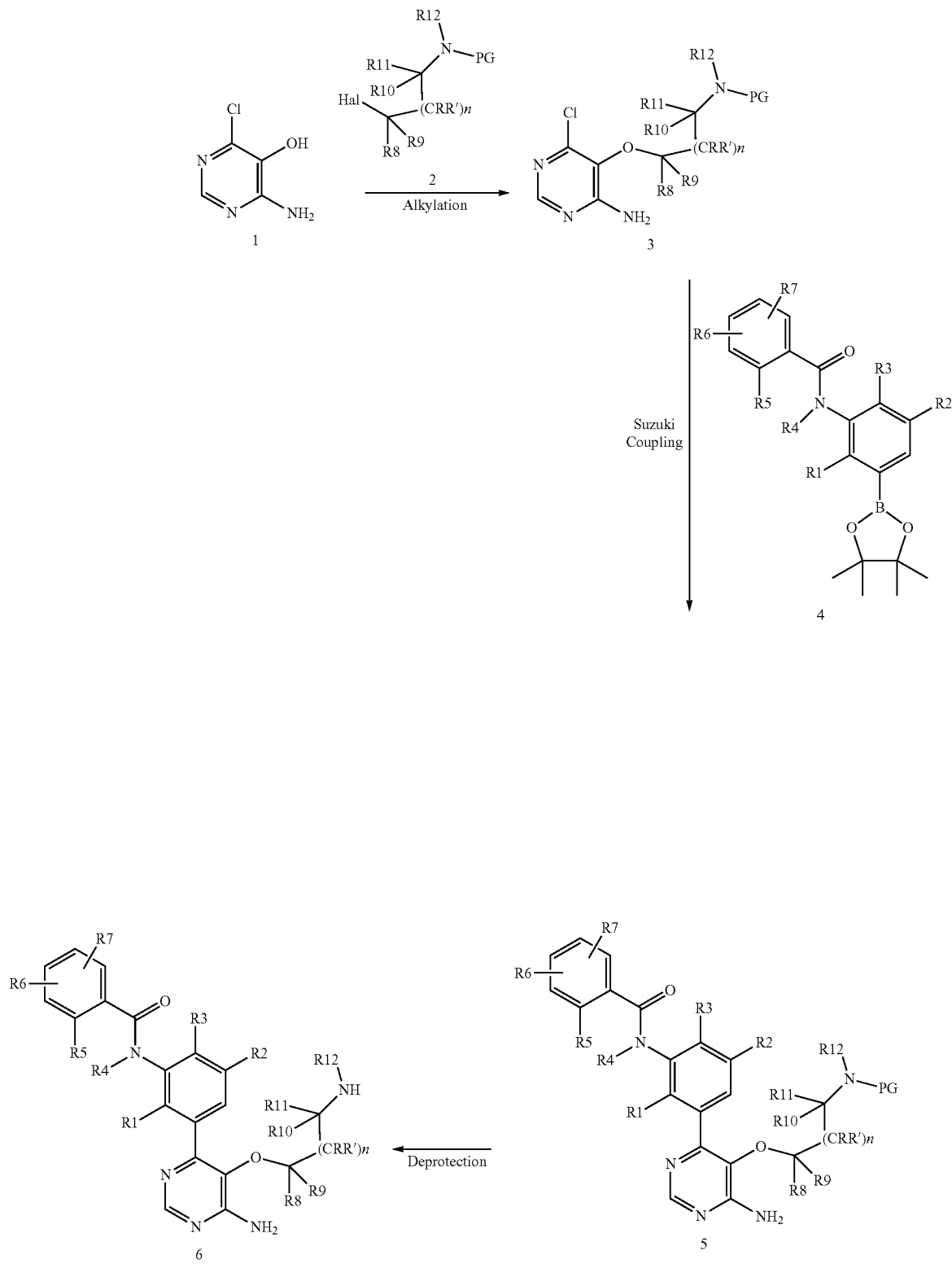

-continued

Alternatively, compounds of the invention may be prepared by an alternative reaction sequence (shown below) comprising the steps of reacting the amino hydroxypyrimidine 1 with the hydroxyl amino-alkyl-derivative 2' in a Mitsunobu reaction to furnish intermediate 3, which intermediate 3 is then reacted via a Suzuki-coupling to yield intermediate 5, which is then deprotected to yield intermediate 6, which is then amidated with an acid or acid chloride to yield the final product 7 as already described in scheme 1.

EXPERIMENTAL SECTION

Abbreviations:
BISPIN: Bis(pinacolato)diboron
Boc t-Butyloxycarbonyl
DCE: Dichloroethane
DCM: Dichloromethane
DIAD: Diisopropyl azodicarboxylate
DIPEA: N-Diisopropylethylamine
DME: 1,2-Dimethoxyethane
DMF: N,N-Dimethylformamide
DMSO: Dimethyl sulfoxide
EtOAc: Ethyl acetate
EtOH: Ethanol
hr: Hour
M: Molar
MeOH: Methanol
min: Minute
NaHMDS: Sodium bis(trimethylsilyl)amide
rt: Retention time
RT: Room temperature
SFC: Supercritical fluid chromatography
Smopex-301: Polymer supported triphenylphosphine
SPE: Solid phase extraction
TBAF: Tetrabutylammonium fluoride
TBDPS: tert-Butyldiphylsilyi
TBHP: tert-Butyl hydroperoxide
TBME: tert-Butyl methyl ether
TEA: Triethylamine
TFA: Trifluoroacetic acid
THF: Tetrahydrofuran
T3P: Propylphosphonic anhydride
XPhos: 2-Dicyclohexylphosphino-2',4',6'-triisopropylbiphenyl $^1$H NMR spectra were recorded on a Bruker 400 MHz NMR spectrometer. Significant peaks are tabulated in the order: multiplicity (s, singlet; d, doublet; t, triplet; q, quartet; m, multiplet; br, broad; v, very) and number of protons. Electron Spray Ionization (ESI) mass spectra were recorded on a Waters Acquity SQD mass spectrometer. Mass spectrometry results are reported as the ratio of mass over charge.

UPLC-MS Method:
Waters Acquity UPLC instrument equipped with PDA detector, Waters Acquity SQD mass spectrometer and Waters Acquity HSS T3 1.8 μm 2.1×50 mm column. Peak detection is reported at full scan 210-450 nM. Mass spectrometry results are reported as the ratio of mass over charge.

Eluent A: Water+0.05% formic acid+3.75 mM ammonium acetate.

Eluent B: Acetonitrile+0.04% formic acid.

Flow: 1 mL/min

Gradient:

| Time [min] | % A (Eluent A) | % B (Eluent B) |
|---|---|---|
| 0.00 | 95 | 5 |
| 1.40 | 2 | 98 |
| 1.80 | 2 | 98 |
| 1.90 | 95 | 5 |
| 2.00 | 95 | 5 |

All reagents, starting materials and intermediates utilized in these Examples are available from commercial sources or are readily prepared by methods known to those skilled in the art.

Synthesis of Aminopyrimidine Derivatives

Agents of the invention may be prepared by a reaction sequence involving an alkylation of 4-amino-6-chloropyrimidin-5-ol (1) with an alkyl halide (2) using an appropriate base, Suzuki coupling with a Moronic ester (4) usind an appropriate palladium catalyst, such as bis(triphenylphosphine)palladium(II) dichloride, deprotection using an appropriate acid, such as TFA or HCl to form intermediate 6, which is reacted with an appropriate acid or acid chloride using an appropriate coupling reagent, such as T3P, and an appropriate base, such as DIPEA, or in the case of an acid chloride using a base, such as DIPEA, to yield compound 7, i.e. a compound of the invention, as shown in Scheme 1:

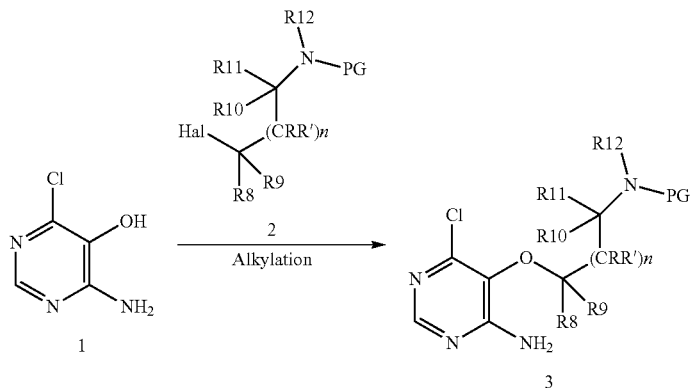

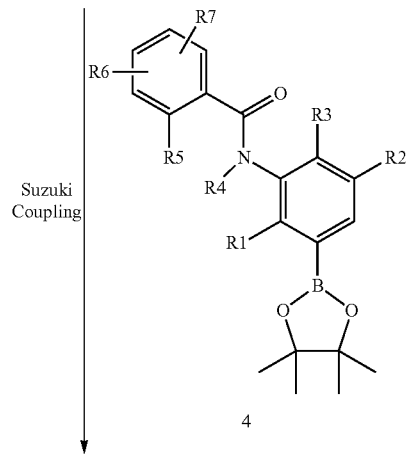

-continued

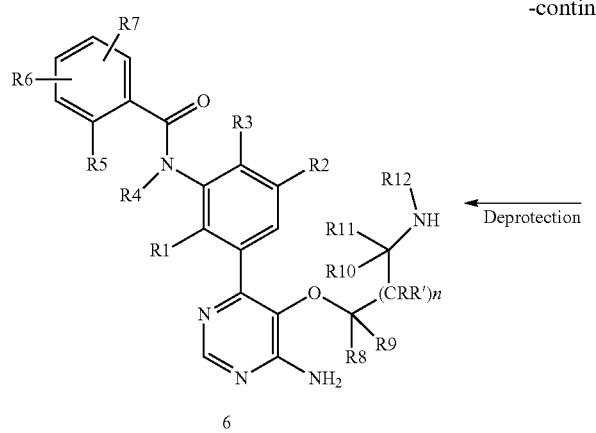

6

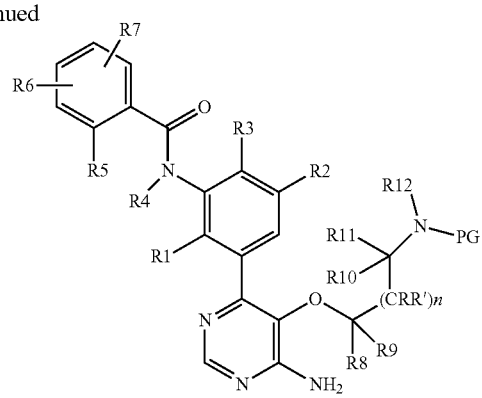

5

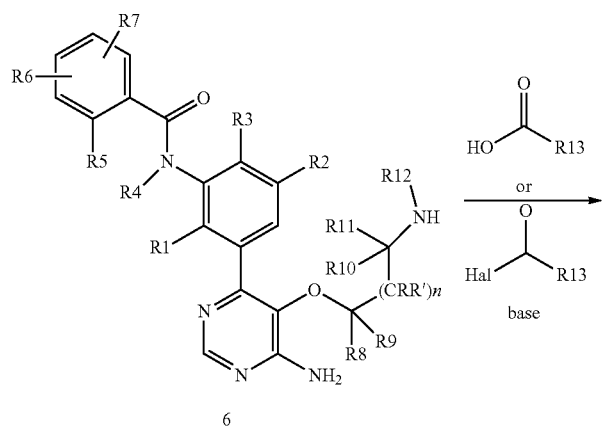

6

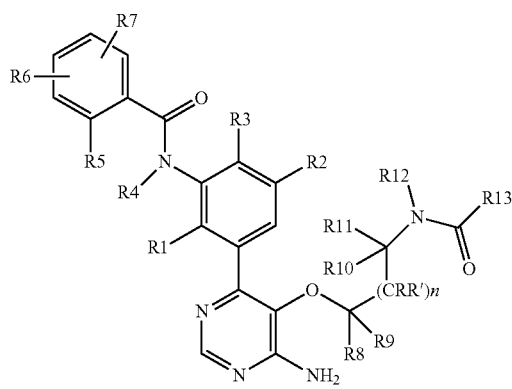

7

Example 1

N-(3-(5-((1-Acryloylazetidin-3-yl)oxy)-6-aminopyrimidin-4-yl)-5-fluoro-2-methylphenyl)-4-cyclopropyl-2-fluorobenzamide

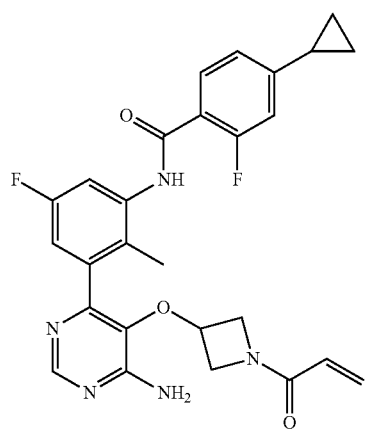 [SMILES: C=CC(=O)N1CC(Oc2c(N)ncnc2-c2cc(F)cc(NC(=O)c3ccc(C4CC4)cc3F)c2C)C1]

(1) tert-Butyl 3-((4-amino-6-chloropyrimidin-5-yl)oxy)azetidine-1-carboxylate, INT 1

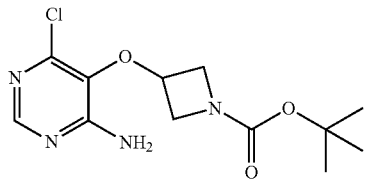 [SMILES: CC(C)(C)OC(=O)N1CC(Oc2c(N)ncnc2Cl)C1]

To a solution of N-Boc-3-iodoazetidine (6.84 g, 24.16 mmol) in DMF (37 mL) was added 4-amino-6-chloropyrimidin-5-ol (2.00 g, 13.74 mmol) followed by potassium carbonate (5.70 g, 41.24 mmol). The reaction mixture was stirred at 100° C., for 16 hr. The mixture was diluted with EtOAc and washed with saturated aqueous sodium hydrogen carbonate solution. The aqueous layer was back-extracted with EtOAc. The combined organic layers were washed with water (2×) and brine (2×), dried over magnesium sulfate, filtered and concentrated. The crude was dried in vacuum for 30 min. The residue was purified by flash chromatography (DCM/MeOH gradient, 0-5%). The isolated residue was triturated with cyclohexane. The resulting off-white solid was filtered off, rinsed with cyclohexane, and dried in vacuum to afford the title compound INT 1 as an off-white solid.

UPLC-MS: MS (ESI): [M+H]+ 301.0, rt=0.83 min. 1H NMR (DMSO-d6): δ (ppm) 7.98 (s, 1H), 7.34 (br s, 2H), 4.93-4.70 (m, 1H), 4.23-3.95 (m, 4H), 1.39 (s, 9H).

(2) 2-(5-Fluoro-2-methyl-3-nitrophenyl)-4,4,5,5-tetramethyl-1,3,2-dioxaborolane, INT 2

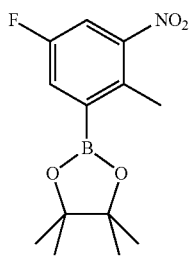 [SMILES: Cc1c(B2OC(C)(C)C(C)(C)O2)cc(F)cc1[N+](=O)[O-]]

To a mixture of 1-bromo-5-fluoro-2-methyl-3-nitro-benzene (5.0 g, 21.37 mmol) and bis(diphenylphosphino)ferrocenedichloropalladium(II) (0.78 g, 1.06 mmol) in dioxane (200 mL) was added BISPIN (8.14 g, 32.05 mmol) followed by potassium acetate (7.34 g, 74.79 mmol). The reaction mixture was stirred at 100° C. for 6 hr. After cooling the brownish mixture was diluted with water (200 mL) and extracted with EtOAc. The organic layer was washed with saturated aqueous sodium hydrogen carbonate solution and brine (2×), dried over sodium sulfate, filtered and concentrated. The residue was purified by flash chromatography (silica; cyclohexane/EtOAc 9:1) to afford INT 2 as a yellow oil.

1H NMR (DMSO-d6): δ (ppm) 7.79 (d, 1H), 7.55 (d, 1H), 2.48 (s, 3H), 1.31 (s, 12H).

(3) 5-Fluoro-2-methyl-3-(4,4,5,5-tetramethyl-1,3,2-dioxaborolan-2-yl)aniline, INT 3

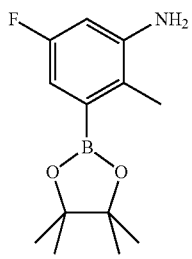

To a solution of INT 2 (12.4 g, 44.1 mmol) in EtOAc (300 mL) was added Pd/C 10% (4.0 g). The reaction mixture was hydrogenated at room temperature and normal pressure for 18 hr. The mixture was filtered over Kieselgur (Supelco) and the filtrate was concentrated. The residue was purified by flash chromatography (silica, EtOAc) to afford INT 3 as a beige solid.

MS (ESI): 252.2 [M+H]+, 1H NMR (DMSO-d6): δ (ppm) 6.52-6.46 (m, 2H), 5.13 (br s, 2H), 2.17 (s, 3H), 1.29 (s, 12H).

(4) Methyl 4-cyclopropyl-2-fluorobenzoate, INT 4

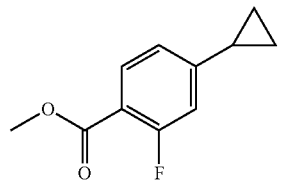

A mixture of methyl 4-bromo-2-fluorobenzoate (20.00 g, 85.82 mmol), cyclopropylboronic acid (9.68 g, 112.69 mmol) and potassium phosphate (35.70 g, 168.00 mmol) in toluene (250 mL) was degassed with argon for 5 min. Then, tricyclohexylphosphine (2.36 g, 8.41 mmol) and water (1.82 mL, 101.00 mmol) were added and the mixture was again degassed with argon for 5 min. Palladium(II) acetate (0.94 g, 4.21 mmol) was added and the reaction mixture was stirred at 100° C. overnight. The mixture was partitioned between EtOAc and water. The suspension was filtered through a pad of Celite. The phases of the filtrate were separated, the aqueous layer was back-extracted with EtOAc. The organic layers were combined, washed with saturated aqueous sodium hydrogen carbonate solution and brine, dried over magnesium sulfate, filtered and concentrated. The residue was purified by flash chromatography (cyclohexane/EtOAc gradient, 0-15%) to afford INT 4 as an orange oil. UPLC-MS: MS (ESI): [M+H]+ 195.0, rt=1.11 min. 1H NMR (CDCl3): δ (ppm) 7.83 (t, 1H), 6.90 (d, 1H), 6.79 (d, 1H), 3.92 (s, 3H), 2.00-1.96 (m, 1H), 1.15-1.03 (m, 21-1), 0.84-0.73 (m, 2H).

(5) 4-Cyclopropyl-2-fluoro-N-(5-fluoro-2-methyl-3-(4,4,5,5-tetramethyl-1,3,2-dioxaborolan-2-yl)phenyl)benzamide, INT 5

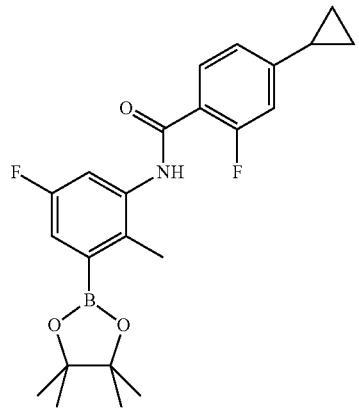 [SMILES: Cc1c(NC(=O)c2ccc(C3CC3)cc2F)cc(F)cc1B1OC(C)(C)C(C)(C)O1]

To a solution of INT 3 (5.88 g, 23.41 mmol) and INT 4 (5.00 g, 25.70 mmol) in THF (200 mL) at 0° C. was added dropwise NaHMDS solution (1 M in THF, 35.1 mL, 35.10 mmol). The reaction mixture was stirred at RT for 2 hr, then additional NaHMDS solution (1 M in THF, 5.0 mL, 5.00 mmol) was added. After stirring for another hour more NaHMDS solution (1 M in THF, 5.0 mL, 5.00 mmol) was added and the mixture was stirred for an additional 2 hr. The mixture was diluted with EtOAc and washed with saturated aqueous sodium hydrogen carbonate solution and brine. The organic layer was dried over magnesium sulfate, filtered and concentrated. The crude was suspended in EtOAc and filtered. The collected solid was washed with EtOAc and dried in vacuum to afford compound INT 5 as a beige solid.

UPLC-MS: MS (ESI): [M+H]$^+$ 414.2, rt=1.45 min. $^1$H NMR (DMSO-d$_6$): δ (ppm) 9.70 (br s, 1H), 7.62 (t, 1H), 7.51 (d, 1H), 7.19 (dd, 1H), 7.10-7.00 (m, 2H), 2.37 (s, 3H), 2.06-1.96 (m, 1H), 1.31 (s, 12H), 1.08-0.99 (m, 2H), 0.82-0.73 (m, 2H).

(6) tert-Butyl 3-((4-amino-6-(3-(4-cyclopropyl-2-fluorobenzamido)-5-fluoro-2-methylphenyl)pyrimidin-5-yl)oxy)azetidine-1-carboxylate, INT 6

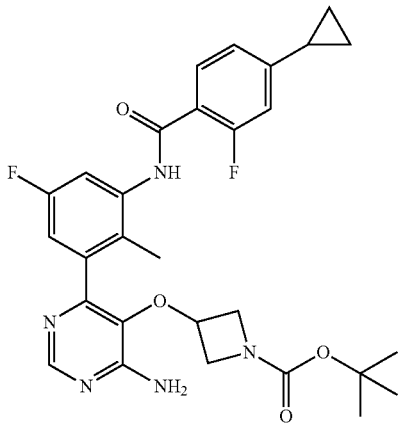 [SMILES: Cc1c(NC(=O)c2ccc(C3CC3)cc2F)cc(F)cc1-c1ncnc(N)c1OC1CN(C(=O)OC(C)(C)C)C1]

To a solution of INT 1 (500 mg, 1.66 mmol) in DME (8.4 mL) and water (1.2 mL) was added INT 5 (756 mg, 1.83 mmol) followed by aqueous sodium carbonate solution (1 M, 4.99 mL, 4.99 mmol). The mixture was degassed with argon for 10 min, then bis(triphenylphosphine)palladium(II) dichloride (58.3 mg, 0.083 mmol) was added. The reaction mixture was stirred for 10 min at 110° C. in a microwave reactor. More INT 5 (137 mg, 0.33 mmol) was added. The reaction mixture was stirred at 110° C. for an additional 10 min in a microwave reactor. The mixture was partitioned between EtOAc and saturated aqueous sodium hydrogen carbonate solution. The solid was filtered off, washed with water and EtOAc, and dried in vacuum to afford compound INT 6 as an off-white solid. The mother liquor of the filtration was transferred in an extraction funnel and the layers were separated. The aqueous layer was back-extracted with EtOAc. The combined organic layers were washed with brine, dried over magnesium sulfate, filtered and concentrated. The residue was purified by flash chromatography (silica; DCM/EtOAc gradient, 0-100%) to afford more INT 6 as an off-white solid.

UPLC-MS: MS (ESI): [M+H]$^+$ 552.3, rt=1.15 min. $^1$H NMR (DMSO-d$_6$): δ (ppm) 9.86 (s, 1H), 8.19 (s, 1H), 7.66 (t, 1H), 7.58 (d, 1H), 7.21-6.91 (m, 5H), 4.31-4.16 (m, 1H), 3.77-3.46 (m, 4H), 2.08-1.99 (overlapping s, 3H and m, 1H), 1.31 (s, 9H), 1.12-0.98 (m, 2H), 0.87-0.73 (m, 2H).

(7) N-(3-(6-Amino-5-(azetidin-3-yloxy)pyrimidin-4-yl)-5-fluoro-2-methylphenyl)-4-cyclopropyl-2-fluorobenzamide, INT 7

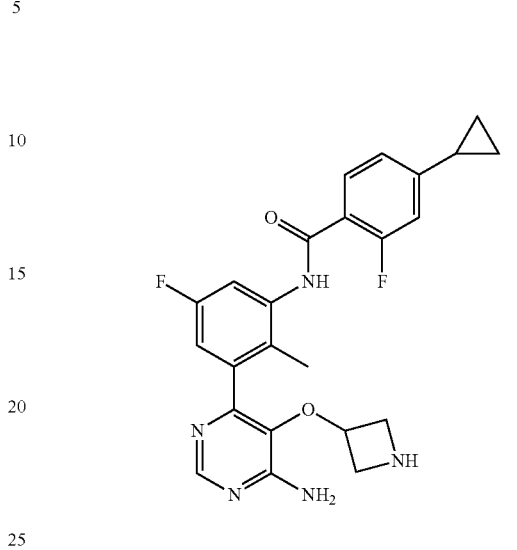

To a solution of INT 6 (100 mg, 0.18 mmol) in DCM (2.0 mL) was added TFA (0.210 mL, 2.72 mmol) dropwise. The reaction mixture was stirred at RT overnight. The mixture was concentrated and the residue was dried in vacuum to afford crude INT 7 as the TFA salt as a brown oil.

UPLC-MS: MS (ESI): [M+H]$^+$ 452.3, rt=0.73 min. $^1$H NMR (DMSO-d$_6$): δ (ppm) 10.04 (s, 1H), 8.84 (s, br, 2H), 8.63 (s, 1H), 8.56 (s, br, 2H), 7.73-7.61 (m, 2H), 7.32-7.24 (m, 1H), 7.14-7.03 (m, 2H), 4.54-45 (m, 1H), 3.92-3.46 (m, br, 4H), 2.10-2.01 (overlapping s, 3H and m, 1H), 1.12-1.03 (m, 2H), 0.83-0.77 (m 2H).

(8) N-(3-(5-((1-Acryloylazetidin-3-yl)oxy)-6-aminopyrimidin-4-yl)-5-fluoro-2-methylphenyl)-4-cyclopropyl-2-fluorobenzamide To a solution of acrylic acid (73 mg, 1.02 mmol) in DMF (1.5 mL) was added DIPEA (0.47 mL, 2.71 mmol) followed by T3P solution (50% in DMF) (0.51 mL, 0.88 mmol). The mixture was stirred at RT for 20 min. To a solution of INT 7 (containing 2.5 eq TFA) (499 mg, 0.68 mmol) and DIPEA (0.36 mL, 2.03 mmol) in DMF (5.3 mL) at 0° C. was added dropwise the above solution. The reaction mixture was stirred at 0° C. for 90 min. The mixture was diluted with EtOAc and washed with saturated aqueous sodium hydrogen carbonate solution. The aqueous layer was back-extracted with EtOAc. The combined organic layers were washed with water and brine (2×), dried over magnesium sulfate, filtered and concentrated. The residue was purified by flash chromatography (silica; DCM/(MeOH with 2% aqueous ammonium hydroxide) gradient, 0-10%) to afford the title compound. Example 1 as a white solid after trituration with diethyl ether.

UPLC-MS: MS (ESI): [M+H]$^+$ 506.2, rt=0.93 min. $^1$H NMR (DMSO-d$_6$): δ (ppm) 9.89 (s, 1H), 8.2 (s, 1H), 7.66 (t, 1H), 7.54 (d, 1H), 7.2-7.0 (m, 5H), 6.15 (dd, 1H), 6.02 (dd, 1H), 5.61 (dd, 1H), 4.37-4.29 (m, 1H), 4.11-3.95 (m, 2H), 3.8-3.66 (m, 2H), 2.08-1.99 (overlapping s, 3H and m, 1H), 1.08-1.02 (m, 2H), 0.83-0.76 (m, 2H).

Example 2

(E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide

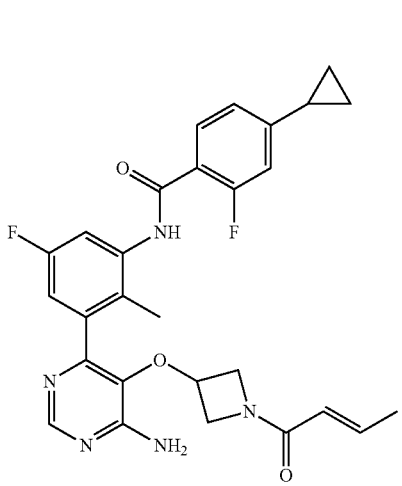 [SMILES: C/C=C/C(=O)N1CC(Oc2c(N)ncnc2-c2cc(F)cc(NC(=O)c3ccc(C4CC4)cc3F)c2C)C1]

The title compound was prepared according to Scheme 1 following a procedure analogous to Example 1 replacing acrylic acid with (E)-but-2-enoic acid in step 8.
UPLC-MS: MS (ESI): [M+H]$^+$ 520.2, rt=0.97 min.

Example 3

N-(3-(6-Amino-5-((1-propioloylazetidin-3-yl)oxy)pyrimidin-4-yl)-5-fluoro-2-methylphenyl)-4-cyclopropyl-2-fluorobenzamide

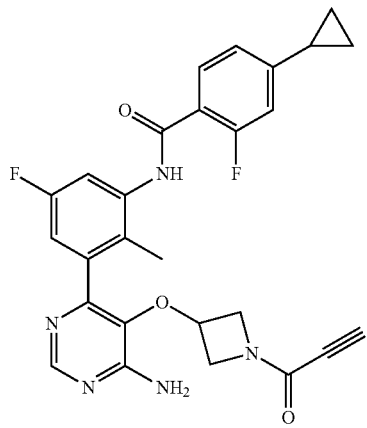 [SMILES: C#CC(=O)N1CC(Oc2c(N)ncnc2-c2cc(F)cc(NC(=O)c3ccc(C4CC4)cc3F)c2C)C1]

The title compound was prepared according to Scheme 1 following a procedure analogous to Example 1 replacing acrylic acid with propiolic acid in step 8.
UPLC-MS: MS (ESI): [M+H]$^+$ 504.2, rt=0.95 min.

Example 4

N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide

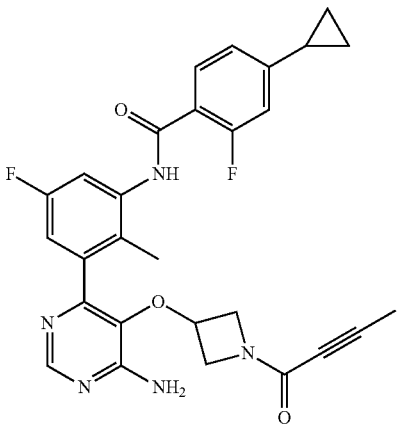 [SMILES: CC#CC(=O)N1CC(Oc2c(N)ncnc2-c2cc(F)cc(NC(=O)c3ccc(C4CC4)cc3F)c2C)C1]

The title compound was prepared according to Scheme 1 following a procedure analogous to Example 1 replacing acrylic acid with 2-butynoic acid in step 8. UPLC-MS: MS (ESI): [M+H]$^+$ 518.2, rt=0.97 min.

Example 5

N-(3-(5-((1-Acryloylpiperidin-4-yl)oxy)-6-aminopyrimidin-4-yl)-5-fluoro-2-methylphenyl)-4-cyclopropyl-2-fluorobenzamide

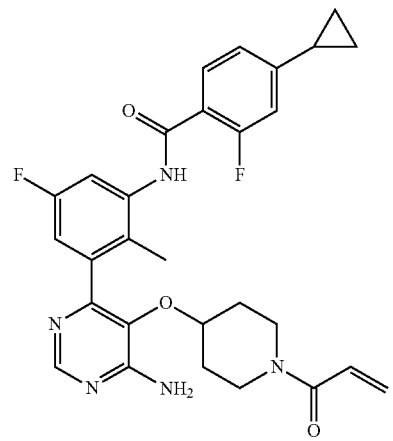 [SMILES: C=CC(=O)N1CCC(Oc2c(N)ncnc2-c2cc(F)cc(NC(=O)c3ccc(C4CC4)cc3F)c2C)CC1]

The title compound was prepared according to Scheme 1 following a procedure analogous to Example 1 replacing N-Boc-3-iodoazetidine with N-Boc-4-bromopiperidine in step 1.
UPLC-MS: MS (ESI): [M+H]$^+$ 534.2, rt=0.94 min.

Alternatively, agents of the invention may be prepared by a reaction sequence involving Mitsunobu reaction of 4-amino-6-chloropyrimidin-5-ol with an alcohol of formula 2' using an appropriate azodicarboxylate, such as DIAD, and Smopex-301 or triphenylphosphine; thereupon the reaction sequences of scheme 1 are being carried out, i.e. the Suzuki coupling with a boronic ester using an appropriate catalyst, such as bis(triphenyl-phosphine)-palladium(II) dichloride, deprotection using an appropriate acid, such as TFA or HCl, followed by amide formation of the ammonium salt or the free amine with an acid and using an appropriate coupling reagent, such as T3P, and an appropriate base, such as DIPEA, or with an acid chloride using an appropriate base, such as DIPEA, to yield a compound of the invention, i.e. a compound of formula 7, as shown in Scheme 2 below:

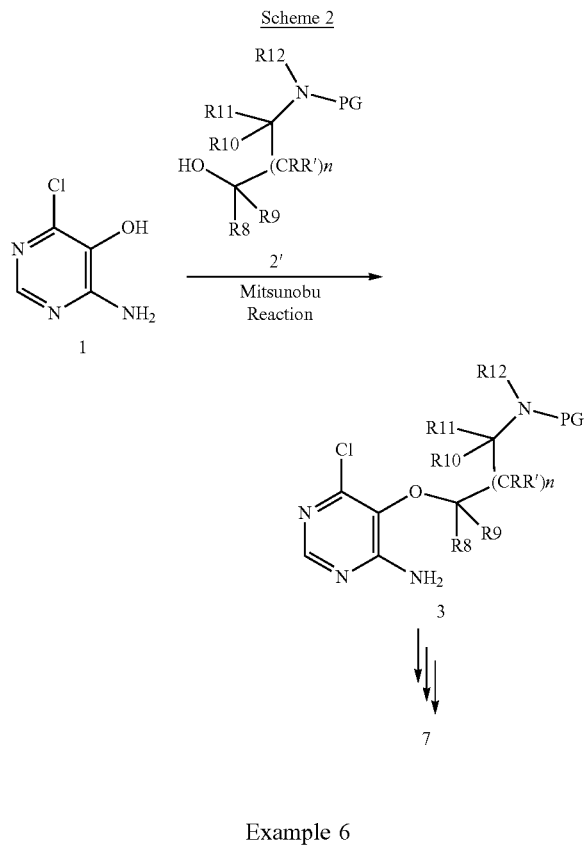

Example 6

N-(3-(6-Amino-5-(2-(N-methylacrylamido)ethoxy)pyrimidin-4-yl)-5-fluoro-2-methylphenyl)-4-cyclopropyl-2-fluorobenzamide

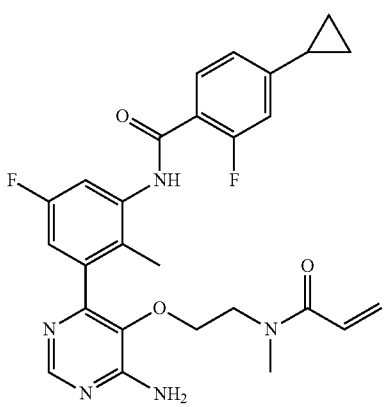 [SMILES: C=CC(=O)N(C)CCOc1c(N)ncnc1-c1cc(F)cc(NC(=O)c2ccc(C3CC3)cc2F)c1C]

(1) tert-Butyl (2-((4-amino-6-chloropyrimidin-5-yl)oxy)ethyl)(methyl)carbamate, INT 8

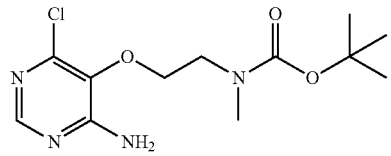 [SMILES: CN(CCOc1c(N)ncnc1Cl)C(=O)OC(C)(C)C]

To a solution of 4-amino-6-chloropyrimidin-5-ol (content 90%, 2.00 g, 12.37 mmol) in THF (120 mL) was added N-Boc-N-methyl-2-hydroxyethylamine (6.07 g, 34.64 mmol) followed by SMOPEX-301 (1 mmol/g, 30.90 g, 30.90 mmol). Then, a solution of DIAD (6.01 mL, 30.52 mmol) in THF (20 mL) was added slowly. The reaction mixture was stirred at 60° C. for 3 hr. The mixture was filtered through a pad of Celite. The filtrate was concentrated to afford an oil which was triturated with EtOAc and a white precipitate was formed. The solid was filtered off to afford INT 8. The mother liquor was concentrated and the residue was purified by flash chromatography (silica; DCM/EtOAc gradient, 0-100%) to afford more INT 8 as a beige solid.

UPLC-MS: MS (ESI): $[M+H]^+$ 303.1, rt=0.86 min. $^1$H NMR (DMSO-$d_6$): δ (ppm) 7.97 (s, 1H), 7.26 (s, br, 2H), 4.02-3.93 (m, 2H), 3.54 (t, 2H), 2.89 (s, br, 3H), 1.39 (s, 9H).

(2) tert-Butyl (2-((4-amino-6-(3-(4-cyclopropyl-2-fluorobenzamido)-5-fluoro-2-methylphenyl)pyrimidin-5-yl)oxy)ethyl)(methyl)carbamate, INT 9

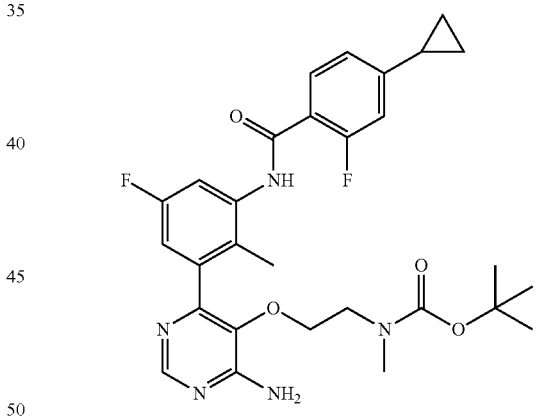

To a solution of INT 8 (447 mg, 1.48 mmol) in DME (7.0 mL) and water (1.0 mL) was added INT 5 (638 mg, 1.54 mmol) followed by aqueous sodium carbonate solution (1 M, 4.21 mL, 4.21 mmol). The mixture was degassed with argon for 10 min and bis(triphenylphosphine)palladium(II) dichloride (49.2 mg, 0.070 mmol) was added. The reaction mixture was stirred at 110° C. for 10 min in a microwave reactor. More INT 5 (232 mg, 0.56 mmol) was added and the reaction mixture was stirred at 110° C. for an additional 15 min in a microwave reactor. The mixture was partitioned between saturated aqueous sodium hydrogen carbonate solution and EtOAc. The organic layer was washed with water and brine, dried over magnesium sulfate, filtered and concentrated. The residue was purified by flash chromatography (silica; DCM/EtOAc gradient, 0-100%) to afford INT 9 as an off-white solid.

UPLC-MS: MS (ESI): [M+H]⁺ 554.3, rt=1.21 min. ¹H NMR (DMSO-d₆): δ (ppm) rotamers 9.76 (s, 1H), 8.19 (s, 1H), 7.74-7.53 (m, 2H) 7.20-6.85 (m, 5H), 3.57-3.48 (m, 2H), 3.29-3.15 (m, 2H), 2.58 (s, 3H), 2.08-1.99 (overlapping s, 3H and m, 1H), 1.34 and 1.28 (s, 9H), 1.10-1.02 (m, 2H), 0.84-0.77 (m, 2H).

(3) N-(3-(6-Amino-5-(2-(methylamino)ethoxy)pyrimidin-4-yl)-5-fluoro-2-methylphenyl)-4-cyclopropyl-2-fluorobenzamide, INT 10

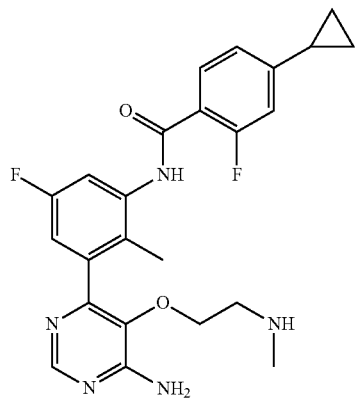 [SMILES: CNCCOc1c(N)ncnc1-c1cc(F)cc(NC(=O)c2ccc(C3CC3)cc2F)c1C]

To a solution of INT 9 (335 mg, 0.61 mmol) in DCM (5.0 mL) was added TFA (0.47 mL, 6.05 mmol). The reaction mixture was stirred at RT for 15 hr. The mixture was concentrated under reduced pressure. The residue was dried in vacuum to afford INT 10 as the TFA salt as a brown oil.

UPLC-MS: MS (ESI): [M+H]⁺ 454.3, rt=0.73 min. ¹H NMR (DMSO-d₆): δ (ppm) 10.02 (s, 1H), 9.07-8.13 (s, v br, number of H cannot be assigned), 8.58 (s, 1H), 8.51 (s, br, 2H), 7.71-7.61 (m, 2H), 7.29-7.22 (m, 1H), 7.14-7.05 (m, 2H), 3.75-3.65 (m, 2H), 3.16-3.07 (m, 2H), 2.48 (s, 3H, overlapping with solvent peak), 2.12 (s, 3H), 2.10-1.99 (m, 1H), 1.11-1.03 (m, 2H), 0.83-0.76 (m, 2H).

(4) N-(3-(6-Amino-5-(2-(N-methylacrylamido)ethoxy)pyrimidin-4-yl)-5-fluoro-2-methylphenyl)-4-cyclopropyl-2-fluorobenzamide To a solution of acrylic acid (62 mg, 0.87 mmol) in DMF (4.0 mL) was added DIPEA (0.302 mL, 1.73 mmol) followed by T3P solution (50% in DMF) (0.438 mL, 0.750 mmol). The mixture was stirred at RT for 30 min. To a solution of INT 10 (containing 3.0 eq TFA, content 90%, 510 mg, 0.577 mmol) and DIPEA (0.302 mL, 1.731 mmol) in DMF (2.0 mL) at 0° C. was added dropwise the above solution. The reaction mixture was stirred at 0° C. for 30 min. The mixture was diluted with water and extracted with EtOAc. The organic layer was washed with water (2×) and brine (2×), dried over magnesium sulfate, filtered and concentrated. The residue was purified by flash chromatography (silica; DCM/(MeOH with 2% aqueous ammonium hydroxide) gradient, 0-9%) to afford the title compound Example 6 as a white solid.

UPLC-MS: MS (ESI): [M+H]⁺ 508.3, rt=0.95 min. ¹H NMR (DMSO-d₆): δ (ppm) rotamers 9.77 and 9.56 (s, total 1H), 8.25-8.14 (m, 1H), 7.79-7.50 (m, 2H), 7.17-6.93 (m, 5H), 6.70-6.55 (m, 1H), 6.06 (t, 1H), 5.59 (d, 1H), 3.63-3.40 (m, 4H), 2.80 and 2.49 (s, total 3H, peak at 2.49 overlapping with solvent peak), 2.09-1.93 (m, 4H), 1.11-1.00 (m, 2H), 0.85-0.76 (m, 2H).

Example 7

(E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide

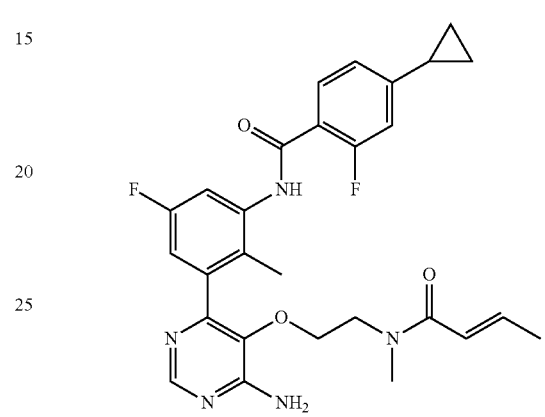

The title compound was prepared according to Scheme 2 following a procedure analogous to Example 6 replacing acrylic acid with (E)-but-2-enoic acid in step 4.

UPLC-MS: MS (ESI): [M+H]⁺ 522.2, rt=0.97 min.

Example 8

N-(3-(6-Amino-5-(2-(N-methylpropiolamido)ethoxy)pyrimidin-4-yl)-5-fluoro-2-methylphenyl)-4-cyclopropyl-2-fluorobenzamide

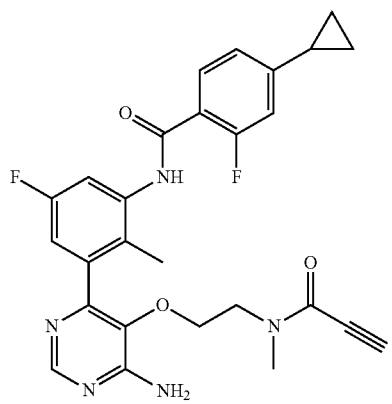

The title compound was prepared according to Scheme 2 following a procedure analogous to Example 6 replacing acrylic acid with propiolic acid in step 4.

UPLC-MS: MS (ESI): [M+H]⁺ 506.3, rt=0.95 min.

Example 9

(E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide

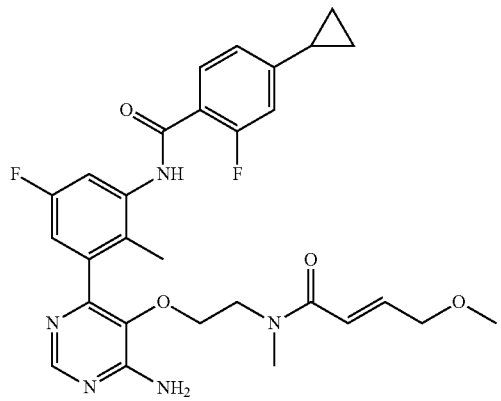 [SMILES: COC/C=C/C(=O)N(C)CCOc1c(N)ncnc1-c1cc(F)cc(NC(=O)c2ccc(C3CC3)cc2F)c1C]

(1) N-(3-(6-Amino-5-(2-(methylamino)ethoxy)pyrimidin-4-yl)-5-fluoro-2-methylphenyl)-4-cyclopropyl-2-fluorobenzamide, INT 11

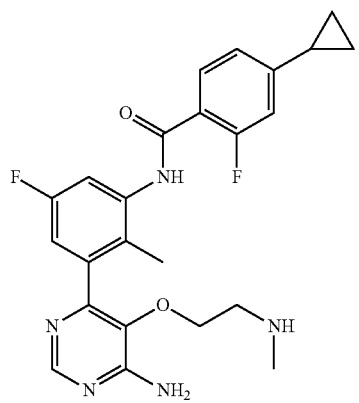 [SMILES: CNCCOc1c(N)ncnc1-c1cc(F)cc(NC(=O)c2ccc(C3CC3)cc2F)c1C]

To a solution of INT 9 (2.50 g, 4.52 mmol) in DCM (30 mL) was added HCl (2 M in diethyl ether, 20.0 mL, 40.00 mmol). The reaction mixture was stirred at RT for 4 hr. The mixture was concentrated under reduced pressure and the residue was dried in vacuum to afford INT 11 as the hydrochloride salt as a white solid.

UPLC-MS: MS (ESI): [M+H]$^+$ 454.2, rt=0.70 min. $^1$H NMR (MeOD-d$_3$): δ (ppm) 8.60 (s, 1H), 7.82 (t, 1H), 7.69-7.62 (m, 1H), 7.41-7.36 (m, 1H), 7.10 (d, 1H), 7.02 (d, 1H), 4.10-3.80 (m, br, 2H), 3.39-3.20 (m, 2H), 2.70 (s, 3H), 2.26 (s, 3H), 2.11-1.99 (m, 1H), 1.19-1.07 (m, 2H), 0.89-0.77 (m, 2H).

(2) (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide The title compound was prepared following a procedure analogous to step 4 of Example 6 replacing INT 10 with INT 11 (hydrochloride salt) and replacing acrylic acid with (E)-4-methoxy-but-2-enoic acid.

UPLC-MS: MS (ESI): [M+H]$^+$ 552.2, rt=0.93 min.

Example 10

N-(3-(6-Amino-5-(2-(N-methylbut-2-ynamido)ethoxy)pyrimidin-4-yl)-5-fluoro-2-methylphenyl)-4-cyclopropyl-2-fluorobenzamide

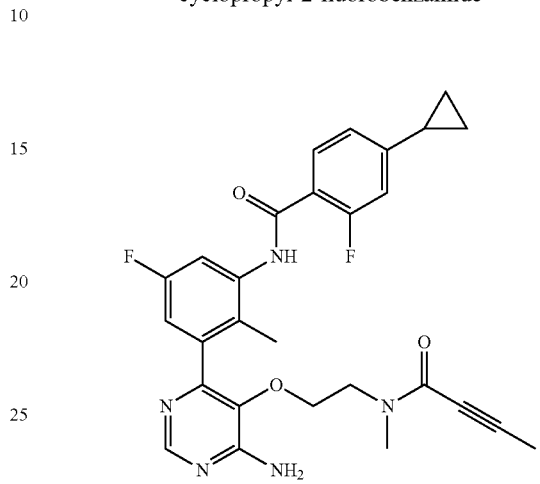

The title compound was prepared according to Scheme 2 following a procedure analogous to Example 6 replacing acrylic acid with 2-butynoic acid in step 4.

UPLC-MS: MS (ESI): [M+H]$^+$ 520.2, rt=0.96 min.

Example 11

N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide

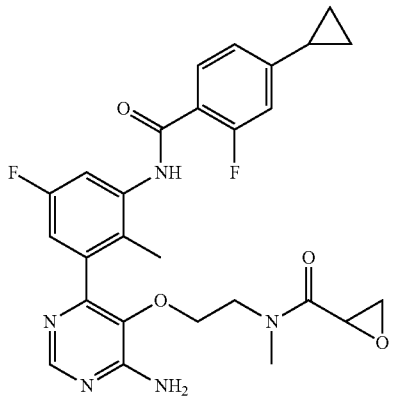 [SMILES: Cc1c(NC(=O)c2ccc(C3CC3)cc2F)cc(F)cc1-c1ncnc(N)c1OCCN(C)C(=O)C1CO1]

To a solution of TBHP (5.5 M in decane, 0.079 mL, 0.434 mmol) in THF (2.0 mL) at −78° C. was added n-butyl lithium (2.5 M in hexane, 0.145 mL, 0.362 mmol). The mixture was stirred at −78° C. for 10 min. Then, a solution of Example 6 (147 mg, 0.290 mmol) in THF (1.0 mL) was added and the reaction mixture was stirred at RT for 5 hr. The mixture was diluted with water and extracted with EtOAc. The organic layer was washed with water and brine, dried over magnesium sulfate, filtered and concentrated. The residue was purified by preparative HPLC (Xterra 150, water/acetonitrile gradient) to afford Example 11 as a white solid after lyophilization.

UPLC-MS: MS (ESI): [M+H]⁺ 524.4, rt=0.88 min. ¹H NMR (DMSO-d₆): δ (ppm) rotamers 9.83 and 9.58 (s, total 1H), 8.26-8.15 (m, 1H), 7.78-7.61 (m, 1H), 7.61-7.48 (m, 1H), 7.22-6.90 (m, 5H), 3.84-3.39 (m, 5H), 2.89 (s, 1.2H), 2.87-2.76 (m, 1H), 2.71-2.61 (m, 1H), 2.44 (s, 1.8H, overlapping with solvent peak), 2.10-1.93 (m, 4H), 1.12-0.99 (m, 2H), 0.87-0.74 (m, 2H).

Example 12

N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide

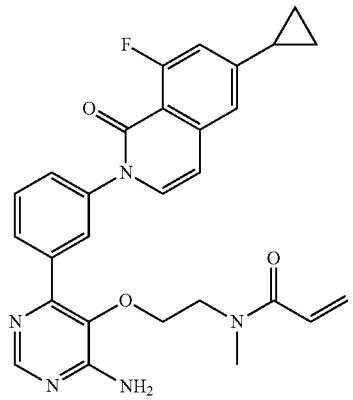 [SMILES: C=CC(=O)N(C)CCOc1c(N)ncnc1-c1cccc(-n2ccc3cc(C4CC4)cc(F)c3c2=O)c1]

(1) 2-(3-Chlorophenyl)-6-cyclopropyl-8-fluoroisoquinolin-1(2H)-one, INT 12

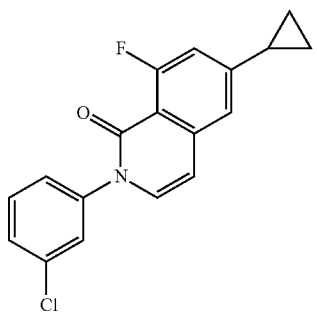 [SMILES: O=c1c2c(F)cc(C3CC3)cc2ccn1-c1cccc(Cl)c1]

A mixture of 1-chloro-3-iodobenzene (0.439 ml, 3.54 mmol), 6-cyclopropyl-8-fluoro-isoquinolin-1(2H)-one (600 mg, 2.95 mmol), ethyl 2-oxocyclohexanecarboxylate (0.094 mL, 0.591 mmol) and cesium carbonate (2020 mg, 6.20 mind) in DMSO (15 mL) was degassed with argon for 5 min. Copper(I) iodide (112 mg, 0.59 mmol) was added, the reaction flask was sealed, the mixture stirred at 120° C. for 16 hr. The mixture was cooled to RT and diluted with EtOAc (100 mL). The resulting slurry was filtered over Hyflo and the filter cake was washed with EtOAc. The filtrate was concentrated and the residue was purified by flash chromatography (silica; cyclohexane/EtOAc gradient, 5-40%) to afford INT 12 as a yellow solid.

UPLC-MS: MS (ESI): [M+H]⁺ 314.1, rt=1.25 min. ¹H NMR (DMSO-d₆): δ (ppm) 7.61 (s, 1H), 7.59-7.50 (m, 2H), 7.48-7.40 (m, 2H), 7.26 (s, 1H), 6.99 (d, 1H), 6.60 (d, 1H), 2.12-2.02 (m, 1H), 1.14-1.05 (m, 2H), 0.92-0.83 (m, 2H).

(2) 6-Cyclopropyl-8-fluoro-2-(3-(4,4,5,5-tetramethyl-1,3,2-dioxaborolan-2-yl)phenyl)isoquinolin-1(2H)-one, INT 13

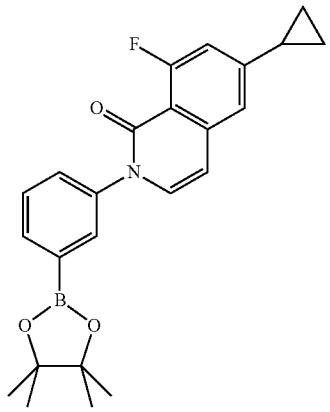 [SMILES: CC1(C)OB(c2cccc(-n3ccc4cc(C5CC5)cc(F)c4c3=O)c2)OC1(C)C]

A mixture of INT 12 (808 mg, 2.58 mmol), BISPIN (981 mg, 3.86 mmol), X-Phos (123 mg, 0.26 mmol) and potassium acetate (758 mg, 7.73 mmol) in dioxane (13 mL) was degassed under argon for 5 min. Tris(dibenzylideneacetone)dipalladium(0) (118 mg, 0.13 mmol) was added and the reaction flask was sealed. The reaction mixture was stirred at 105° C. for 2 hr. The mixture was cooled to RT, filtered over Hyflo and the filter cake was washed with EtOAc. Triphenylphosphine (169 mg, 0.64 mmol) was added to the filtrate. The filtrate was concentrated and the residue was purified by flash chromatography (silica; cyclohexane/EtOAc gradient, 5-40%). The residue was triturated with a mixture of diethyl ether and pentane (1:1) and filtered. The filter cake was washed with pentane and dried in vacuum to afford INT 13 as a white solid.

UPLC-MS: MS (ESI): [M+H]⁺ 406.3, rt 1.40 min. ¹H NMR (DMSO-d₆): δ (ppm) 7.75-7.70 (m, 1H), 7.64 (s, 1H), 7.59-7.54 (m, 2H), 7.44 (d, 1H), 7.25 (s, 1H), 6.98 (d, 1H), 6.59 (d, 1H), 2.11-2.02 (m, 1H), 1.31 (s, 12H), 1.13-1.06 (m, 2H), 0.91-0.84 (m, 2H).

(3) 2-(3-(6-Amino-5-(2-(methylamino)ethoxy)pyrimidin-4-yl)phenyl)-6-cyclopropyl-8-fluoroisoquinolin-1(2H)-one, INT 14

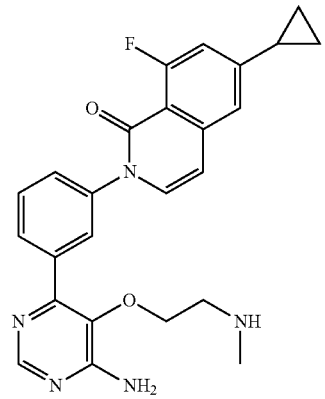 [SMILES: CNCCOc1c(N)ncnc1-c1cccc(-n2ccc3cc(C4CC4)cc(F)c3c2=O)c1]

Intermediate INT 14 was prepared according to Scheme 2 following a procedure analogous to steps 2 and 3 of Example 6 replacing INT 5 with INT 13 in step 2, and by doing a basic work-up in step 3 to afford INT 14 as the free amine.

UPLC-MS: MS (ESI): [M+H]+ 446.3, rt 0.71 min. $^1$H NMR (DMSO-d$_6$): δ (ppm) 8.21 (s, 1H), 8.13-8.02 (m, 2H), 7.63 (t, 1H), 7.51 (t, 2H), 7.45-7.31 (m, 2H), 7.27 (s, 1H), 6.99 (d, 1H), 6.62 (d, 1H), 3.73-3.64 (m, 2H), 2.73-2.64 (m, 2H), 2.23 (s, 3H), 2.12-2.03 (m, 1H), 1.14-1.06 (m, 2H), 0.92-0.83 (m, 2H).

(4) N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide To a solution of INT 14 (73 mg, 0.16 mmol) and DIPEA (860, 0.492 mmol) in THF (1.6 mL) at −20° C. was added acryloyl chloride (14 μl, 0.172 mmol). The reaction mixture was stirred at −20° C. for 10 min. The mixture was diluted with aqueous sodium carbonate solution (2 M) and water and extracted with DCM (3×). The combined organic layers were dried over sodium sulfate, filtered and concentrated. The residue was purified by SFC to afford. Example 12 as a white solid.

UPLC-MS: MS (ESI): [M+H]+500.4, rt=0.93 min. $^1$H NMR (DMSO-d$_6$): δ (ppm) rotamers 8.26-8.18 (m, 1H), 8.04-7.87 (m, 2H), 7.64-7.43 (m, 3H), 7.27 (s, 1H), 7.16-7.03 (m, 2H), 7.03-6.95 (m, 1H), 6.85 and 6.69 (dd, total 1H), 6.65-6.58 (m, 1H), 6.09 (d, 1H), 5.60 (t, 1H), 3.84-3.72 (m, 2H), 3.71-3.60 (m, 2H), 3.04 and 2.76 (s, total 31-1), 2.13-2.02 (m, 1H), 1.16-1.05 (m, 2H), 0.93-0.83 (m, 2H).

Example 13

N-(3-(5-(2-Acrylamidoethoxy)-6-aminopyrimidin-4-yl)-5-fluoro-2-methylphenyl)-4-cyclopropyl-2-fluorobenzamide

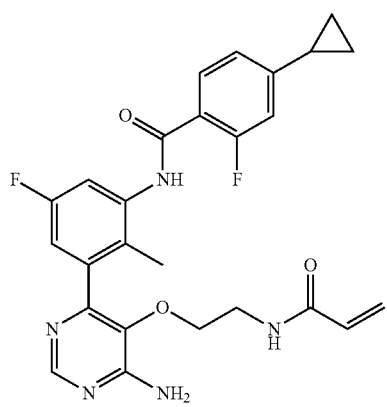

The title compound was prepared according to Scheme 2 following a procedure analogous to Example 6 replacing N-Boc-N-methyl-2-hydroxyethylamine with N-Boc-2-hydroxyethylamine in step 1.

UPLC-MS: MS (ESI): [M+H]+ 494.2, rt=0.91 min.

Example 14

N-(3-(6-Amino-5-(2-(N-ethylacrylamido)ethoxy)pyrimidin-4-yl)-5-fluoro-2-methylphenyl)-4-cyclopropyl-2-fluorobenzamide

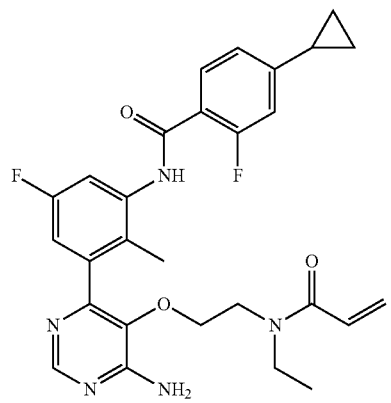 [SMILES: C=CC(=O)N(CC)CCOc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with N-Boc-N-ethyl-2-hydroxyethylamine in step 1.

UPLC-MS: MS (ESI): [M+H]+ 522.4, rt=0.99 min.

Example 15

N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide

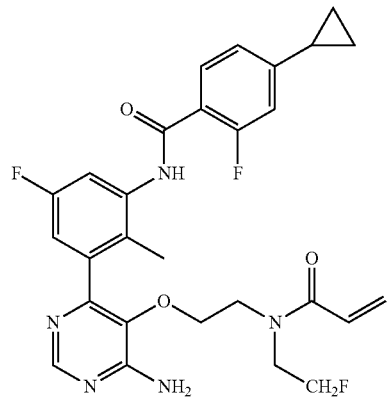

(1) tert-Butyl (2-(benzyloxy)ethyl)(2-fluoroethyl)carbamate, INT 15

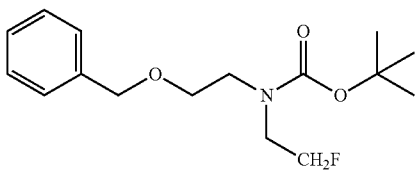

To a solution of 2-fluoroethanamine hydrochloride (4.35 g, 43.71 mmol) and 2-(benzyloxy)-acetaldehyde (6.04 g, 5.65 mL, 40.22 mmol) in MeOH (70 mL) was added sodium triacetoxyborohydride (10.44 g, 49.26 mmol), The reaction mixture was stirred at RT for 4 hr. The mixture was concentrated. The residue was taken up in EtOAc and washed with saturated aqueous sodium hydrogen carbonate solution, water and brine. The organic layer was dried over magnesium sulfate, filtered and concentrated. The residue was taken up in aqueous NaOH solution (2 M, 175 mL, 350 mmol) and di-tert butyl dicarbonate (17.65 g, 80.87 mmol) was added. The reaction mixture was stirred at RT overnight. The mixture was diluted with water and EtOAc. The layers were separated. The aqueous layer was back-extracted with EtOAc. The combined organic layers were washed with water and brine, dried over magnesium sulfate, filtered and concentrated. The residue was purified by flash chromatography (silica, cyclohexane/EtOAc gradient, 0-10%) to afford INT 15 as a pale colorless oil.

MS (ESI): [M+H]$^+$ 298.3. $^1$H NMR (DMSO-d$_6$): δ (ppm) 7.41-7.24 (m, 5H), 4.59-4.39 (m, 4H), 3.59-3.45 (m, 4H), 3.44-3.36 (m, 2H), 1.46-1.31 (m, 9H).

(2) N-Boc-N-(2-fluoroethyl)-2-hydroxyethylamine, INT 16

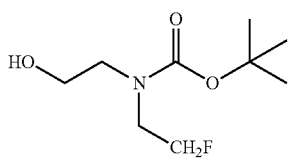

To a solution of INT 15 (3.40 g, 11.43 mmol) in THF (115 mL) was added Pd—C 10% (340 mg). The reaction mixture was hydrogenated at RT and normal pressure for 7 hr. Pd—C 10% (340 mg) was added, and the reaction mixture was hydrogenated at RT and normal pressure overnight. More Pd—C 10% (340 mg) was added, and the reaction mixture was hydrogenated at RT and normal pressure for an additional 4 hr. The mixture was diluted with DCM, filtered over a pad of Celite and concentrated to afford crude INT 16 as a colorless oil.

MS (ESI): [M+H]$^+$ 208.2. $^1$H NMR (DMSO-d$_6$): δ (ppm) 4.70-4.63 (m, 1H), 4.54 (t, 1H), 4.42 (t, 1H), 3.53 (t, 1H), 3.46 (t, 3H), 3.28-3.21 (m, 2H), 1.39 (s, 9H).

(3) N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide The title compound was prepared according to Scheme 2 following a procedure analogous to Example 6 replacing N-Boc-N-methyl-2-hydroxyethylamine with INT 16 in step 1.

UPLC-MS: MS (ESI): [M+H]$^+$ 540.3, rt=0.96 min.

Example 16

N-(3-(5-((1-Acrylamidocyclopropyl)methoxy)-6-aminopyrimidin-4-yl)-5-fluoro-2-methylphenyl)-4-cyclopropyl-2-fluorobenzamide

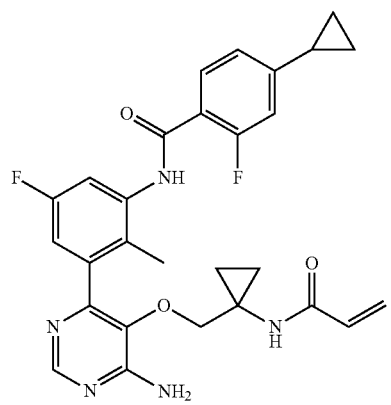 [SMILES: C=CC(=O)NC1(COc2c(N)ncnc2-c2cc(F)cc(NC(=O)c3ccc(C4CC4)cc3F)c2C)CC1]

(1) N-Boc-1-(hydroxymethyl)-cyclopropylamine, INT 17

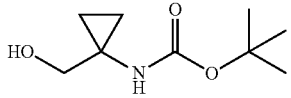

To a solution of methyl 1-((tert-butoxycarbonyl)amino) cyclopropanecarboxylate (9.30 g, 43.20 mmol) in THF (45 mL) was added lithium borohydride solution (2 M in THF, 40.0 mL, 80.00 mmol). The reaction mixture was stirred at RT overnight. The mixture was cooled to 0° C. and quenched carefully with water. The mixture was extracted with diethyl ether (2x). The combined organic layers were washed with water and brine, dried over magnesium sulfate, filtered and concentrated to afford crude INT 17 as a white solid.

MS (ESI): [M+H]$^+$ 188.2. $^1$H NMR (DMSO-d$_6$): δ (ppm) 7.03 (s, 1H), 4.55 (t, 1H), 3.38 (d, 2H), 1.37 (s, 9H), 0.63-0.50 (m, 4H).

(2) N-(3-(5-((1-Acrylamidocyclopropyl)methoxy)-6-aminopyrimidin-4-yl)-5-fluoro-2-methylphenyl)-4-cyclopropyl-2-fluorobenzamide The title compound was prepared according to Scheme 2 following a procedure analogous to Example 6 replacing. N-Boo-N-methyl-2-hydroxyethylamine with INT 17 in step 1.

UPLC-MS: MS (ESI): [M+H]$^+$ 520.4, rt=0.95 min.

Example 17

(S)—N-(3-(5-(2-Acrylamidopropoxy)-6-aminopyrimidin-4-yl)-5-fluoro-2-methylphenyl)-4-cyclopropyl-2-fluorobenzamide

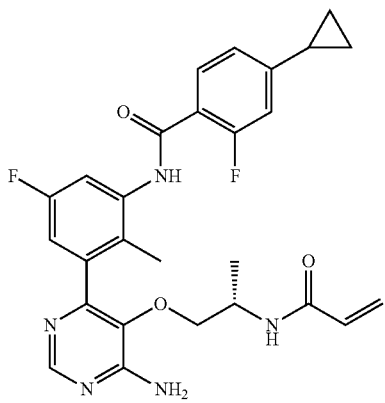 [SMILES: C=CC(=O)N[C@@H](C)COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with (S)-2-(Boc-amino)-1-propanol in step 1.

UPLC-MS: MS (ESI): [M+H]$^+$ 508.2, rt=0.95 min.

Example 18

(S)—N-(3-(6-Amino-5-(2-(but-2-ynamido)propoxy)pyrimidin-4-yl)-5-fluoro-2-methylphenyl)-4-cyclopropyl-2-fluorobenzamide

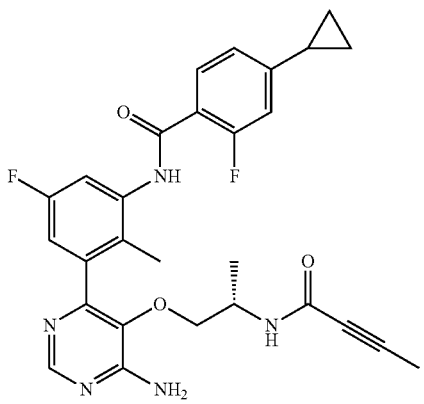 [SMILES: CC#CC(=O)N[C@@H](C)COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with (S)-2-(Boc-amino)-1-propanol in step 1, and replacing acrylic acid with 2-butynoic acid in step 4.

UPLC-MS: MS (ESI): [M+H]$^+$ 520.2, rt=0.97 min.

Example 19

(S)—N-(3-(6-Amino-5-(2-(N-methylacrylamido)propoxy)pyrimidin-4-yl)-5-fluoro-2-methylphenyl)-4-cyclopropyl-2-fluorobenzamide

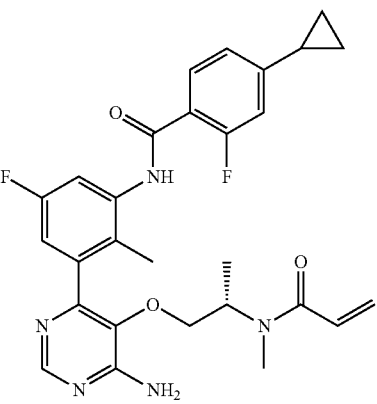 [SMILES: C=CC(=O)N(C)[C@@H](C)COc1c(N)ncnc1-c1cc(F)cc(NC(=O)c2ccc(C3CC3)cc2F)c1C]

(1) (S)—N-(3-(6-Amino-5-(2-aminopropoxy)pyrimidin-4-yl)-5-fluoro-2-methylphenyl)-4-cyclopropyl-2-fluorobenzamide, INT 18

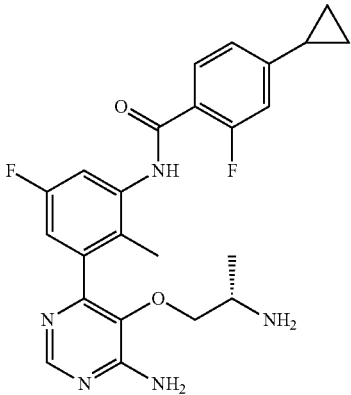 [SMILES: Cc1c(NC(=O)c2ccc(C3CC3)cc2F)cc(F)cc1-c1ncnc(N)c1OC[C@H](C)N]

INT 18 was prepared according to Scheme 2 following a procedure analogous to INT 10 replacing. N-Boc-N-methyl-2-hydroxyethylamine with (S)-2-(Boc-amino)-1-propanol in step 1, and replacing TFA with HCl in step 3 to afford INT 18 as the hydrochloride salt.

UPLC-MS: MS (ESI): [M+H]$^+$ 454.3, rt=0.73 min.

(2) (S)—N-(3-(6-Amino-5-(2-(benzyl(methyl)amino)propoxy)pyrimidin-4-yl)-5-fluoro-2-methylphenyl)-4-cyclopropyl-2-fluorobenzamide, INT 19

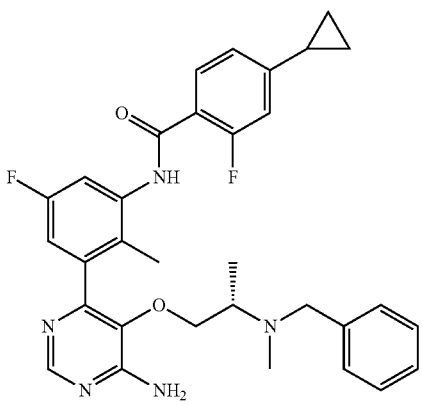 [SMILES: Cc1c(NC(=O)c2ccc(C3CC3)cc2F)cc(F)cc1-c1ncnc(N)c1OC[C@H](C)N(C)Cc1ccccc1]

To a solution of INT 18 (containing 2 eq of HCl, 590 mg, 1.12 mmol) in MeOH (30 mL) was added DIPEA (0.489 mL, 2.80 mmol), followed by acetic acid (0.321 mL, 5.60 mmol). Then a solution of benzaldehyde (131 mg, 1.23 mmol) in MeOH (3 mL) was added. The mixture was stirred at RT for 1 h, then sodium cyanoborohydride (77 mg, 1.23 mmol) was added. The reaction mixture was stirred at RT for 1 h. More sodium cyanoborohydride (35 mg, 0.561 mmol) was added and the mixture was stirred for an additional hour. Formaldehyde (37% in water, 1.00 mL, 13.45 mmol) was added, and stirring was continued for another hour. The mixture was diluted with DCM and washed with saturated aqueous sodium hydrogen carbonate solution. The organic layer was washed with brine, dried over magnesium sulfate, filtered and concentrated. The residue was purified by flash chromatography (silica; DCM/EtOAc gradient, 0-100%) to afford INT 19 as a white solid.

UPLC-MS: MS (ESI): [M+H]$^+$ 558.4, rt=0.90 min. $^1$H NMR (DMSO-d$_6$): δ (ppm) 9.79 (s, 1H), 8.20 (s, 1H), 7.63 (t, 1H), 7.55 (d, 1H), 7.34-7.14 (m, 7H), 7.12-6.95 (m, 3H), 3.65-3.56 (m, 1H), 3.48 (d, 1H), 3.39 (d, 1H), 3.34-3.27 (m, 2H), 2.99-2.86 (m, 1H), 2.03-1.99 (m, 4H), 1.94 (s, 3H), 1.11-0.99 (m, 2H), 0.83-0.70 (m, 2H).

(3) (S)—N-(3-(6-Amino-5-(2-(methylamino)propoxy)pyrimidin-4-yl)-5-fluoro-2-methylphenyl)-4-cyclopropyl-2-fluorobenzamide, INT 20

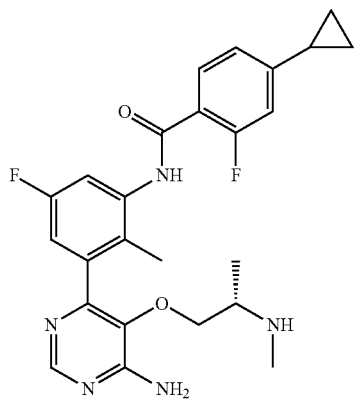

To a solution of INT 19 (470 mg, 0.843 mmol) in MeOH (9 mL) was added Pd—C 10% (47 mg). The reaction mixture was hydrogenated at RT and normal pressure for 18 hr. More Pd—C 10% (47 mg) was added and the reaction was hydrogenated at RT and normal pressure overnight. The mixture was diluted with DCM and filtered over a pad of Celite. The filtrate was concentrated and the residue was dried in vacuum to afford crude INT 20 as brown-gray solid.

UPLC-MS: MS (ESI): [M+H]$^+$ 468.4, rt=0.76 min. $^1$H NMR (DMSO-d$_6$): δ (ppm) 9.84 (s, 1H), 8.18 (s, 1H), 7.65 (t, 1H), 7.58-7.49 (m, 1H), 7.28 (s, br, 1H), 7.09-7.00 (m, 3H), 3.34-3.25 (m, 3H), 3.17 (s, br, 1H), 2.17-1.98 (m, 7H), 1.67 (s, br, 1H), 1.08-1.01 (m, 2H), 0.81-0.77 (m, 2H).

(4) (S)—N-(3-(6-Amino-5-(2-(N-methylacrylamido)propoxy)pyrimidin-4-yl)-5-fluoro-2-methylphenyl)-4-cyclopropyl-2-fluorobenzamide The title compound was prepared according to Scheme 2 following a procedure analogous to step 4 of Example 6 replacing INT 10 with INT 20.

UPLC-MS: MS (ESI): [M+H]$^+$ 522.3, rt=0.99 min.

Example 20

(S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide

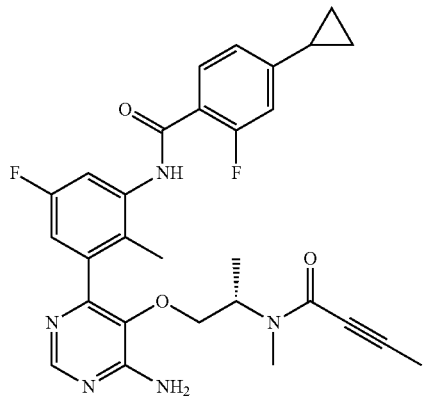

(1) (S)-tert-Butyl (5-(2-(but-2-ynamido)propoxy)-6-(3-(N-(tert-butoxycarbonyl)-4-cyclopropylbenzamido)-5-fluoro-2-methylphenyl)pyrimidin-4-yl)(tert-butoxycarbonyl)carbamate, INT 21

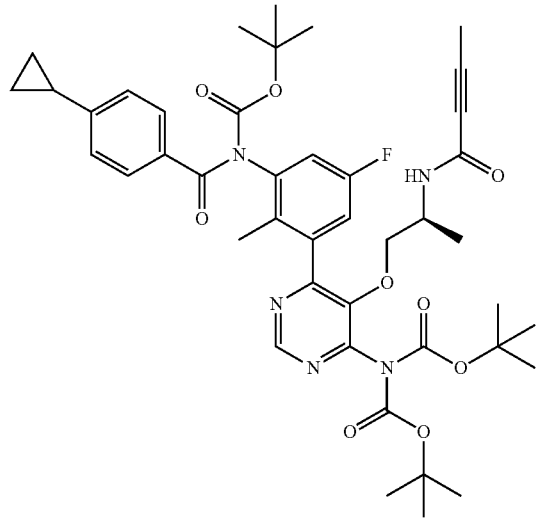 [SMILES: CC#CC(=O)N[C@@H](C)COc1c(-c2cc(F)cc(N(C(=O)OC(C)(C)C)C(=O)c3ccc(C4CC4)cc3)c2C)ncnc1N(C(=O)OC(C)(C)C)C(=O)OC(C)(C)C]

To a solution of Example 18 (152 mg, 0.29 mmol) in THF (10 mL) was added DIPEA (0.200 mL, 115 mmol) followed by di-tert-butyl dicarbonate (233 mg, 1.07 mmol) and 4-(dimethylamino)pyridine (4 mg, 0.033 mmol). The reaction mixture was stirred at RT overnight. More di-tert-butyl dicarbonate (100 mg, 0.46 mmol) was added and the reaction mixture was stirred at RT for 1.5 hr. The mixture was concentrated under reduced pressure. The residue was purified by flash chromatography (silica; cyclohexane/EtOAc gradient, 0-100%) to afford INT 21 as a yellow residue.

UPLC-MS: MS (ESI): [M+H]+ 820.4, rt=1.48 min.

(2) (S)-tert-butyl tert-butoxycarbonyl(6-(3-(N-(tert-butoxycarbonyl)-4-cyclopropyl-benzamido)-5-fluoro-2-methylphenyl)-5-(2-(N-methylbut-2-ynamido)propoxy)pyrimidin-4-yl)carbamate, INT 22

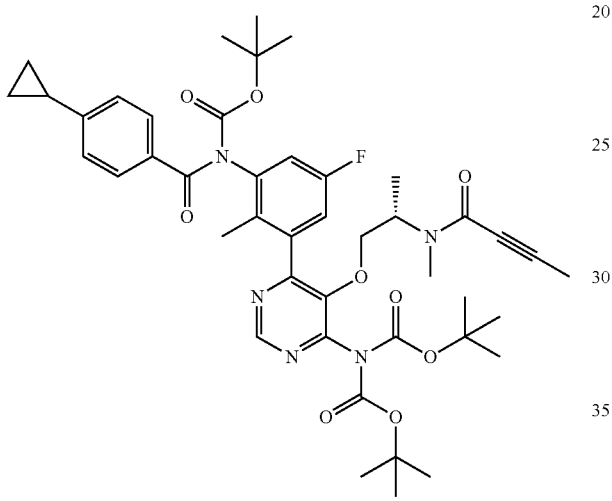

To a solution of INT 21 (257 mg, 0.31 mmol) and iodomethane (0.040 mL, 0.64 mmol) in DMF (5.0 mL) at 0° C. was added NaH (60% in mineral oil, 26 mg, 0.65 mmol). The reaction mixture was stirred for 1.5 hr while allowing to warm to RT. The mixture was poured into aqueous HCl (0.5 M) and extracted with EtOAc (2×). The combined organic layers were washed with brine, dried over sodium sulfate, filtered and concentrated. The residue was purified by flash chromatography (silica; cyclohexane/EtOAc gradient, 0-100%) to afford INT 22.

UPLC-MS: MS (ESI): [M+H]+ 834.5, rt=1.49 min.

(3) (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide To a solution of INT 22 (117 mg, 0.14 mmol) in DCM (5.0 mL) was added TFA (0.200 mL, 2.60 mmol) followed by one drop of water. The reaction mixture was stirred at RT overnight. The mixture was concentrated. The residue was taken up in EtOAc and washed with saturated aqueous sodium hydrogen carbonate solution. The aqueous layer was back-extracted with EtOAc. The combined organic layers were washed with brine, dried over magnesium sulfate, filtered and concentrated. The residue was purified by flash chromatography (silica; EtOAc/MeOH gradient, 0-15%) followed by purification by SFC to afford Example 20.

UPLC-MS: MS (ESI): [M+H]+ 534.3, rt=1.02 min. 1H NMR (CDCl3): δ (ppm) rotamers 8.65-8.54 (m, 1H), 8.38 and 8.33 (s, total 1H), 8.19-8.05 (m, 2H), 7.07-6.95 (m, 2H), 6.90-6.82 (m, 1H), 5.76 and 5.23 (s, total 2H), 4.99-4.92 and 4.76-4.68 (m, total 1H), 3.54-3.45 (m, 1H), 3.43-3.37 and 3.28-3.21 (m, total 1H), 2.91 and 2.65 (s, total 3H), 2.16 (s, 3H), 2.03-1.92 (overlapping s and m, total 4H), 1.15-1.08 (m, 2H), 1.01 and 0.95 (d, total 3H), 0.83-0.77 (m, 2H).

Example 21

N-(3-(6-Amino-5-(3-(N-methylacrylamido)propoxy)pyrimidin-4-yl)-5-fluoro-2-methylphenyl)-4-cyclopropyl-2-fluorobenzamide

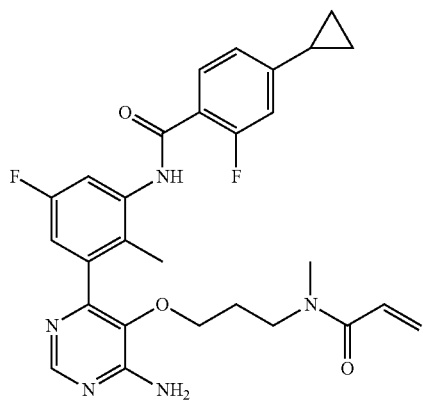 [SMILES: C=CC(=O)N(C)CCCOc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with N-Boc-N-methyl-3-hydroxypropylamine in step 1.

UPLC-MS: MS (ESI): [M+H]+ 522.4, rt=0.95 min.

Example 22

(S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide

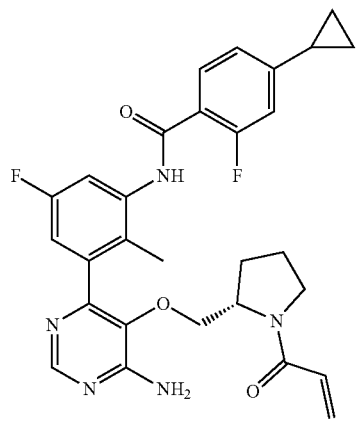

The title compound was prepared according to Scheme 2 following a procedure analogous to Example 6 replacing N-Boc-N-methyl-2-hydroxyethylamine with (S)—N-Boc-2-(hydroxymethyl)pyrrolidine in step 1.

UPLC-MS: MS (ESI): [M+H]+ 534.3, rt=1.00 min

Example 23

(S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide

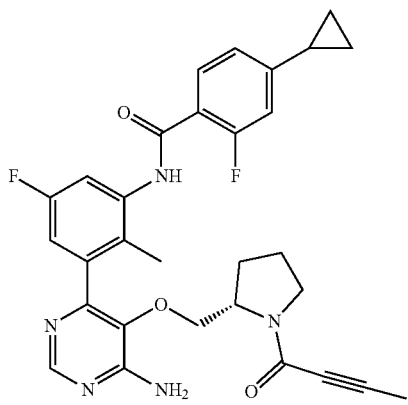 [SMILES: CC#CC(=O)N1CCC[C@H]1COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with (S)—N-Boc-2-(hydroxymethyl)pyrrolidine in step 1, and replacing acrylic acid with 2-butynoic acid in step 4.

UPLC-MS: MS (ESI): [M+H]+ 546.3, rt=1.02 min.

Example 24

(S)-2-(3-(5-(((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one

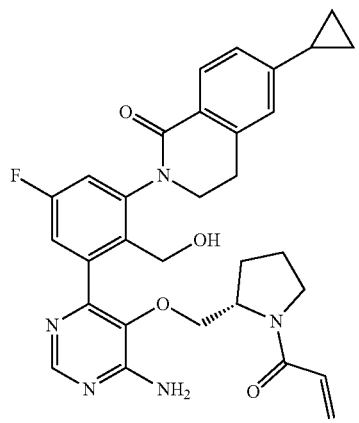 [SMILES: C=CC(=O)N1CCC[C@H]1COc1c(N)ncnc1-c1cc(F)cc(N2CCc3cc(C4CC4)ccc3C2=O)c1CO]

(1) 2-(6-Cyclopropyl-1-oxo-3,4-dihydroisoquinolin-2(1H)-yl)-4-fluoro-6-(4,4,5,5-tetramethyl-1,3,2-dioxaborolan-2-yl)benzyl acetate, INT 23

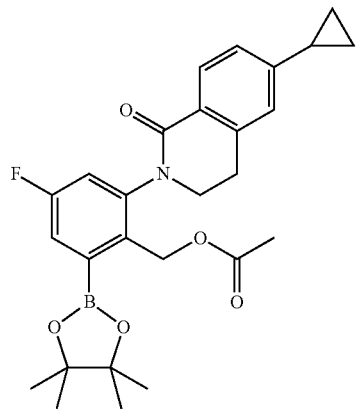 [SMILES: CC(=O)OCc1c(B2OC(C)(C)C(C)(C)O2)cc(F)cc1N1CCc2cc(C3CC3)ccc2C1=O]

INT 23 was prepared following a procedure analogous to INT 2 replacing 1-bromo-5-fluoro-2-methyl-3-nitro-benzene with acetic acid 2-bromo-6-(6-cyclopropyl-1-oxo-3,4-dihydro-1H-isoquinolin-2-yl)-benzyl ester (WO2010/000633).

UPLC-MS: MS (ESI): [M+H]+ 480.4, rt=1.36 min. 1H NMR (DMSO-d6): δ (ppm) 7.76 (s, 1H), 7.49-7.46 (m, 1H), 7.38-7.35 (m, 1H), 7.10 (d, 1H), 7.06 (s, 1H), 5.24 (d, 1H), 4.93 (d, 1H), 4.07-3.98 (m, 1H), 3.65-3.58 (m, 1H), 3.15-2.99 (m, 2H), 2.04-1.96 (m, 1H), 1.91 (s, 3H), 1.31 (s, 12H), 1.05-1.00 (m, 2H), 0.80-0.75 (m, 2H).

(2) (S)-tert-Butyl 2-(((4-amino-6-chloropyrimidin-5-yl)oxy)methyl)pyrrolidine-1-carboxylate, INT 24

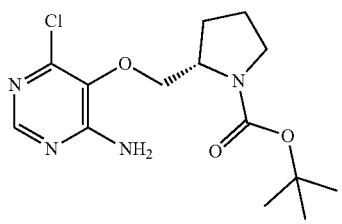 [SMILES: CC(C)(C)OC(=O)N1CCC[C@H]1COc1c(N)ncnc1Cl]

INT 24 was prepared according to Scheme 2 following a procedure analogous to step 1 of Example 6 replacing N-Boc-N-methyl-2-hydroxyethylamine with (S)—N-Boc-2-(hydroxymethyl)pyrrolidine.

UPLC-MS: MS (ESI): [M+H]+ 329.2, rt=0.97 min.

(3) (S)-tert-Butyl 2-(((4-amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)methyl)pyrrolidine-1-carboxylate, INT 25

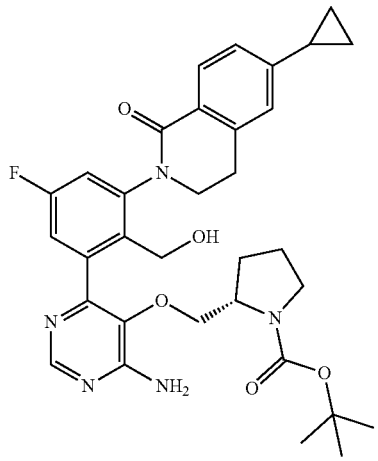 [SMILES: CC(C)(C)OC(=O)N1CCC[C@H]1COc1c(N)ncnc1-c1cc(F)cc(N2CCc3cc(C4CC4)ccc3C2=O)c1CO]

To a solution of INT 24 (content 66%, 200 mg, 0.40 mmol) in DME (3.0 mL) and water (0.43 mL) was added INT 23 (212 mg, 0.44 mmol) followed by aqueous sodium carbonate solution (1 M, 1.20 mL, 1.20 mmol). The mixture was degassed with argon for 10 min, then bis(triphenylphosphine)-palladium(II) dichloride (14 mg, 0.020 mmol) was added. The reaction mixture was stirred at 90° C. for 6 hr. After cooling to RT, aqueous NaOH solution (2 M, 2.0 mL, 4.00 mmol) was added and the mixture was stirred at RT for 20 min. The mixture was diluted with saturated aqueous sodium hydrogen carbonate solution and extracted with EtOAc. The organic layer was washed with water and brine, dried over magnesium sulfate, filtered and concentrated. The residue was purified by flash chromatography (silica; DCM/EtOAc gradient, 0-100%) to afford INT 25 as a beige solid.

UPLC-MS: MS (ESI): [M+H]$^+$ 604.5, rt=1.20 min. $^1$H NMR (DMSO-d$_6$): δ (ppm) 8.21 (s, 1H), 7.79 (d, 1H), 7.40 (d, 1H), 7.21 (d, 1H), 7.11 (d, 1H), 7.07 (s, 1H), 7.04-6.87 (s, br, 2H), 4.86-4.66 (m, 1H), 4.31 (m, 2H), 4.03-3.93 (m, 1H), 3.81-3.70 (m, 2H), 3.64-3.53 (m, 2H), 3.35-3.00 (m, 4H), 2.03-1.97 (m, 1H), 1.64-1.44 (m, 4H), 1.40-1.24 (m, 9H), 1.06-1.01 (m, 2H), 0.79-0.76 (m, 2H).

(4) (S)-2-(3-(6-Amino-5-(pyrrolidin-2-ylmethoxy)pyrimidin-4-yl)-5-fluoro-2-(hydroxymethyl)phenyl)-6-cyclopropyl-3,4-dihydroisoquinolin-1(2H)-one, INT 26

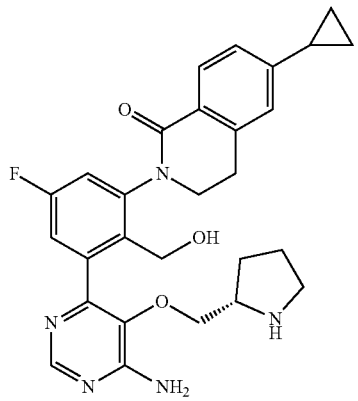 [SMILES: Nc1ncnc(-c2cc(F)cc(N3CCc4cc(C5CC5)ccc4C3=O)c2CO)c1OC[C@@H]1CCCN1]

INT 26 was prepared according to Scheme 2 following a procedure analogous to step 3 of Example 6 replacing INT 9 with INT 25.

UPLC-MS: MS (ESI): [M+H]$^+$ 504.4, rt=0.75 min.

(5) (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one The title compound was prepared according to Scheme 2 following a procedure analogous to step 4 of Example 6 replacing INT 10 with INT 26.

UPLC-MS: MS (ESI): [M+H]$^+$ 558.4, rt=0.98 min.

Example 25

N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide

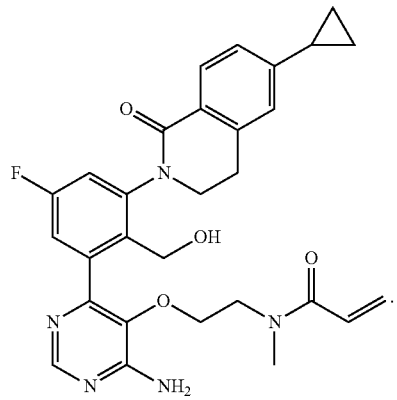 [SMILES: C=CC(=O)N(C)CCOc1c(N)ncnc1-c1cc(F)cc(N2CCc3cc(C4CC4)ccc3C2=O)c1CO]

(1) 2-(3-(6-Amino-5-(2-(methylamino)ethoxy)pyrimidin-4-yl)-5-fluoro-2-(hydroxymethyl)-phenyl)-6-cyclopropyl-3,4-dihydroisoquinolin-1(2H)-one, INT 27

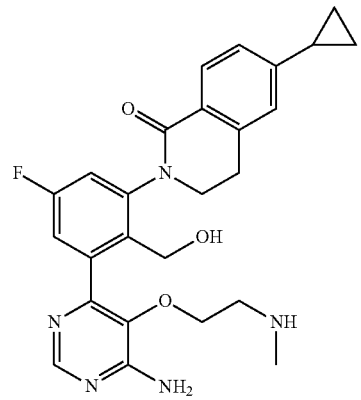 [SMILES: CNCCOc1c(N)ncnc1-c1cc(F)cc(N2CCc3cc(C4CC4)ccc3C2=O)c1CO]

INT 27 was prepared according to Scheme 2 following a procedure analogous to INT 26 replacing INT 24 with INT 8 in step 3, and purifying the TFA salt over a SPE cartridge (PL-HCO3 MP resin) to afford INT 27 as the free amine in step 4.

UPLC-MS: MS (ESI): [M+H]⁺ 478.3, rt=0.62 min.

(2) N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide To a solution of INT 27 (free amine, 130 mg, 0.272 mmol) and DIPEA (0.238 ml, 1.361 mmol) in DCM (9.0 mL) at −20° C. was added a solution of acryloyl chloride (24.64 mg, 0.272 mmol) in DCM (0.6 mL). The reaction mixture was stirred at −20° C. for 10 min. The mixture was diluted with DCM and poured into brine. The aqueous layer was back-extracted with DCM. The combined organic layers were dried over sodium sulfate and filtered. The filtrate was directly loaded onto a silica cartridge and purified by flash chromatography (silica; heptane/acetone gradient, 0-80%) to afford a white solid. The residue was triturated in acetonitrile, filtered off, and rinsed with acetonitrile. The solid was dried in vacuum to afford Example 25 as a white solid.

UPLC-MS: MS (ESI): [M+H]+ 530.5, rt=0.89 min. 1H NMR (DMSO-d6): δ (ppm) rotamers 8.23-8.16 (m, 1H), 7.83-7.77 (m, 1H), 7.43-7.32 (m, 1H), 7.20-7.04 (m, 5H), 6.70-6.60 (m, 1H), 6.11-6.00 (m, 1H), 5.69-5.53 (m, 1H), 4.77-4.61 (m, 1H), 4.37-4.24 (m, 2H), 4.05-3.93 (m, 1H), 3.83-3.73 (m, 1H), 3.68-3.55 (m, 2H), 3.54-3.44 (m, 1H), 3.27-3.15 (m, 2H), 3.09-2.99 (m, 1H), 2.89-2.55 (m, 3H), 2.05-1.95 (m, 1H), 1.08-0.99 (m, 2H), 0.81-0.74 (m, 2H).

Example 26

N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide

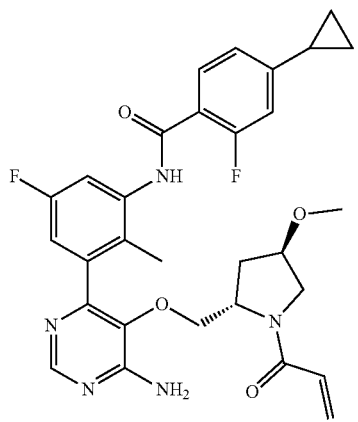 [SMILES: C=CC(=O)N1C[C@H](OC)C[C@H]1COc1c(N)ncnc1-c1cc(F)cc(NC(=O)c2ccc(C3CC3)cc2F)c1C]

(1) (2S,4R)—N-Boc-4-methoxypyrrolidine-2-carboxylic acid, INT 28

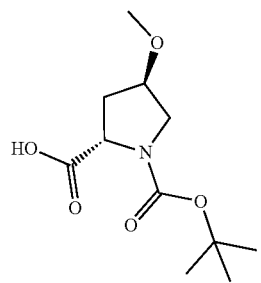 [SMILES: CO[C@@H]1C[C@@H](C(=O)O)N(C(=O)OC(C)(C)C)C1]

INT 28 was prepared following a procedure analogous to WO2002/102790.

MS (ESI): [M−H]⁺ 244.2. ¹H NMR (DMSO-d₆): δ (ppm) rotamers 4.05-3.97 (m, 1H), 3.95-3.87 (m, 1H), 3.45-3.30 (m, 2H), 3.20 (s, 3H), 2.25-2.11 (m, 1H), 1.99-1.91 (m, 1H), 1.39 and 1.33 (s, total 9H).

(2) (2S,4R)—N-Boc-2-(hydroxymethyl)-4-methoxypyrrolidine, INT 29

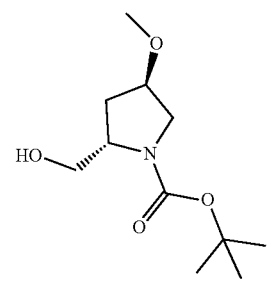 [SMILES: CO[C@@H]1C[C@@H](CO)N(C(=O)OC(C)(C)C)C1]

To solution of INT 28 (5.00 g, 20.39 mmol) in THF (100 mL) at 0° C. was added borane tetrahydrofuran complex solution (1 M in THF, 30.6 mL, 30.6 mmol) dropwise. The reaction mixture was stirred at RT for 6 hr. The mixture was cooled to 0° C. and water (80 mL) was added dropwise. The resulting mixture was stirred at 0° C. for 1 hr, then diluted with EtOAc. The organic layer was washed with aqueous 10% citric acid solution, saturated aqueous sodium hydrogen carbonate solution and brine, dried over magnesium sulfate, filtered and concentrated. The residue was dried in vacuum to afford crude INT 29 as a colorless liquid.

MS (ESI): [M+H−tBu]⁺ 176.1. ¹H NMR (DMSO-d₆): δ (ppm) 4.69 (t, 1H), 3.94-3.88 (m, 1H), 3.73 (s, v br, 1H), 3.48-3.36 (m, 3H), 3.31-3.22 (m, 1H), 3.20 (s, 3H), 2.08-1.87 (m, 2H), 1.40 (s, 9H).

(3) (2S,4R)-tert-Butyl 2-(((4-amino-6-chloropyrimidin-5-yl)oxy)methyl)-4-methoxypyrrolidine-1-carboxylate, INT 30

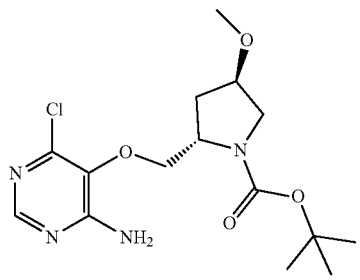 [SMILES: CO[C@@H]1C[C@@H](COc2c(N)ncnc2Cl)N(C(=O)OC(C)(C)C)C1]

INT 30 was prepared according to Scheme 2 following a procedure analogous to step 1 of Example 6 replacing N-Boc-N-methyl-2-hydroxyethylamine with INT 29.

UPLC-MS: MS (ESI): [M+H]⁺ 359.3, rt=0.91 min.

(4) N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide The title compound was prepared according to Scheme 2 following a procedure analogous to Example 6 replacing INT 8 with INT 30 in step 2.

UPLC-MS: MS (ESI); [M+H]⁺ 564.4, rt=0.98 min.

Example 27

N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide

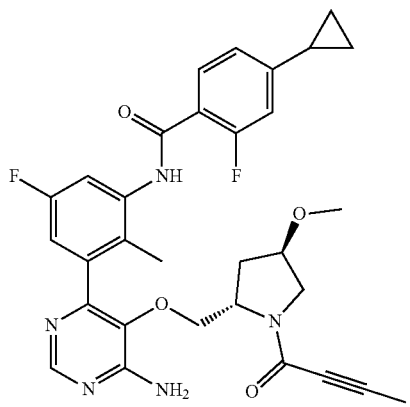 [SMILES: CC#CC(=O)N1C[C@H](OC)C[C@H]1COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with INT 29 in step 1, and replacing acrylic acid with 2-butynoic acid in step 4.

UPLC-MS: MS (ESI): [M+H]⁺ 576.4, rt=1.01 min.

Example 28

2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one

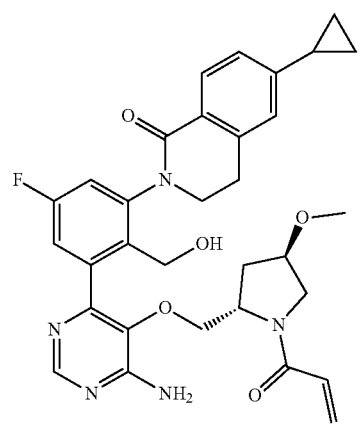 [SMILES: C=CC(=O)N1C[C@H](OC)C[C@H]1COc1c(N)ncnc1-c1cc(F)cc(N2CCc3cc(C4CC4)ccc3C2=O)c1CO]

The title compound was prepared according to Scheme 2 following a procedure analogous to Example 24 replacing INT 24 with INT 30 in step 3.

UPLC-MS: MS (ESI): [M+H]⁺ 588.5, rt=0.95 min.

Example 29

N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide

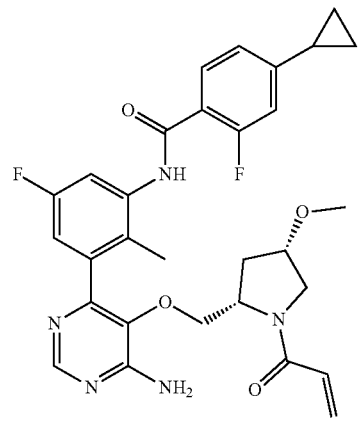 [SMILES: C=CC(=O)N1C[C@@H](OC)C[C@H]1COc1c(N)ncnc1-c1cc(F)cc(NC(=O)c2ccc(C3CC3)cc2F)c1C]

(1) (2S,4S)-Methyl N-Boc-4-methoxypyrrolidine-2-carboxylate, INT 31

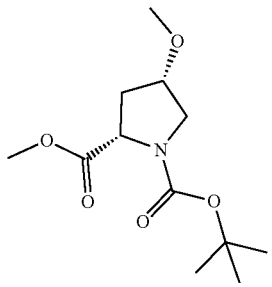 [SMILES: COC(=O)[C@@H]1C[C@H](OC)CN1C(=O)OC(C)(C)C]

To a solution of (2S,4S)-methyl N-Boc-4-hydroxypyrrolidine-2-carboxylate (3.00 g, 12.23 mmol) in acetonitrile (60 mL) was added silver oxide (2.83 g, 12.23 mmol) followed by iodomethane (15.0 mL, 240.95 mmol). The reaction mixture was stirred at 85° C. for 4 hr. More iodomethane (5.0 mL, 80.32 mmol) was added and the mixture was stirred at 85° C. for an additional 5 hr. The mixture was filtered over a pad of Celite. The filtrated was diluted with diethyl ether and washed with saturated aqueous sodium hydrogen carbonate solution. The aqueous layer was back-extracted with diethyl ether. The combined organic layers were washed with brine, dried over magnesium sulfate, filtered and concentrated to afford crude INT 31 as a pale yellow oil.

MS (ESI): [M+H]$^+$ 260.3. $^1$H NMR (DMSO-d$_6$): δ (ppm) rotamers 4.30-4.23 (m, 1H), 3.95-3.91 (m, 1H), 3.64 and 3.61 (s, total 3H), 3.55-3.50 (m, 1H), 3.27-3.21 (m, 1H), 3.17 and 3.16 (s, total 3H), 2.42-2.28 (m, 1H), 2.06-1.97 (m, 1H), 1.41 and 1.34 (s, total 9H).

(2) (2S,4S)—N-Boc-2-(hydroxymethyl)-4-methoxypyrrolidine, INT 32

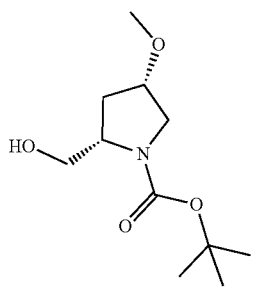 [SMILES: CO[C@H]1C[C@@H](CO)N(C(=O)OC(C)(C)C)C1]

To a solution of INT 31 (3.10 g, 11.96 mmol) in THF (120 mL) at 0° C. was added lithium borohydride solution (2 M in THF, 11.96 mL, 23.91 mmol). The reaction mixture was stirred at RT overnight. The mixture was cooled to 0° C. and poured onto ice water. The mixture was stirred for 15 min at RT, then extracted with diethyl ether. The aqueous layer was back-extracted with diethyl ether. The combined organic layers were washed with brine, dried over magnesium sulfate, filtered and concentrated to afford crude INT 32 as a colorless oil.

MS (ESI): [M+H]$^+$ 232.3. $^1$H NMR (DMSO-d$_6$): δ (ppm) 4.64 (t, 1H), 3.87 (s, 1H), 3.68-3.44 (m, 3H), 3.32-3.26 (m, 1H), 3.21 (s, 3H), 3.18-3.15 (m, 1H), 2.04-1.97 (m, 1H), 1.42-1.34 (m, 1H), 1.40 (s, 9H).

(3) N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide The title compound was prepared according to Scheme 2 following a procedure analogous to Example 6 replacing N-Boc-N-methyl-2-hydroxyethylamine with INT 32 in step 1.

UPLC-MS: MS (ESI): [M+H]$^+$ 564.4, rt=0.99 min.

Example 30

N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide

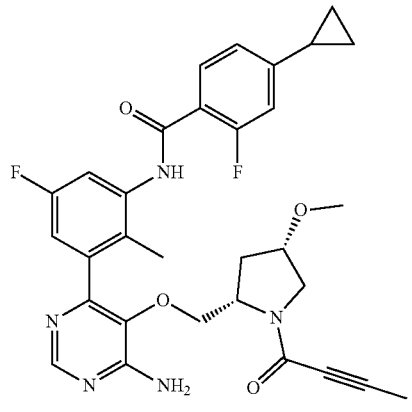 [SMILES: CC#CC(=O)N1C[C@@H](OC)C[C@H]1COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with INT 32 in step 1, and replacing acrylic acid with 2-butynoic acid in step 4.

UPLC-MS: MS (ESI): [M+H]$^+$ 576.4, rt=1.02 min.

Example 31

N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide

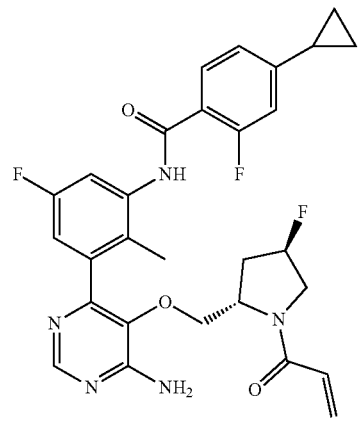 [SMILES: C=CC(=O)N1C[C@H](F)C[C@H]1COc1c(N)ncnc1-c1cc(F)cc(NC(=O)c2ccc(C3CC3)cc2F)c1C]

(1) (2S,4R)—N-Boc-4-fluoropyrrolidin-2-carboxylic acid, INT 33

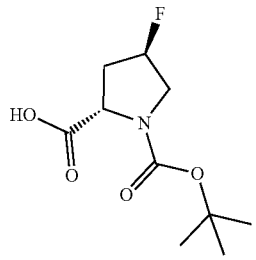 [SMILES: CC(C)(C)OC(=O)N1C[C@H](F)C[C@H]1C(=O)O]

A solution of (2S,4R) methyl N-Boc-4-hydroxypyrrolidine-2-carboxylate (250 g, 1.02 mol), triphenylphosphine (401 g, 1.53 mmol) and benzoic acid (187 g, 1.53 mol) in THF (3.50 L) was cooled to reach an internal temperature of −4° C., then a diethyl azodicarboxylate solution (40% in toluene, 625 mL, 1.43 mmol) in THF (1.50 L) was added within 1 hr. The reaction mixture was warmed to RT and stirred at RT overnight. The mixture was concentrated. The residue was taken up in diethyl ether (2.5 L) and the mixture was refluxed for 1 hr. The suspension was cooled to 0° C., the white solid was filtered off, and washed with cold ethanol. The filtrate was concentrated. The residue was dissolved in a 4:1 mixture of warm hexane/EtOAc (1.5 L) and stirred at RT for 1 hr. The mixture was cooled to 10° C. and treated with hexane (250 mL). The mixture was stirred at RT for 30 min and a precipitate was formed. The solid was filtered off and washed with cold hexane (150 mL). The filtrate was concentrated. The residue was purified by flash chromatography (silica; hexane/EtOAc 4:1) to afford (2S,4S)-2-methyl N-Boc-4-(benzoyloxy)pyrrolidine-2-carboxylate as a white solid.

To a solution of (2S,4S)-2-methyl N-Boc-4-(benzoyloxy)pyrrolidine-2-carboxylate (248 g, 0.71 mol) in MeOH (4.5 L) was added sodium carbonate (98 g, 0.92 mol) followed by more MeOH (0.5 L). The reaction mixture was stirred at RT for 4 hr. The mixture was filtered, and the filtrated was concentrated to a volume of approximately 1 L. The solution was diluted with EtOAc (5.0 L), cooled to 5° C. and washed with water. The aqueous layer was back-extracted with EtOAc (2×). The combined organic layers were washed with brine and a 1:1 mixture of brine and water, dried over sodium sulfate, filtered and concentrated. The residue was crystallized from DCM/hexane to afford (2S,4S)-2-methyl N-Boc-4-hydroxy-pyrrolidine-2-carboxylate as a white solid. To a solution of (2S,4S)-2-methyl N-Boc-4-hydroxypyrrolidine-2-carboxylate (270 g, 1.10 mol) in DCM (2.6 L) at −80° C. was added (diethylamino)sulfur trifluoride (567 mL, 4.29 mol) dropwise. The reaction mixture was stirred at RT overnight. The mixture was cooled to −78° C. and then added to a saturated aqueous sodium hydrogen carbonate solution cooled to −10° C. During the addition the inner temperature was kept below 5° C. The mixture was then stirred at 0° C. for 30 min. The layers were separated, the aqueous layer was back-extracted with DCM. The combined organic layers were washed with saturated aqueous sodium hydrogen carbonate solution, dried over sodium sulfate, filtered and concentrated. The residue was purified by flash chromatography (silica; hexane/EtOAc gradient, 10-40%) to afford (2S,4R)-2-methyl N-Boc-4-fluoro-pyrrolidine-2-carboxylate as a yellow oil.

To a solution of (2S,4R)-2-methyl N-Boc-4-fluoro-pyrrolidine-2-carboxylate (13.0 g, 52.58 mmol) in dioxane (270 mL) at 15° C. was added a solution of sodium hydroxide (4.2 g, 105.00 mmol) in water (30 mL) dropwise. The mixture was cooled to 7° C. and the slurry was stirred at 7° C. overnight. Acetic acid (80 mL) was added and the mixture was diluted with DCM. The layers were separated, the aqueous layer was back-extracted with DCM. The combined organic layers were washed with brine, dried over sodium sulfate, filtered and concentrated. The residue was crystallized from diethyl ether/hexane to afford INT 33 as a white solid.

MS (ESI): [M−H]⁻ 232.2. $^1$H NMR (DMSO-$d_6$): δ (ppm) rotamers 12.72 (s, br, 1H), 5.40-5.21 (m, 1H), 4.22-4.13 (m, 1H), 3.72-3.58 (m, 1H), 3.58-3.36 (m, 1H), 2.60-2.44 (m, 1H, overlapping with solvent peak), 2.19-1.97 (m, 1H), 1.41 and 1.36 (s, total 9H).

(2) (2S,4R)—N-Boc-2-(hydroxymethyl)-4-fluoropyrrolidine, INT 34

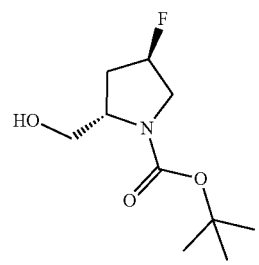

To a solution of INT 33 (5.00 g, 21.44 mmol) in THF (105 mL) at 0° C. was added borane tetrahydrofuran complex solution (1 M in THF, 32.2 mL, 32.20 mmol). The reaction mixture was stirred at RT for 3 hr. The mixture was cooled to 0° C. and water (100 mL) was added dropwise. The resulting mixture was stirred at 0° C. for 1 hr, then extracted with EtOAc. The organic layer was washed with aqueous 10% citric acid solution, saturated aqueous sodium hydrogen carbonate solution and brine, dried over magnesium sulfate, filtered and concentrated to afford crude INT 34 as a yellow oil.

MS (ESI): [M+H−tBu]⁺ 164.2. $^1$H NMR (DMSO-$d_6$): δ (ppm) 5.23 (d, 1H), 4.74 (t, 1H), 3.84 (m, 1H), 3.74-3.62 (m, 1H), 3.57-3.44 (m, 2H), 3.41-3.23 (m, 1H), 2.22-2.05 (m, 2H), 1.41 (s, 9H).

(3) N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide The title compound was prepared according to Scheme 2 following a procedure analogous to Example 6 replacing N-Boc-N-methyl-2-hydroxyethylamine with INT 34 in step 1.

UPLC-MS: MS (ESI): [M+H]⁺ 552.5, rt=1.00 min.

Example 32

N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide

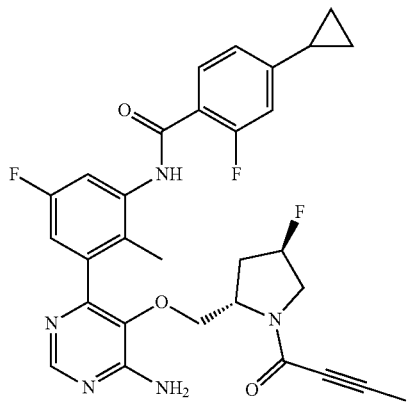 [SMILES: CC#CC(=O)N1C[C@H](F)C[C@H]1COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with INT 34 in step 1, and replacing acrylic acid with 2-butynoic acid in step 4.
UPLC-MS: MS (ESI): [M+H]⁺ 564.5, rt=1.03 min.

Example 33

(S)—N-(3-(5-((1-Acryloylazetidin-2-yl)methoxy)-6-aminopyrimidin-4-yl)-5-fluoro-2-methylphenyl)-4-cyclopropyl-2-fluorobenzamide

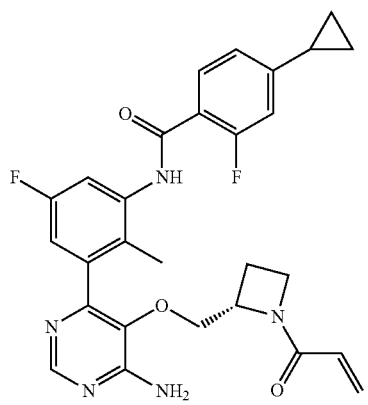 [SMILES: C=CC(=O)N1CC[C@H]1COc1c(N)ncnc1-c1cc(F)cc(NC(=O)c2ccc(C3CC3)cc2F)c1C]

(1) (S)—N-Boc-2-(hydroxymethyl)azetidine, INT 35

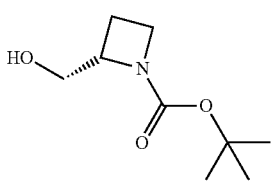

INT 35 was prepared according to Scheme 2 following a procedure analogous to step 2 of Example 26 replacing INT 28 with (S)—N-Boc-azetidine-2-carboxylic acid.
MS (ESI): [M+H]⁺ 188.1.

(2) (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide The title compound was prepared according to Scheme 2 following a procedure analogous to Example 6 replacing N-Boc-N-methyl-2-hydroxyethylamine with INT 35 in step 1.
UPLC-MS: MS (ESI): [M+H]⁺ 520.2, rt=0.96 min.

Example 34

(S)—N-(3-(6-Amino-5-((1-propioloylazetidin-2-yl)methoxy)pyrimidin-4-yl)-5-fluoro-2-methylphenyl)-4-cyclopropyl-2-fluorobenzamide

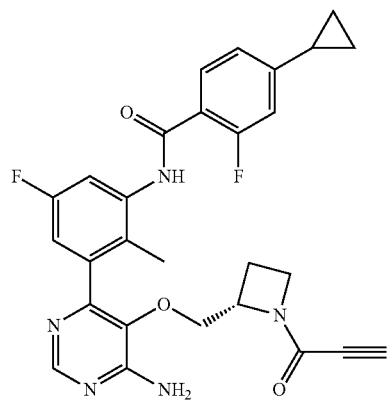 [SMILES: C#CC(=O)N1CC[C@H]1COc1c(N)ncnc1-c1cc(F)cc(NC(=O)c2ccc(C3CC3)cc2F)c1C]

The title compound was prepared according to Scheme 2 following a procedure analogous to Example 6 replacing N-Boc-N-methyl-2-hydroxyethylamine with INT 35 in step 1, and replacing acrylic acid with propiolic acid in step 4.
UPLC-MS (ESI): [M+H]⁺ 518.3, rt=0.96 min.

Example 35

(S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one

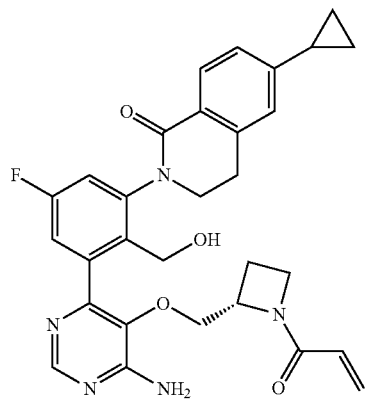 [SMILES: C=CC(=O)N1CC[C@H]1COc1c(N)ncnc1-c1cc(F)cc(N2CCc3cc(C4CC4)ccc3C2=O)c1CO]

63

(1) (S)-tert-Butyl 2-(((4-amino-6-chloropyrimidin-5-yl)oxy)methyl)azetidine-1-carboxylate, INT 36

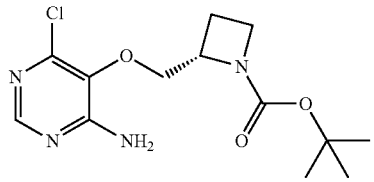 [SMILES: CC(C)(C)OC(=O)N1CC[C@H]1COc1c(N)ncnc1Cl]

INT 36 was prepared according to Scheme 2 following a procedure analogous to step 1 of Example 6 replacing N-Boc-N-methyl-hydroxyethylamine with INT 35.

UPLC-MS: MS (ESI): [M+H]$^+$ 315.1, rt=0.91 min.

(2) (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one The title compound was prepared according to Scheme 2 following a procedure analogous to Example 24 replacing INT 24 with INT 36 in step 3.

UPLC-MS: MS (ESI): [M+H]$^+$ 544.4, rt=0.94 min.

Example 36

(R)—N-(3-(5-((1-Acryloylazetidin-2-yl)methoxy)-6-aminopyrinnidin-4-yl)-5-fluoro-2-methylphenyl)-4-cyclopropyl-2-fluorobenzamide

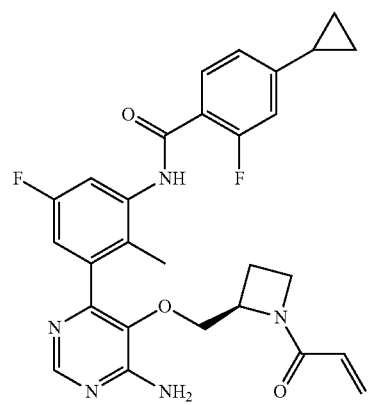 [SMILES: C=CC(=O)N1CC[C@@H]1COc1c(N)ncnc1-c1cc(F)cc(NC(=O)c2ccc(C3CC3)cc2F)c1C]

The title compound was prepared according to Scheme 2 following a procedure analogous to Example 33 replacing (S)—N-Boc-azetidine-2-carboxylic acid with (R)—N-Boc-azetidine-2-carboxylic acid in step 1.

UPLC-MS: MS (ESI): [M+H]$^+$ 520.3, rt=0.99 min.

Example 37

(R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide

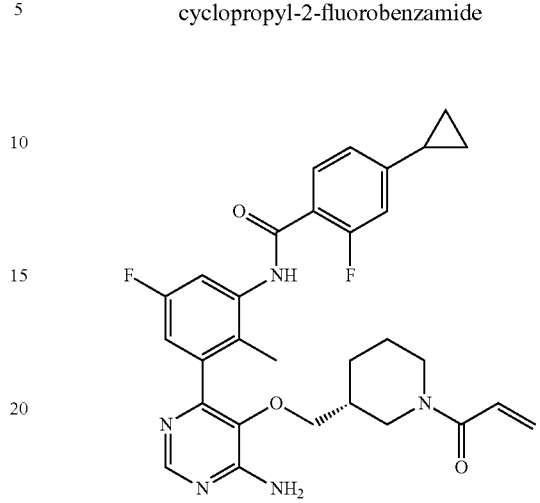

The title compound was prepared according to Scheme 2 following a procedure analogous to Example 6 replacing N-Boc-N-methyl-hydroxyethylamine with (R)—N-Boc-3-(hydroxylmethyl)piperidine in step 1.

UPLC-MS: MS (ESI): [M+H]$^+$ 548.5, rt=1.02 min.

Alternatively, agents of the invention may be prepared by a reaction sequence involving deprotection e.g. with a Lewis acid of 4,6-dichloro-5-methoxypyrimidine 8 to yield 4,6-dichloro-5-hydroxyoxy-pyrimidine 9, followed by a Mitsunobu reaction of the pyrimidinol with an alcohol compound 2' using an appropriate azodicarboxylate, such as DIAD, and Smopex-301 or triphenylphosphine to yield intermediate 10, followed by a nucleophilic aromatic substitution e.g. with ammonia in water to yield the aminopyrimidine intermediate 3. Thereupon intermediate 3 is converted into a final compound of the invention, i.e. a compound 7, by the earlier described reaction sequences of scheme 1 and/or scheme 2, i.e. a Suzuki coupling with a boronic ester using an appropriate catalyst, such as bis(triphenylphosphine) palladium(II) dichloride, deprotection using an appropriate acid, such as TFA or HCl, followed by amide formation e.g. of the ammonium salt or the free amine with an acid and using an appropriate coupling reagent, such as T3P, and an appropriate base, such as DIPEA, or with an acid chloride using an appropriate base, such as DIPEA, as shown in Scheme 3 below:

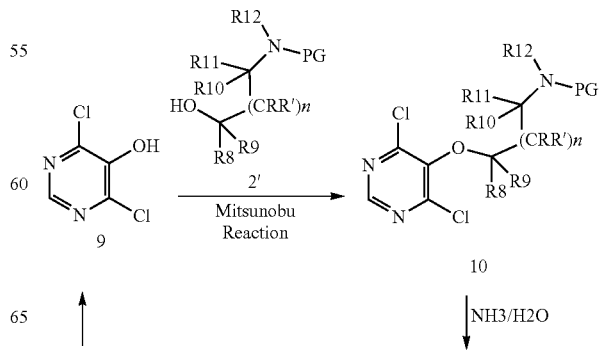

-continued

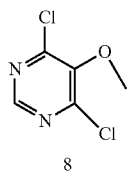
8

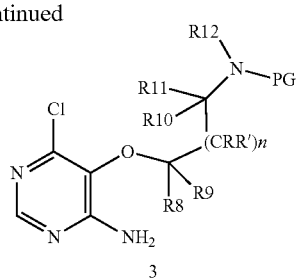
3

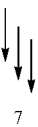

7

Example 38

N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide

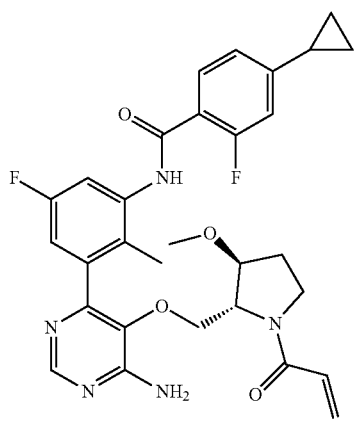 [SMILES: C=CC(=O)N1CC[C@H](OC)[C@H]1COc1c(N)ncnc1-c1cc(F)cc(NC(=O)c2ccc(C3CC3)cc2F)c1C]

(1) 4,6-Dichloropyrimidin-5-ol, INT 37

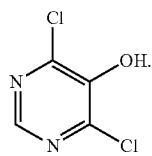

To a solution of 4,6-dichloro-5-methoxypyrimidine (5.00 g, 27.93 mmol) in DCE (80 mL) at 0° C. was added aluminum chloride (5.48 g, 41.10 mmol) in one portion. The reaction mixture was stirred vigorously at 50° C. for 6 hr. The mixture was cooled to 0° C. and aqueous HCl solution (1 M, 40 mL) followed by MeOH (10 mL) were added slowly. The mixture was stirred vigorously at RT for 10 min, then diluted with water and extracted with a mixture of DCM/MeOH (10:1, 2×100 mL) and EtOAc (1×100 mL). The combined organic layers were dried over sodium sulfate, filtered and concentrated to afford crude INT 37 as beige solid.

UPLC-MS: MS (ESI): [M−H]⁻ 163.0, rt=0.45 min. $^1$H NMR (DMSO-d$_6$): δ (ppm) 11.71 (s, br, 1H), 8.39 (s, 1H).

(2) (2S,3S) 2-Methyl N-Boc-3-hydroxypyrrolidine-2-carboxylate, INT 38

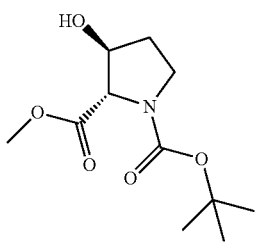 [SMILES: COC(=O)[C@@H]1[C@@H](O)CCN1C(=O)OC(C)(C)C]

To a solution of (2S,3S)—N-Boc-3-hydroxypyrrolidine-2-carboxylic acid (4.10 g, 17.73 mmol) in DMF (100 mL) at 0° C. was added potassium carbonate (4.00 g, 28.94 mmol) followed by iodomethane (1.3 mL, 20.79 mmol). The reaction mixture was warmed to RT and stirred at RT for 4 hr, then at 90° C. for 1 hr. After cooling to RT iodomethane (0.70 mL, 11.19 mmol) was added and the reaction mixture was stirred at RT overnight. The mixture was diluted with brine and extracted with EtOAc (3×). The combined organic layers were dried over sodium sulfate, filtered and concentrated. The residue was purified by flash chromatography (silica; cyclohexane/EtOAc gradient, 0-50%) to afford INT 38 as a colorless oil.

MS (ESI): [M+H]⁺ 246.2. $^1$H NMR (CDCl$_3$): δ (ppm) rotamers 4.42 (s, br, 1H), 4.29 and 4.18 (s, total 1H), 3.74 (s, 3H), 3.66-3.53 (m, 3H), 2.13-2.03 (m, 1H), 1.97-1.88 (m, 1H), 1.46 and 1.41 (5, total 9H).

(3) (2S,3S) 2-Methyl N-Boc-3-methoxypyrrolidine-2-carboxylate, INT 39

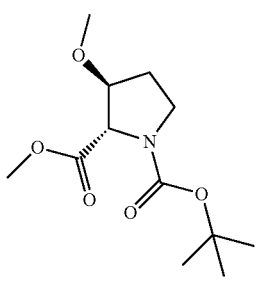 [SMILES: COC(=O)[C@@H]1[C@@H](OC)CCN1C(=O)OC(C)(C)C]

To a solution of INT 38 (2.53 g, 10.33 mmol) in DMF (25.0 mL) was added iodomethane (3.2 mL, 51.60 mmol) followed by silver(I) oxide (7.18 g, 31.00 mmol). The reaction mixture was stirred at RT over the weekend. The mixture was diluted with EtOAc and filtered through a pad of Celite. The filtrate was washed with brine, aqueous 10% sodium thiosulfate solution and saturated aqueous sodium hydrogen carbonate solution. The organic layer was dried over sodium sulfate, filtered and concentrated to afford crude INT 39 as a colorless oil.

¹H NMR (CDCl₃): δ (ppm) rotamers 4.41 and 4.26 (s, total 1H), 3.94-3.87 (m, br, 1H), 3.75 (s, 3H), 3.69-3.53 (m, 2H), 3.38 (s, 3H), 2.11-1.95 (m, 2H), 1.46 and 1.41 (s, total 9H).

(4) (2R,3S)—N-Boc-2-hydroxymethyl-3-methoxypyrrolidine, INT 40

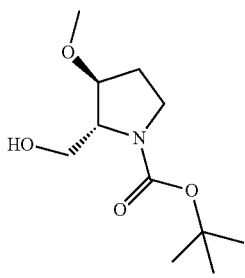 [SMILES: CO[C@H]1CCN(C(=O)OC(C)(C)C)[C@@H]1CO]

To a solution of INT 39 (2.28 g, 8.81 mmol) in THF (25 mL) was added lithium chloride (1.12 g, 26.40 mmol) followed by sodium borohydride (1.00 g, 26.40 mmol). EtOH (50 mL) was added and the reaction mixture was stirred at RT for 4 hr. The mixture was cooled to 0° C. and water was added slowly. The mixture was extracted with EtOAc. The organic layer was washed with brine, dried over sodium sulfate, filtered and concentrated. The aqueous layer diluted with saturated aqueous ammonium chloride solution and back-extracted with EtOAc. The organic layer was washed with brine, dried over sodium sulfate, filtered and concentrated. The combined residues were purified by flash chromatography (silica; cyclohexane/EtOAc gradient, 15-100%) to afford INT 40 as a colorless liquid.

MS (ESI): [M+H]⁺ 232.2. ¹H NMR (CDCl₃); δ (ppm) rotamers 4.03-3.92 and 3.89-3.77 (m, br, total 2H), 3.72-3.55 (m, br, 2H), 3.52-3.30 (overlapping m, 2H and s, 3H), 2.01-1.92 (m, br, 2H), 1.47 (s, 9H).

(5) (2R,3S)-tert-Butyl 2-(((4,6-dichloropyrimidin-5-yl)oxy)methyl)-3-methoxypyrrolidine-1-carboxylate, INT 41

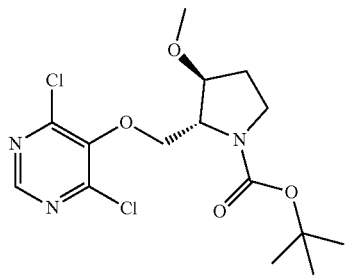 [SMILES: CO[C@H]1CCN(C(=O)OC(C)(C)C)[C@@H]1COc1c(Cl)ncnc1Cl]

To a solution of INT 37 (105 mg, 0.64 mmol) and INT 40 (221 mg, 0.96 mmol) in THF (12 mL) was added triphenylphosphine (250 mg, 0.96 mmol) followed by the dropwise addition of DIAD (0.186 mL, 0.96 mmol). The reaction mixture was stirred at 60° C. overnight. The mixture was concentrated under reduced pressure. The residue was purified by flash chromatography (silica; cyclohexane/EtOAc gradient, 0-40%) to afford INT 41 as a colorless residue.

UPLC-MS: MS (ESE): [M+H–tBu]⁺ 322.1, rt=1.17 min. ¹H NMR (CDCl₃): δ (ppm) rotamers 8.57 and 8.54 (s, total 1H), 4.35-3.91 (m, 4H), 3.58-3.46 (m, 2H), 3.42 (s, 3H), 2.24-1.97 (m, 2H), 1.46 (s, 9H).

(6) (2R,3S)-tert-Butyl 2-(((4-amino-6-chloropyrimidin-5-yl)oxy)methyl)-3-methoxypyrrolidine-1-carboxylate, INT 42

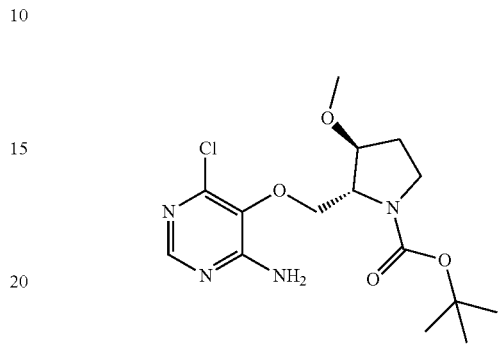

To a solution of INT 41 (173 mg, 0.46 mmol) in 2-propanol (5.0 mL) was added aqueous 33% ammonium hydroxide solution (2.7 mL, 22.63 mmol). The reaction mixture was stirred in a sealed tube at 80° C. for 5 hr. The mixture was concentrated under reduced pressure. The residue was purified by flash chromatography (silica; DCM/EtOAc gradient, 0-50%) to afford INT 42 as a colorless oil.

UPLC-MS: MS (ESI): [M+H]⁺ 359.2, rt=0.92 min. ¹H NMR (CDCl₃): δ (ppm) rotamers 8.08 (s, 1H), 6.22 and 5.78 (s, br, total 2H), 4.25-3.95 (m, br, 4H), 3.61-3.37 (m, 5H, including s, 3H, at δ 3.40), 2.18-1.95 (m, 2H), 1.46 (s, 9H).

(7) N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide, INT 43

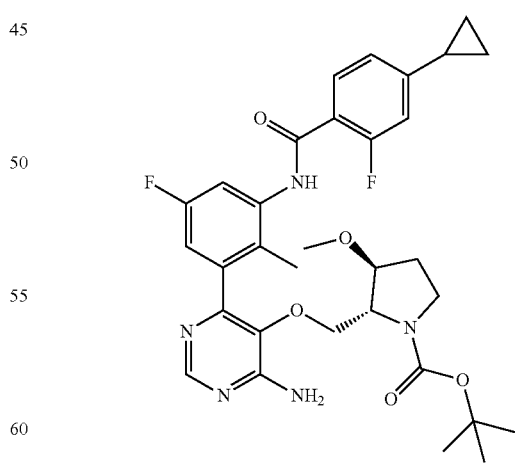

INT 43 was prepared according to Scheme 3 following a procedure analogous to step 2 of Example 6 replacing INT 8 with INT 42.

UPLC-MS: MS (ESI): [M+H]⁺ 610.5, rt=1.21 min.

(8) N-(3-(6-Amino-5-(((2R,3S)-3-methoxypyrrolidin-2-yl)methoxy)pyrimidin-4-yl)-5-fluoro-2-methylphenyl)-4-cyclopropyl-2-fluorobenzamide, INT 44

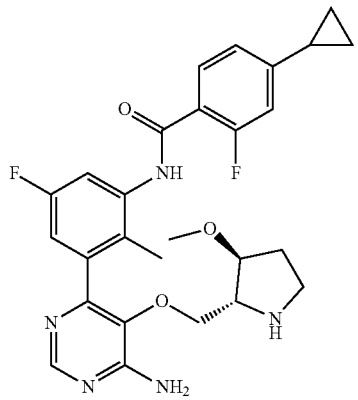 [SMILES: CO[C@H]1CCN[C@@H]1COc1c(N)ncnc1-c1cc(F)cc(NC(=O)c2ccc(C3CC3)cc2F)c1C]

INT 44 was prepared according to Scheme 3 following a procedure analogous to step 3 of Example 6 replacing INT 9 with INT 43 and purifying the crude by flash chromatography (silica; DCM/(MeOH with 2% aqueous ammonium hydroxide) gradient, 5-65%) to afford INT 44 as the free amine.

UPLC-MS: MS (ESI): [M+H]$^+$ 510.3, rt=0.77 min.

(9) N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide The title compound was prepared according to Scheme 3 following a procedure analogous to step 4 of Example 6 replacing INT 10 with INT 44.

UPLC-MS: MS (ESI): [M+H]$^+$ 564.3, rt=0.98 min. $^1$H NMR (CDCl$_3$): δ (ppm) rotamers 8.60 and 8.55 (s, total 1H), 8.42 and 8.36 (s, total 1H), 8.20-8.13 (m, 1H), 8.13-8.04 (m, 1H), 7.07-7.01 (m, 1H), 6.96-6.83 (m, 2H), 6.47-6.32 (m, 2H), 5.79 (s, v br, 2H), 5.72-5.66 (m, 1H), 4.21-4.16 and 3.70-3.42 and 3.33-3.28 (m, total 6H), 3.26 and 3.20 (s, total 3H), 2.15 (s, 3H), 2.01-1.88 (m, 2H), 1.84-1.74 (m, 1H), 1.16-1.07 (m, 2H), 0.84-0.75 (m, 2H).

Alternatively, agents of the invention may be prepared by a reaction sequence involving alkylation of 4,6-dichloro-5-hydroxy-pyrimidine 9 with benzyl bromide using an appropriate base, such as potassium carbonate, followed by nucleophilic aromatic substitution with ammonium hydroxide to yield the aminopyrimidine 12, Suzuki coupling with a boronic ester 4 using an appropriate catalyst, such as bis(triphenylphosphine)-palladium(II) dichloride to yield the benzylated intermediate 13. Cleavage of the benzyl group, e.g. by hydrogenation, followed by a Mitsunobu reaction of the pyrimidinol with an alcohol of formula 2' using an appropriate azodicarboxylate, such as DIAD, and Smopex-301 or triphenylphosphine, deprotection using an appropriate acid, such as TFA or HCl, followed by amide formation of the ammonium salt or the free amine with an acid using an appropriate coupling reagent, such as T3P, and an appropriate base, such as DIPEA, or with an acid chloride using an appropriate base, such as DIPEA, to yield a final compound of the invention, i.e. a compound of formula 7, as shown in Scheme 4 below:

Scheme 4:

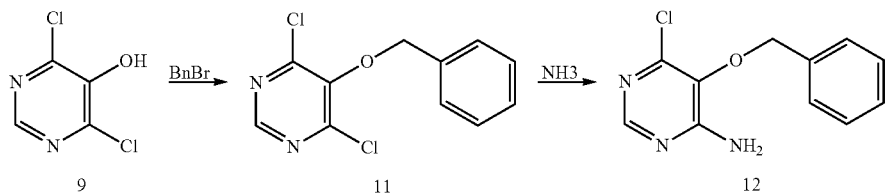

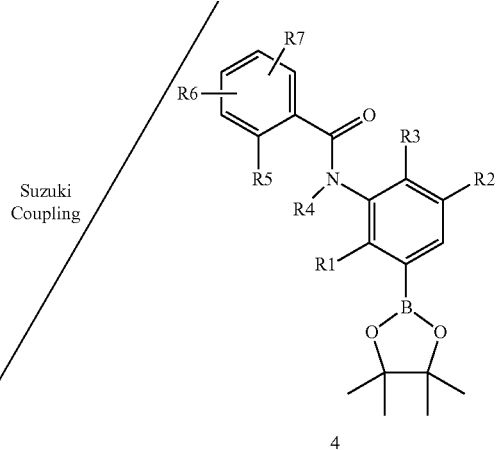

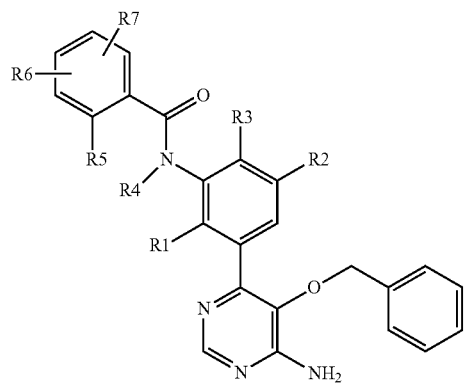
13
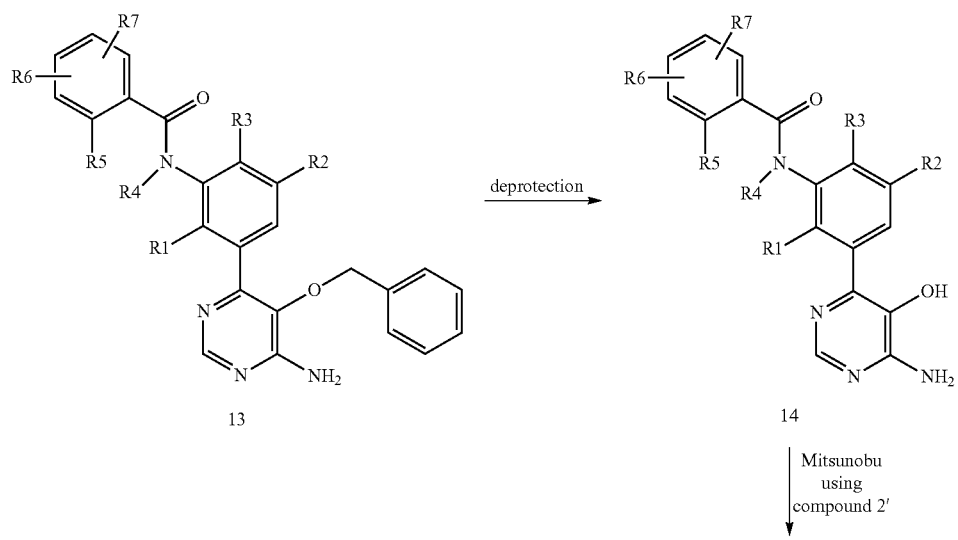
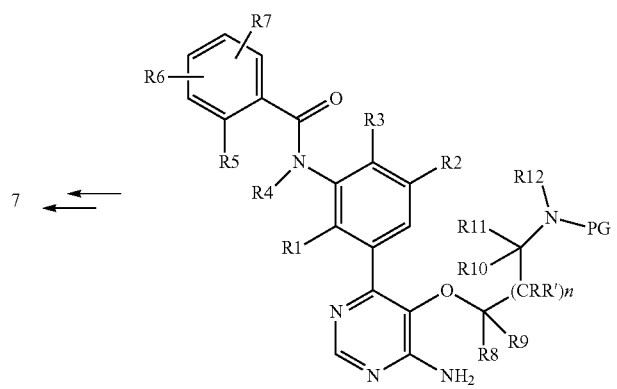

Example 39

N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide

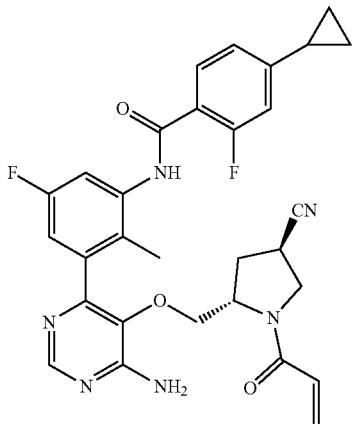 [SMILES: C=CC(=O)N1C[C@H](C#N)C[C@H]1COc1c(N)ncnc1-c1cc(F)cc(NC(=O)c2ccc(C3CC3)cc2F)c1C]

(1) 5-(Benzyloxy)-4,6-dichloropyrimidine, INT 45

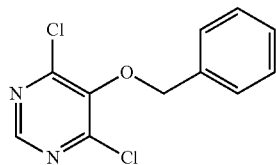 [SMILES: Clc1ncnc(Cl)c1OCc1ccccc1]

To a solution of INT 37 (content 90%, 6.50 g, 35.50 mmol) in DMF (120 mL) was added benzyl bromide (8.42 mL, 70.90 mmol) followed by potassium carbonate (14.70 g, 106.36 mmol). The reaction mixture was stirred at 60° C. for 1 hr. The mixture was concentrated. The residue was partitioned between EtOAc and water. The organic layer was washed with water and brine, dried over magnesium sulfate, filtered and concentrated. The residue was purified by flash chromatography (silica; cyclohexane/EtOAc gradient, 0-10%) to afford INT 45 as a colorless oil.

UPLC-MS: MS (ESI): $[M+H]^+$ 255.1, rt=1.15 min. $^1$H NMR (DMSO-$d_6$): δ (ppm) 8.72 (s, 1H), 7.57-7.50 (m, 2H), 7.48-7.37 (m, 3H), 5.19 (s, 2H), (2) 5-(Benzyloxy)-6-chloropyrimidin-4-amine, INT 46

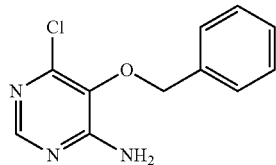 [SMILES: Nc1ncnc(Cl)c1OCc1ccccc1]

To a solution of INT 45 (8.24 g, 32.30 mmol) in 2-propanol (100 mL) was added aqueous 26% ammonium hydroxide solution (93 mL, 614 mmol) in an autoclave. The reaction mixture was stirred at 80° C. for 12 hr. The mixture was concentrated. The residue was partitioned between EtOAc and water. The organic layer was washed with brine, dried over magnesium sulfate, filtered and concentrated to afford crude INT 46 as a white solid.

UPLC-MS: MS (ESI): $[M+H]^+$ 236.1, rt=0.84 min. $^1$H NMR (DMSO-$d_6$): δ (ppm) 7.98 (s, 1H), 7.58-7.51 (m, 2H), 7.43-7.32 (m, 3H), 7.25 (s, br, 2H), 4.95 (s, 2H).

(3) N-(3-(6-Amino-5-(benzyloxy)pyrimidin-4-yl)-5-fluoro-2-methylphenyl)-4-cyclopropyl-2-fluorobenzamide, INT 47

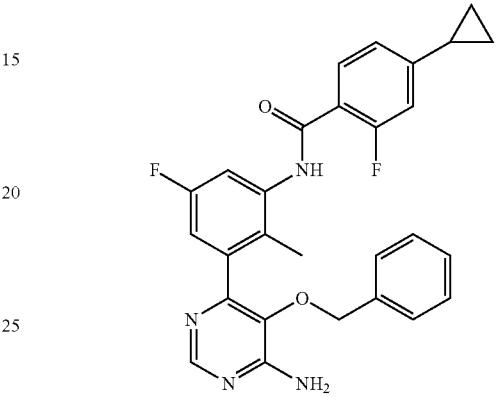

To a solution of INT 46 (content 90%, 500 mg, 1.91 mmol) in DME (7.0 mL) and water (1.0 mL) was added INT 5 (947 mg, 2.29 mmol) followed by aqueous sodium carbonate solution (2 M, 2.86 mL, 5.73 mmol). The mixture was degassed with argon for 10 min, then. bis(triphenylphosphine)palladium(II) dichloride (67.0 mg, 0.095 mmol) was added and the reaction mixture was stirred at 120° C. for 15 min in a microwave reactor. The mixture was partitioned between saturated aqueous sodium hydrogen carbonate solution and EtOAc. The organic layer was washed with water and brine, dried over magnesium sulfate, filtered and concentrated. The residue was purified by flash chromatography (silica; DCM/EtOAc gradient, 0-100%) to afford INT 47 as a yellow solid.

UPLC-MS: MS (ESI): $[M+H]^+$ 487.4, rt=1.15 min. $^1$H NMR (DMSO-$d_6$): δ (ppm) 9.80 (s, 1H), 8.20 (s, 1H), 7.66 (t, 1H), 7.54 (d, 1H), 7.26-7.18 (m, 3H), 7.11-6.91 (m, 7H), 4.55 (s, 2H), 2.08-1.95 (overlapping s and m, total 4H), 1.10-1.01 (m, 2H), 0.85-0.74 (m, 2H).

(4) N-(3-(6-Amino-5-hydroxypyrimidin-4-yl)-5-fluoro-2-methylphenyl)-4-cyclopropyl-2-fluorobenzamide, INT 48

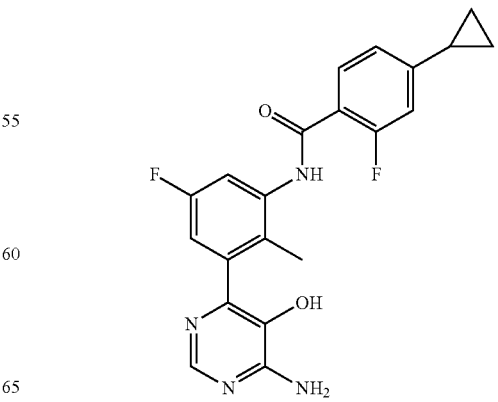

To a solution of INT 47 (1.16 g, 2.38 mmol) in THF (20 mL) was added Pd—C (116 mg). The reaction mixture was hydrogenated at RT and normal pressure for 48 hr. The mixture was diluted with MeOH (10 mL) and filtered over a pad of Celite. The filtrate was concentrated. The residue was suspended in DCM (20 mL) and TFA (0.918 mL, 11.92 mmol) was added. The mixture was stirred at RT for 30 min, then poured into a mixture of saturated aqueous sodium hydrogen carbonate solution and EtOAc. The organic layer was washed with brine, dried over magnesium sulfate, filtered and concentrated to afford INT 48 as a beige solid.

UPLC-MS: MS (ESI): [M+H]$^+$ 397.2, rt=0.80 min. $^1$H NMR (DMSO-d$_6$): δ (ppm) 9.76 (s, 1H), 8.74 (s, 1H), 8.02 (s, 1H), 7.65 (t, 1H), 7.59-7.48 (m, 1H), 7.12-7.03 (m, 2H), 6.98-6.91 (m, 1H), 6.66 (s, br, 2H), 2.11-1.94 (overlapping s and m, total 4H), 1.14-0.98 (m, 2H), 0.87-0.71 (m, 2H).

(5) (2S,4S)-2-Methyl N-Boc-4-((methylsulfonyl)oxy)pyrrolidine-2-carboxylate, INT 49

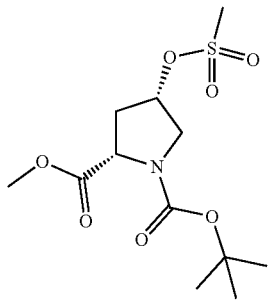 [SMILES: COC(=O)[C@@H]1C[C@H](OS(C)(=O)=O)CN1C(=O)OC(C)(C)C]

To a solution of (2S,4S)-methyl N-Boc-4-hydroxypyrrolidine-2-carboxylate (11.50 g, 46.88 mmol) in DCM (100 mL) was added DIPEA (9.70 mL, 55.54 mmol) followed by methanesulfonyl chloride (4.30 mL, 55.18 mmol). The reaction mixture was stirred at RT overnight. More DIPEA (1.50 mL, 8.59 mmol) and methanesulfonyl chloride (0.60 mL, 7.70 mmol) were added and the reaction mixture was stirred at RT for an additional hour. The mixture was concentrated. The residue was purified by flash chromatography (silica; DCM/EtOAc gradient, 5-15%) followed by a second purification by flash chromatography (silica; cyclohexane/EtOAc gradient, 0-100%) to afford INT 49 as a yellow oil.

MS (ESI): [M+H]$^+$ 324.2. $^1$H NMR (CDCl$_3$): δ (ppm) rotamers 5.24 (m, br, 1H), 4.55-4.48 and 4.44-4.37 (m, total 1H), 3.84-3.70 (overlapping s and m, total 5H), 3.02 (s, 3H), 2.58-2.47 (m, br, 2H), 1.48 and 1.43 (s, total 9H).

(6) (2S,4S)—N-Boc-2-(hydroxymethyl)-4-((methylsulfonyl)oxy)pyrrolidine, INT 50

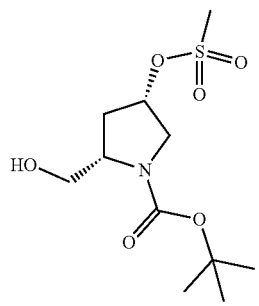 [SMILES: CC(C)(C)OC(=O)N1C[C@@H](OS(C)(=O)=O)C[C@H]1CO]

To a solution of INT 49 (12.52 g, 38.72 mmol) in THF (100 mL) at 0° C. was added dropwise lithium borohydride solution (2 M in THF, 67.6 mL, 135.00 mmol). The reaction mixture was stirred overnight and allowed to warm up to RT. The mixture was cooled to 0° C. and water was added slowly. The mixture was extracted with EtOAc, the organic layer was washed with brine, dried over sodium sulfate, filtered and concentrated. The aqueous layer was diluted with saturated aqueous ammonium chloride solution and back-extracted with EtOAc. The organic layer was washed with brine, dried over sodium sulfate, filtered and concentrated. The two residues were combined and purified by flash chromatography (silica; cyclohexane/EtOAc gradient, 25-100%; followed by EtOAc/MeOH gradient, 0-10%) to afford INT 50 as a colorless resin.

MS (ESI): [M+H–tBu]$^+$ 240.1. $^1$H NMR (CDCl$_3$): δ (ppm) rotamers 5.15-5.10 (m, br, 1H), 4.37-4.29 and 4.07-3.87 (m, total 2H), 3.81-3.62 (m, 2H), 3.59-3.47 (m, 2H), 3.00 (s, 3H), 2.37-2.25 and 2.11-2.02 (m, total 2H), 1.40 and 1.38 (s, total 9H).

(7) (2S,4S)—N-Boc-2-((tert-butyldiphenylsilyl)oxymethyl)-4-((methylsulfonyl)oxy)-pyrrolidine, INT 51

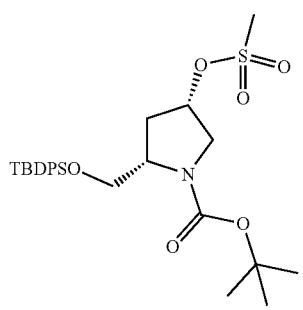

To a solution of INT 50 (11.00 g, 37.24 mmol) in DCM (100 mL) was added imidazole (4.30 g, 63.16 mmol) followed by tert-butylchlorodiphenylsilane (11.0 mL, 42.82 mmol). The reaction mixture was stirred at RT for 3 hr. The suspension was filtered over a thin layer of Celite. The filtrate was washed with water and brine, dried over sodium sulfate, filtered and concentrated. The residue was purified by flash chromatography (silica; cyclohexane/EtOAc gradient, 0-50%) to afford INT 51 as a colorless oil.

UPLC-MS: MS (ESI): [M+H–tBu]$^+$ 534.3, rt=1.50 min. $^1$H NMR (CDCl$_3$): δ (ppm) rotamers 7.69-7.62 (m, 4H), 7.45-7.35 (m, 6H), 5.28-5.16 (m, br, 1H), 4.17-4.07 and 4.05-3.97 (m, total 1H), 3.94-3.87 (m, 1H), 3.87-3.80 (m, 1H), 3.64-3.50 (m, 2H), 2.91 (s, br, 3H), 2.71-2.61 and 2.40-2.30 (m, total 2H), 1.43 and 1.33 (s, total 9H), 1.06 (s, 9H).

(8) (2S,4R)—N-Boc-2-((tert-butyldiphenylsilyl)oxymethyl)-4-(cyano)pyrrolidine, INT 52

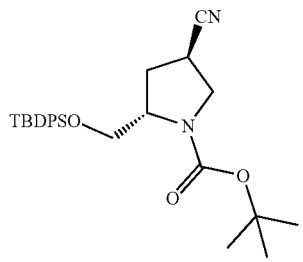

To a solution of INT 51 (5.06 g, 9.48 mmol) in DMF (75 mL) was added sodium cyanide (1.39 g, 28.40 mmol). The reaction mixture was stirred at 100° C. for 3 hr. The mixture was partitioned between EtOAc and water. The organic layer was washed with brine, dried over sodium sulfate, filtered and concentrated. The residue was purified by flash chromatography (silica; cyclohexane/EtOAc gradient, 0-25%) to afford INT 52 as a colorless resin.

$^1$H NMR (CDCl$_3$): δ (ppm) rotamers 7.65-7.55 (m, 4H), 7.47-7.31 (m, 6H), 4.13-4.05 and 4.02-3.91 and 3.78-3.57 (m, total 5H), 3.39-3.29 (m, 1H), 2.52-2.21 (m, 2H), 1.48 and 1.34 (s, total 9H), 1.05 (s, 9H).

(9) (2S,4R)—N-Boc-2-(hydroxymethyl)-4-(cyano) pyrrolidine, INT 53

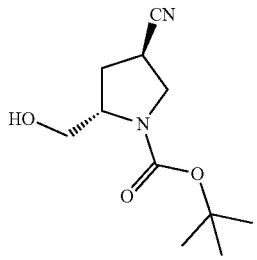 [SMILES: CC(C)(C)OC(=O)N1C[C@H](C#N)C[C@H]1CO]

To a solution of INT 52 (2.95 g, 6.35 mmol) in THF (30 mL) was added TBAF (1.0 M in THF, 7.5 mL, 7.50 mmol). The reaction mixture was stirred at AT for 2.5 hr. The mixture was concentrated and the residue was taken up in EtOAc. The organic phase was washed with water and brine, dried over sodium sulfate, filtered and concentrated. The residue was purified by flash chromatography (silica; cyclohexane/EtOAc gradient, 0-100%) to afford INT 53 as a colorless residue.

MS (ESI): [M+H−tBu]$^+$ 171.1. NMR (CDCl$_3$): δ (ppm) 4.14-3.83 (m, br, 2H), 3.75-3.53 (m, 4H), 3.35-3.19 (m, br, 1H), 2.40-2.26 and 2.23-2.10 (m, total 2H), 1.47 (s, 9H).

(10) (2S,4R)-tert-Butyl 2-(((4-amino-6-(3-(4-cyclopropyl-2-fluorobenzamido)-5-fluoro-2-methylphenyl)pyrimidin-5-yl)oxy)methyl)-4-cyanopyrrolidine-1-carboxylate, INT 54

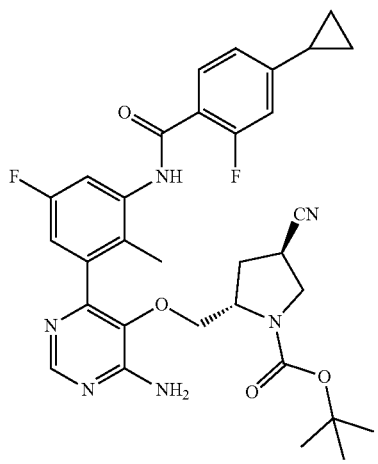 [SMILES: Cc1c(NC(=O)c2ccc(C3CC3)cc2F)cc(F)cc1-c1ncnc(N)c1OC[C@@H]1C[C@@H](C#N)CN1C(=O)OC(C)(C)C]

To a solution of INT 48 (240 mg, 0.61 mmol) and INT 53 (274 mg, 1.21 mmol) in THF (15 mL) was added SMOPEX-301 (1 mmol/g, 1.51 g, 1.51 mmol). The mixture was heated to 60° C. and DIAD was added dropwise at this temperature. The reaction mixture was stirred at 60° C. for 2 hr. The mixture was filtered through a pad of Celite, the filtrate was concentrated. The residue was purified by flash chromatography (silica; TBME/EtOAc gradient, 0-100%) to afford INT 54 as a colorless oil.

UPLC-MS: MS (ESL): [M+H]$^+$ 605.3, rt=1.14 min.

(11) N-(3-(6-Amino-5-(((2S,4R)-4-cyanopyrrolidin-2-yl)methoxy)pyrimidin-4-yl)-5-fluoro-2-methylphenyl)-4-cyclopropyl-2-fluorobenzamide, INT 55

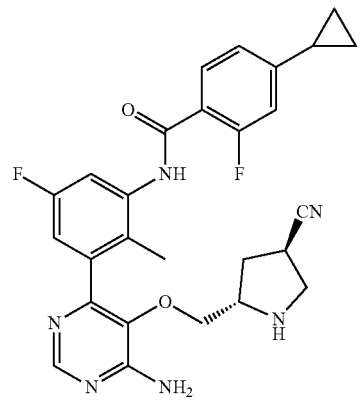 [SMILES: Cc1c(NC(=O)c2ccc(C3CC3)cc2F)cc(F)cc1-c1ncnc(N)c1OC[C@@H]1C[C@@H](C#N)CN1]

To a solution of INT 54 (content 83%, 313 mg, 0.43 mmol) in DCM (10 mL) was added TFA (1.0 mL, 12.98 mmol) followed by one drop of water. The reaction mixture was stirred at RT for 1.5 hr. The mixture was concentrated. The residue was purified by flash chromatography (silica; DCM/(MeOH with 2% aqueous ammonium hydroxide) gradient, 0-40%) to afford INT 55 as the free amine as a colorless residue.

UPLC-MS: MS (ESI): [M+H]$^+$ 505.3, rt=0.75 min.

(12) N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide

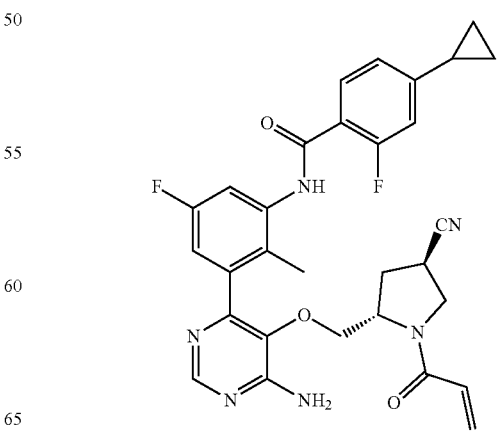

To a solution of INT 55 (102 mg, 0.20 mmol) and DIPEA (0.200 mL, 1.15 mmol) in DCM (4.0 mL) at 0° C. was slowly added dropwise acryloyl chloride (0.020 mL, 0.24 mmol). The reaction mixture was stirred at 0° C. for 30 min. The mixture was concentrated. The residue was purified by flash chromatography (silica; EtOAc/MeOH gradient, 0-20%), followed by SFC purification to afford Example 39 as white solid after lyophilization.

UPLC-MS: MS (ESI): [M+H]$^+$ 559.4, rt=0.96 min. $^1$H NMR (DMSO-d$_6$): δ (ppm) rotamers 9.81 (s, 1H), 8.21 (d, 1H), 7.72-7.63 (m, 1H), 7.57-7.47 (m, 1H), 7.17-6.91 (m, 5H), 6.48-6.39 and 6.32-6.21 (m, total 1H), 6.15-6.05 (m, 1H), 5.68-5.56 (m, 1H), 4.29-4.22 and 4.18-4.12 (m, total 1H), 3.73-3.62 and 3.53-3.45 (m, total 3H), 3.35-3.25 and 3.17-3.08 (m, total 2H), 2.26-1.95 (overlapping m and s, total 6H), 1.10-1.01 (m, 2H), 0.85-0.75 (m, 2H).

Example 40

N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide

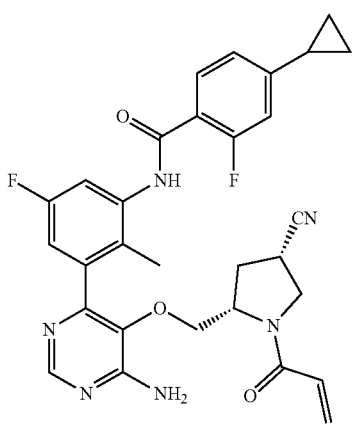

The title compound was prepared according to Scheme 4 following a procedure analogous to Example 39 replacing (2S,4S)-methyl N-Boc-4-hydroxypyrrolidine-2-carboxylate with (2S,4R)-methyl N-Boc-4-hydroxypyrrolidine-2-carboxylate in step 5.

UPLC-MS: MS (ESI): [M+H]$^+$ 559.4, rt=0.94 min.

Biological Part

Inhibition of Btk Enzymatic Activity

The inhibitory activity of the present compounds against Btk was assessed in a biochemical enzyme assay. Assay plates in 384 well format were prepared with 8-point serial dilutions for the test compounds on a Thermo CatX workstation equipped with a Innovadyne Nanodrop Express. The assay plates were prepared by addition of 50 nl per well of compound solution in 90% DMSO. The kinase reactions were started by stepwise addition of 4.5 µl per well of peptide/ATP-solution (4 µM FITC-Ahx-TSELKKVVALYDYMPMNAND-NH2, 164 µM ATP) in kinase buffer (50 mM HEPES, pH 7.5, 1 mM DTT, 0.02% Tween20, 0.02% BSA, 0.6% DMSO, 10 mM beta-glycerophosphate, and 10 µM sodium orthovanadate, 18 mM MgCl2, 1 mM MnCl2) and 4.5 µl per well of enzyme solution (6.4 nM full-length human recombinant BTK) in kinase buffer. Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Kinase reactions were analyzed on a Caliper LC3000 workstation by separating phosphorylated and unphosphorylated peptides and kinase activities were calculated from the amounts of newly formed phospho-peptide. Inhibition data were calculated by comparison to control reactions without enzyme (100% inhibition) and without inhibitors (0% inhibition). The concentration of inhibitor required for 50% inhibition (IC50) was calculated from the inhibition in response to inhibitor concentrations.

| Example | Inhibition of Btk enzymatic activity IC$_{50}$ [uM] |
| --- | --- |
| Example 1 | 0.002 |
| Example 2 | 0.038 |
| Example 3 | 0.001 |
| Example 4 | 0.009 |
| Example 5 | 0.004 |
| Example 6 | 0.001 |
| Example 7 | 0.042 |
| Example 8 | 0.002 |
| Example 9 | 0.01 |
| Example 10 | 0.004 |
| Example 11 | 0.01 |
| Example 12 | 0.012 |
| Example 13 | 0.007 |
| Example 14 | 0.001 |
| Example 15 | 0.001 |
| Example 16 | 0.015 |
| Example 17 | 0.005 |
| Example 18 | 0.001 |
| Example 19 | 0.016 |
| Example 20 | 0.005 |
| Example 21 | 0.002 |
| Example 22 | <0.0001 |
| Example 23 | 0.001 |
| Example 24 | 0.0005 |
| Example 25 | 0.001 |
| Example 26 | 0.0004 |
| Example 27 | 0.003 |
| Example 28 | 0.001 |
| Example 29 | 0.004 |
| Example 30 | 0.006 |
| Example 31 | 0.002 |
| Example 32 | 0.004 |
| Example 33 | 0.001 |
| Example 34 | 0.002 |
| Example 35 | 0.002 |
| Example 36 | 0.017 |
| Example 37 | 0.032 |
| Example 38 | 0.002 |
| Example 39 | 0.001 |
| Example 40 | 0.002 |

Inhibition of Btk Activity in Blood

Alternatively, the inhibitory activity of the present compounds in blood was assessed in the following in vitro B cell activation assay. Whole blood was collected from the abdominal aorta of anaesthetized adult male Lewis rats and was anticoagulated with 100 U/ml sodium heparin. Blood was then diluted to 50% with high glucose DMEM (Amimed) supplemented with 100 U/ml penicillin, 100 mg/ml streptomycin, 2 mM L-glutamin, 50 mg/ml dextran 40 and 5% FCS (Fetaclone I, Gibco). Then, 190 µl prediluted blood was mixed in 96 well U-bottomed microtiter plates (Nunc) with 10 µl of serial dilutions of test compounds in DMSO. Cultures were incubated at 37° C., 5% CO2 for 1 hour, then 30 µl of rat IL-4 (Beckton-Dickinson, final concentration 5 ng/ml) and goat anti-rat IgM (Serotec, final concentration 15 ug/ml) were added and the cultures were incubated for 24 hours. Activation of B cells was measured by flow cytometry after staining for the B cell subset with PE-Cy5-labeled anti-ratCD45RA (Beckton-Dickinson) and for the activation marker CD86 (RE-labeled anti-rat CD86 (Beckton-Dickinson). All staining procedures were performed at RT for 30 min in the dark in 96-deep well V-bottomed microtiter plates (Corning) with BD Lysing Solution (Beckton-Dickinson).

Cytometric data was acquired on a FACScalibur flow cytometer (BD Biosciences) and the subpopulation of lymphocytes were gated according to size and granularity and further analyzed for expression of CD45RA and the activation markers. Data for the inhibition of B cell activation were calculated from the percentage of cells positively stained for activation markers within the CD45RA positive population. Inhibition data were calculated by comparison to control cultures without anti-IgM and IL-4 (100% inhibition) and without inhibitors (0% inhibition). The concentration of inhibitor required for 50% inhibition (IC50) was calculated from the inhibition in response to inhibitor concentrations.

| Example | Inhibition of Btk activity in blood $IC_{50}$ [uM] |
|---|---|
| 1 | 0.112 |
| 2 | 1.111 |
| 3 | 0.124 |
| 4 | 0.376 |
| 5 | 0.201 |
| 6 | 0.023 |
| 7 | 0.983 |
| 8 | 0.048 |
| 9 | 0.240 |
| 10 | 0.161 |
| 11 | 0.323 |
| 12 | 0.459 |
| 13 | 0.105 |
| 14 | 0.028 |
| 15 | 0.029 |
| 16 | 0.558 |
| 17 | 0.246 |
| 18 | 0.419 |
| 19 | 0.136 |
| 20 | 0.330 |
| 21 | 0.090 |
| 22 | 0.057 |
| 23 | 0.057 |
| 24 | 0.032 |
| 25 | 0.065 |
| 26 | 0.051 |
| 27 | 0.076 |
| 28 | 0.033 |
| 29 | 0.134 |
| 30 | 0.222 |
| 31 | 0.025 |
| 32 | 0.055 |
| 33 | 0.050 |
| 34 | 0.208 |
| 35 | 0.072 |
| 36 | 0.354 |
| 37 | 0.968 |
| 38 | 0.070 |
| 39 | 0.176 |
| 40 | 0.080 |

Utilities

Based for example upon the biological test results, compounds of the invention may generally be useful in the treatment of an indication selected from: Autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

In a further embodiment, the therapy is selected from a disease which may be treated by an antagonist of Bruton's tyrosine kinase.

In another embodiment, the invention provides a method of treating a disease which is treated by the modulation of Btk-comprising administration of a therapeutically acceptable amount of a compound of formula (I) or a salt thereof. In a further embodiment, the disease is selected from the afore-mentioned lists Combinations The compound of the present invention may be administered either simultaneously with, or before or after, one or more other therapeutic agent. The compound of the present invention may be administered separately, by the same or different route of administration, or together in the same pharmaceutical composition as the other agents.

The compounds of formula (I) may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent. For example, the compounds of formula (I) may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, AP23464, AP23675, AP23841, TAFA-93, biolimus-7 or biolimus-9; an ascomycin having immunosuppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154),

[4-(3',5'-dibromo-4'-hydroxyphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g., mono-citrate (also called CP-690,550), or a compound as disclosed in WO 04/052359 or WO 05/066156; sphingosine-1-phosphate receptor modulators such as FTY720 (fingolimod), or compounds disclosed in WO 2005/000833; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LEA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent. Further combination partners to a compound of formula (I) may be selected from a PI3K inhibitor (e.g. pan, or alpha, beta, gamma, delta selectives), TNF inhibitors, IL1beta inhibitors, IL17 inhibitors, and inhibitors of IL6 or IL receptor.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a co-agent, are both administered to a patient simultaneously in the form of a single entity or dosage. The term "non-fixed combination" means that the active ingredients, e.g. a compound of formula (I) and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by Btk kinases. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by Btk kinases, wherein the medicament is prepared for administration with another therapeutic agent. The invention also provides the use of another therapeutic agent for treating a disease or condition mediated by Btk, wherein the medicament is administered with a compound of formula (I).

The invention also provides a compound of formula (I) for use in a method of treating a disease or condition mediated by Btk, wherein the compound of formula (I) is prepared for administration with another therapeutic agent. The invention also provides another therapeutic agent for use in a method of treating a disease or condition mediated by Btk, wherein the other therapeutic agent is prepared for administration with a compound of formula (I). The invention also provides a compound of formula (I) for use in a method of treating a disease or condition mediated by Btk, wherein the compound of formula (I) is administered with another therapeutic agent. The invention also provides another therapeutic agent for use in a method of treating a disease or condition mediated by Btk, wherein the other therapeutic agent is administered with a compound of formula (I).

The invention claimed is:

1. A method of treating a disease which is treated by the modulation of Btk, wherein the method comprising administration of a therapeutically acceptable amount of a compound of formula (I) or a pharmaceutically acceptable salt thereof,

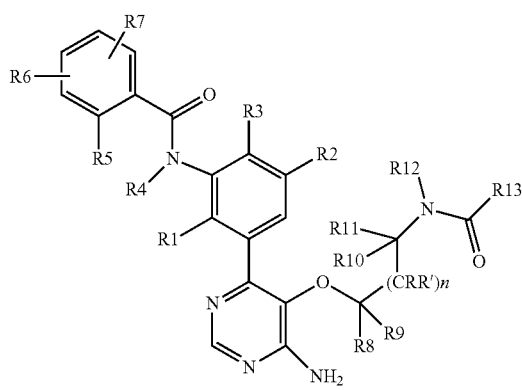

(I)

wherein,
R1 is hydrogen, $C_1$-$C_6$ alkyl optionally substituted by hydroxy;
R2 is hydrogen or halogen;
R3 is hydrogen or halogen;
R4 is hydrogen;
R5 is hydrogen or halogen;
or R4 and R5 are attached to each other and stand for a bond, —$CH_2$—, —$CH_2$—$CH_2$—, —CH=CH—, —CH=CH—$CH_2$—; —$CH_2$—CH=CH—; or —$CH_2$—$CH_2$—$CH_2$—;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R, R', R10 and R11 independently from each other stand for H, or $C_1$-$C_6$ alkyl optionally substituted by $C_1$-$C_6$ alkoxy; or any two of R8, R9, R, R', R10 and R11 together with the carbon atom to which they are bound may form a 3-6 membered saturated carbocyclic ring;
R12 is hydrogen or $C_1$-$C_6$ alkyl optionally substituted by halogen or $C_1$-$C_6$ alkoxy;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl, $C_1$-$C_6$ alkoxy or N,N-di-$C_1$-$C_6$ alkyl amino; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl,
and wherein the disease is rheumatoid arthritis.

2. The method of claim 1, wherein
R1 is hydrogen, or $C_1$-$C_6$ alkyl optionally substituted by hydroxy;
R2 is halogen;
R3 is hydrogen;
R4 is hydrogen;
R5 is halogen;
or R4 and R5 are attached to each other and stand for a bond, —$CH_2$—, —$CH_2$—$CH_2$—, —CH=CH—, —CH=CH—$CH_2$—; —$CH_2$—CH=CH—; or —$CH_2$—$CH_2$—$CH_2$—;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;
R and R' are hydrogen;
R12 is hydrogen or $C_1$-$C_6$ alkyl optionally substituted by halogen;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

3. The method of claim 1, wherein
R1 is hydrogen, or $C_1$-$C_6$ alkyl optionally substituted by hydroxy;
R2 is halogen;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;
R and R' are hydrogen;
R12 is hydrogen or $C_1$-$C_6$ alkyl optionally substituted by halogen;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

4. The method of claim 1, wherein
R1 is hydrogen, $C_1$-$C_6$ alkyl optionally substituted by hydroxy;
R2 is hydrogen or halogen;
R3 is hydrogen or halogen;
R4 and R5 are attached to each other and stand for a bond, —$CH_2$—, —$CH_2$—$CH_2$—, —CH=CH—, —CH=CH—$CH_2$—; —$CH_2$—CH=CH—; or —$CH_2$—$CH_2$—$CH_2$—;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;

R and R' are hydrogen;
R12 is hydrogen or $C_1$-$C_6$ alkyl optionally substituted by halogen;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

5. The method of claim 1, wherein
R1 is hydrogen, $C_1$-$C_6$ alkyl optionally substituted by hydroxy;
R2 is hydrogen or halogen;
R3 is hydrogen or halogen;
R4 and R5 are attached to each other and stand for a —$CH_2$—$CH_2$—, or —CH=CH—;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl; or any two of R8, R9, R10 and R11 together with the carbon atom to which they are bound may form a 3-6 membered saturated carbocyclic ring;
R and R' are hydrogen;
R12 is hydrogen or $C_1$-$C_6$ alkyl optionally substituted by halogen;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

6. The method of claim 1, wherein
R1 is hydrogen, or $C_1$-$C_6$ alkyl optionally substituted by hydroxy;
R2 is halogen;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl;
R and R' are hydrogen;
R12 is hydrogen or $C_1$-$C_6$ alkyl optionally substituted by halogen;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

7. The method of claim 1, wherein
R1 is hydrogen, or $C_1$-$C_6$ alkyl optionally substituted by hydroxy;
R2 is halogen;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8 and R9, independently from each other stand for H, or $C_1$-$C_6$ alkyl;
R and R' are hydrogen;
R12 and any one of R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0 or 1; and
R13 is $C_2$-$C_6$ alkenyl optionally substituted by $C_1$-$C_6$ alkyl or $C_1$-$C_6$ alkoxy; $C_2$-$C_6$ alkynyl optionally substituted by $C_1$-$C_6$ alkyl or $C_1$-$C_6$ alkoxy; or $C_2$-$C_6$ alkylenyl oxide optionally substituted by $C_1$-$C_6$ alkyl.

8. The method of claim 1, wherein
R1 is hydrogen, or $C_1$-$C_6$ alkyl optionally substituted by hydroxy;
R2 is halogen;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8, R9, R10 and R11 independently from each other stand for H, or $C_1$-$C_6$ alkyl;
R and R' are hydrogen;
R12 is hydrogen or $C_1$-$C_6$ alkyl optionally substituted by halogen;
n is 0 or 1; and
R13 is $C_2$-$C_6$ alkenyl optionally substituted by $C_1$-$C_6$ alkyl or $C_1$-$C_6$ alkoxy.

9. The method of claim 1, wherein
R1 is hydrogen, or $C_1$-$C_6$ alkyl optionally substituted by hydroxy;
R2 is fluoro;
R3 is hydrogen;
R4 is hydrogen;
R5 is halogen;
R6 and R7 stand independently from each other for H, $C_1$-$C_6$ alkyl optionally substituted by hydroxyl, $C_3$-$C_6$ cycloalkyl optionally substituted by halogen or hydroxy, or halogen;
R8 and R9 independently from each other stand for H, or $C_1$-$C_6$ alkyl;
R12 and any one of R10 or R11 together with the atoms to which they are bound may form a 4, 5, 6 or 7 membered azacyclic ring, which ring may optionally be substituted by halogen, cyano, hydroxyl, $C_1$-$C_6$ alkyl or $C_1$-$C_6$ alkoxy;
n is 0; and
R13 is $C_2$-$C_6$ alkenyl optionally substituted by $C_1$-$C_6$ alkyl or $C_1$-$C_6$ alkoxy; or $C_2$-$C_6$ alkynyl optionally substituted by $C_1$-$C_6$ alkyl or $C_1$-$C_6$ alkoxy.

10. The method of claim 1, wherein
R1 is $C_1$-$C_6$ alkyl;
R2 is fluoro;
R3 is hydrogen;
R4 is hydrogen;
R5 is fluoro;

R6 and R7 stand independently from each other for H, $C_3$-$C_6$ cycloalkyl, or halogen;

R8, R9, R10 and R11 stand for H;

R12 is hydrogen;

n is 0; and

R13 is $C_2$-$C_6$ alkenyl optionally substituted by $C_1$-$C_6$ alkyl.

11. The method of claim 1, wherein the compound of claim 1, or a pharmaceutically acceptable salt thereof, is selected from:

N-(3-(5-((1-Acryloylazetidin-3-yl)oxy)-6-aminopyrimidin-4-yl)-5-fluoro-2-methylphenyl)-4-cyclopropyl-2-fluorobenzamide;

(E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide;

N-(3-(6-Amino-5-((1-propioloylazetidin-3-yl)oxy)pyrimidin-4-yl)-5-fluoro-2-methylphenyl)-4-cyclopropyl-2-fluorobenzamide;

N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide;

N-(3-(5-((1-Acryloylpiperidin-4-yl)oxy)-6-aminopyrimidin-4-yl)-5-fluoro-2-methylphenyl)-4-cyclopropyl-2-fluorobenzamide;

N-(3-(6-Amino-5-(2-(N-methylacrylamido)ethoxy)pyrimidin-4-yl)-5-fluoro-2-methylphenyl)-4-cyclopropyl-2-fluorobenzamide;

(E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide;

N-(3-(6-Amino-5-(2-(N-methylpropiolamido)ethoxy)pyrimidin-4-yl)-5-fluoro-2-methylphenyl)-4-cyclopropyl-2-fluorobenzamide;

(E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide;

N-(3-(6-Amino-5-(2-(N-methylbut-2-ynarnido)ethoxy)pyrimidin-4-yl)-5-fluoro-2-methylphenyl)-4-cyclopropyl-2-fluorobenzamide;

N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide;

N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide;

N-(3-(5-(2-Acrylamidoethoxy)-6-aminopyrimidin-4-yl)-5-fluoro-2-methylphenyl)-4-cyclopropyl-2-fluorobenzamide;

N-(3-(6-Amino-5-(2-(N-ethylacrylamido)ethoxy)pyrimidin-4-yl)-5-fluoro-2-methylphenyl)-4-cyclopropyl-2-fluorobenzamide;

N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide;

N-(3-(5-((1-Acrylamidocyclopropyl)methoxy)-6-aminopyrimidin-4-yl)-5-fluoro-2-methylphenyl)-4-cyclopropyl-2-fluorobenzamide;

(S)—N-(3-(5-(2-Acrylamidopropoxy)-6-aminopyrimidin-4-yl)-5-fluoro-2-methylphenyl)-4-cyclopropyl-2-fluorobenzamide;

(S)—N-(3-(6-Amino-5-(2-(but-2-ynamido)propoxy)pyrimidin-4-yl)-5-fluoro-2-methylphenyl)-4-cyclopropyl-2-fluorobenzamide;

(S)—N-(3-(6-Amino-5-(2-(N-methylacrylamido)propoxy)pyrimidin-4-yl)-5-fluoro-2-methylphenyl)-4-cyclopropyl-2-fluorobenzamide;

(S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide;

N-(3-(6-Amino-5-(3-(N-methylacrylamido)propoxy)pyrimidin-4-yl)-5-fluoro-2-methylphenyl)-4-cyclopropyl-2-fluorobenzamide;

(S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide;

(S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide;

(S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one;

N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide;

N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide;

N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide;

2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one;

N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide;

N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide;

N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide;

N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide;

(S)—N-(3-(5-((1-Acryloylazetidin-2-yl)methoxy)-6-aminopyrimidin-4-yl)-5-fluoro-2-methylphenyl)-4-cyclopropyl-2-fluorobenzamide;

(S)—N-(3-(6-Amino-5-((1-propioloylazetidin-2-yl)methoxy)pyrimidin-4-yl)-5-fluoro-2-methylphenyl)-4-cyclopropyl-2-fluorobenzamide;

(S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one;

(R)—N-(3-(5-((1-Acryloylazetidin-2-yl)methoxy)-6-aminopyrinnidin-4-yl)-5-fluoro-2-methylphenyl)-4-cyclopropyl-2-fluorobenzamide;

(R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide;

N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide;

N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide;

and

N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

12. The method of claim 1, wherein the compound is
N-(3-(5((1-Acryloylazetidin-3-yl)oxy)-6-aminopyrimidin-4-yl)-5-fluoro-2-methylphenyl)-4-cyclopropyl-2-fluorobenzamide;
N-(3-(6-Amino-5-(2-(N-methylacrylamido)ethoxy)pyrimidin-4-yl)-5-fluoro-2-methylphenyl)-4-cyclopropyl-2-fluorobenzamide;
(S)—N-(3-(6-Amino-5-(2-(N-methylacrylamido)propoxy)pyrimidin-4-yl)-5-fluoro-2-methylphenyl)-4-cyclopropyl-2-fluorobenzamide;
(S)-2-(3-(5((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one;
N-(3-(5-(((2S,4R)-1-Acryloyl-4-fluoropyrrolidin-2-yl)methoxy)-6-aminopyrimidin-4-yl)-5-fluoro-2-methyl phenyl)-4-cyclopropyl-2-fluorobenzamide,
or
N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide.

13. The method of claim 1, wherein the compound is
N-(3-(5((1-Acryloylazetidin-3-yl)oxy)-6-aminopyrimidin-4-yl)-5-fluoro-2-methylphenyl)-4-cyclopropyl-2-fluorobenzamide;
N-(3-(6-Amino-5-(2-(N-methylacrylamido)ethoxy)pyrimidin-4-yl)-5-fluoro-2-methylphenyl)-4-cyclopropyl-2-fluorobenzamide;
(S)—N-(3-(6-Amino-5-(2-(N-methylacrylamido)propoxy)pyrimidin-4-yl)-5-fluoro-2-methylphenyl)-4-cyclopropyl-2-fluorobenzamide;
(S)-2-(3-(5((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one;
N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide,
or
N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide.

* * * * *